United States Patent [19]

Beck

[11] Patent Number: 4,589,905
[45] Date of Patent: May 20, 1986

[54] HERBICIDAL AND ALGICIDAL 1-ARYL-5-CYANO-1H-PYRAZOLE-4-CARBOXAMIDES

[75] Inventor: James R. Beck, Indianapolis, Ind.

[73] Assignee: Eli Lilly and Company, Indianapolis, Ind.

[21] Appl. No.: 650,132

[22] Filed: Sep. 13, 1984

Related U.S. Application Data

[63] Continuation-in-part of Ser. No. 549,133, Nov. 7, 1983, abandoned.

[51] Int. Cl.⁴ .................... A01N 43/56; A01N 43/40; C07D 231/14; C07D 401/04
[52] U.S. Cl. .......................................... 71/66; 71/67; 71/92; 544/124; 544/128; 544/140; 546/162; 546/211; 546/279; 546/193; 548/374; 548/378
[58] Field of Search ............... 548/374, 378; 546/162, 546/211, 279, 193; 544/124, 128, 140; 71/66, 67, 92

[56] References Cited

U.S. PATENT DOCUMENTS 4,134,987  1/1979  Huppatz ............................ 548/378
4,459,150  7/1984  Hatton et al. ......................... 71/92

FOREIGN PATENT DOCUMENTS 57-106665  7/1982  Japan ..................... 71/92

OTHER PUBLICATIONS

*Bull. Soc. Chim. Fr.*, 4, 1336-43 (1971).
CA 75:35874p (1971).
Derwent Abstract 66918 E/32 (1982).
*J. Chem. Soc.* (c), 1969(11), 1495-9.

*Primary Examiner*—Richard A. Schwartz
*Assistant Examiner*—Kurt G. Briscoe
*Attorney, Agent, or Firm*—Kathleen R. S. Page; Bruce J. Barclay; Arthur R. Whale

[57] ABSTRACT

The present invention is directed to compounds of the formula

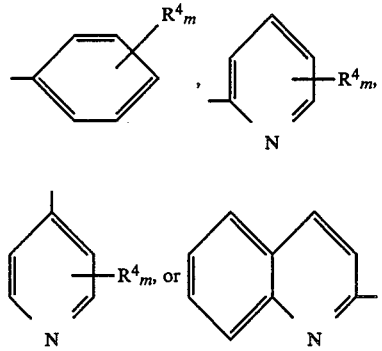

wherein
$R^1$ is $C_1$-$C_6$ alkyl, $C_5$-$C_6$ cycloalkyl, each of $R^2$ and $R^3$ is taken separately and is independently hydrogen, $C_1$-$C_4$ alkyl, $C_3$-$C_4$ alkenyl, $C_3$-$C_4$ alkynyl, $C_3$-$C_4$ cycloalkyl or $C_1$-$C_3$ alkoxy, or
$R^2$ and $R^3$ are taken together with the nitrogen atom to which they are attached and form piperidine, morpholine or pyrrolidine;
each $R^4$ independently is halogen, $C_1$-$C_4$ alkyl, $C_1$-$C_{phd\ 4}$ alkoxy, $C_1$-$C_4$ haloalkyl, $C_1$-$C_4$ haloalkoxy or cyano;
X is O or S; and
m is 0-3;

with the provisos that when $R^4$ is $C_1$-$C_4$ alkyl, that substituent exists at other than the 2 or 6 position of the phenyl ring; and when $R^2$ is $C_1$-$C_3$ alkoxy, $R^3$ is other than $C_1$-$C_3$ alkoxy.

These compounds exhibit activity as terrestrial herbicides, aquatic herbicides, and aquatic algicides.

45 Claims, No Drawings

HERBICIDAL AND ALGICIDAL 1-ARYL-5-CYANO-1H-PYRAZOLE-4-CARBOXAMIDES

CROSS-REFERENCE TO RELATED APPLICATION

This is a continuation-in-part of my application Ser. No. 549,133, filed Nov. 7, 1983 now abandoned.

SUMMARY OF THE INVENTION

The present invention relates to a compound of the formula

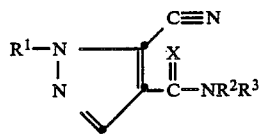

wherein
$R^1$ is $C_1$-$C_6$ alkyl, $C_5$-$C_6$ cycloalkyl,

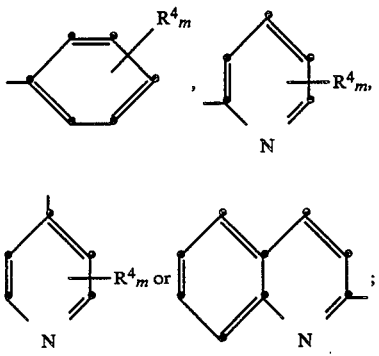

each of $R^2$ and $R^3$ is taken separately and is independently hydrogen, $C_1$-$C_4$ alkyl, $C_3$-$C_4$ alkenyl, $C_3$-$C_4$ alkynyl, $C_3$-$C_4$ cycloalkyl or $C_1$-$C_3$ alkoxy, or
$R^2$ and $R^3$ are taken together with the nitrogen atom to which they are attached and form piperidine, morpholine or pyrrolidine;
each $R^4$ independently is halogen, $C_1$-$C_4$ alkyl, $C_1$-$C_4$ alkoxy, $C_1$-$C_4$ haloalkyl, $C_1$-$C_4$ haloalkoxy or cyano;
X is O or S; and
m is 0-3;
with the provisos that when $R^4$ is $C_1$-$C_4$ alkyl, that substituent exists at other than the 2 or 6 position of the phenyl ring; and when $R^2$ is $C_1$-$C_3$ alkoxy $R^3$ is other than $C_1$-$C_3$ alkoxy.

The present compounds are useful as terrestrial and aquatic herbicides and aquatic algicides. Compositions containing these compounds are also disclosed.

DETAILED DESCRIPTION OF THE INVENTION

In the above formula, $C_1$-$C_4$ alkyl represents a straight or branched alkyl chain having from one to four carbon atoms. Typical $C_1$-$C_4$ alkyl groups include methyl, ethyl, n-propyl, isopropyl, n-butyl, sec.-butyl, t-butyl, and the like. The term $C_1$-$C_6$ alkyl includes the foregoing groups as well as $C_5$ and $C_6$ groups such as n-pentyl, tert-pentyl, 3-pentyl, n-hexyl, and 1-methyl-1-ethylpropyl.

$C_1$-$C_4$ Alkoxy represents a straight or branched alkoxy chain having from one to four carbon atoms. Typical $C_1$-$C_4$ alkoxy groups include methoxy, ethoxy, n-propoxy, isopropoxy, n-butoxy, sec.-butoxy, isobutoxy, t-butoxy, and the like.

The terms "halogen" or "halo" represent fluorine, chlorine, bromine and iodine.

$C_1$-$C_4$ Haloalkyl represents a $C_1$-$C_4$ alkyl group bearing one or more halogen substituents. Such haloalkyl groups include trifluoromethyl, 2,2,2-trifluoroethyl, pentabromoethyl, 3-chloropropyl, 2-iodopropyl, 4-fluorobutyl and the like.

$C_1$-$C_4$ Haloalkoxy is a $C_1$-$C_4$ alkoxy group bearing one or more halogen atoms. Typical members of this classification include trifluoromethyl, 1,1,2,2-tetrafluoroethoxy, pentafluoroethoxy, 3-bromopropoxy, 4-chlorobutoxy, 4-iodobutoxy and the like.

$C_3$-$C_4$ Alkenyl is a carbon chain having from three or four carbon atoms and at least one carboncarbon double bond. Typical $C_3$-$C_4$ alkenyl groups include allyl, 2-butenyl, and the like.

$C_3$-$C_4$ Alkynyl is a carbon chain having from three or four carbon atoms and at least one carboncarbon triple bond. Typical $C_3$-$C_4$ alkynyl groups include propynyl, 1-butynyl, and the like.

Compounds of the present invention wherein $R^1$ is any of the specified aryl or heteroaryl groups are preferably prepared by the following synthetic process. The process involves reacting an aryl or heteroarylhydrazine derivative with an alkyl (alkoxymethylene)cyanoacetate analog to prepare the corresponding 5-amino-1-substituted-1H-pyrazole-4-carboxylic acid ester. Next, the amino derivative is converted to the halogen derivative to provide the corresponding 5-halopyrazolecarboxylic acid ester derivative. This compound is then converted into the 5-cyanopyrazolecarboxylic acid ester, which is finally reacted with an appropriately substituted amine to give the corresponding compound of the invention. The scheme for this reaction is represented by the following:

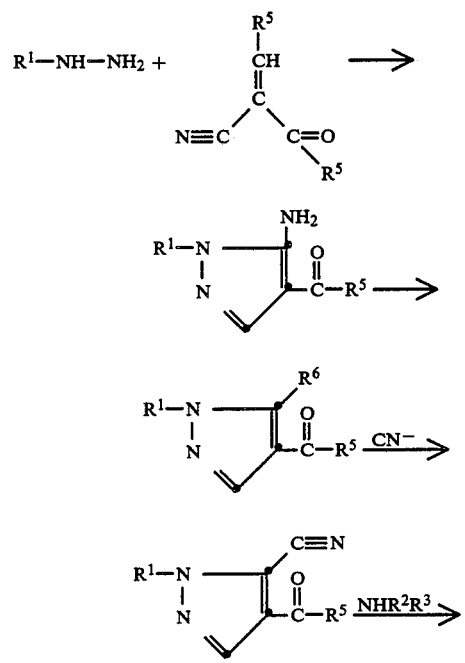

-continued

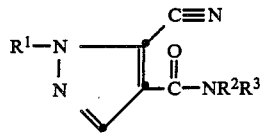

wherein $R^1$, $R^2$ and $R^3$ are as defined above, $R^5$ is $C_1$-$C_6$ alkoxy and $R^6$ is halogen.

The reaction of an aryl or heteroarylhydrazine with an alkyl(alkoxymethylene)cyanoacetate to prepare a 5-amino-4-pyrazolecarboxylic acid ester is readily practiced by well known procedures. Typically equimolar quantities of the two starting materials are combined in a suitable solvent, such as methanol or ethanol. The mixture is stirred at a temperature in the range of from about 20° C. to 200° C., more preferably at reflux temperature of the reaction mixture. The product thus formed after about 2 to 24 hours may then be isolated and purified according to standard procedures.

The 5-halogen-4-pyrazolcarboxylic acid esters used as starting materials in the present reaction scheme are prepared by different procedures depending on the desired halogen atom. Compounds wherein $R^6$ in the above reaction scheme is chlorine are prepared by employing nitrosyl chloride as both the diazotizing and halogenating agent. This reaction is typically performed in a non-reactive organic solvent and preferably in the presence of an acid catalyst. Typical solvents include most halogenated solvents with chloroform and carbon tetrachloride being preferred. An excess of the nitrosyl chloride is typically bubbled into the reaction mixture for about 5 to 30 minutes. The mixture can then be heated on a steam bath for a short period of time. The product may then be isolated by simply removing the volatiles under reduced pressure and purifying the product by common techniques if desired.

Intermediates wherein $R^6$ is bromine or iodine are prepared by employing an alkyl nitrite diazotizing agent and the corresponding halogen source as desired. Typical halogen sources include bromine, iodine, bromoform, iodoform and the like. Suitable alkyl nitrite reagents include, but are not limited to, t-butyl nitrite, isoamylnitrite and the like. Typically the reaction is performed in a suitable organic solvent such as chloroform or carbon tetrachloride by the addition of the alkyl nitrite dropwise to the reaction mixture. The reaction is usually complete after about 1 to 48 hours when conducted at a temperature between 0° C. and 100° C., more preferably from 10° C. to 50° C. Typically the reaction is worked up by simply evaporating the reaction mixture to dryness under reduced pressure and purifying the residue if desired by standard techniques such as crystallization or column chromatography.

Intermediates wherein $R^6$ is fluorine are prepared by displacing chlorine from the corresponding pyrazolecarboxylic acid ester. This reaction is conducted by adding an excess of fluorinating agent to the appropriate starting material dissolved in a suitable solvent. Suitable solvents include DMF and DMSO with the latter being preferred. Typical fluorinating agents include the alkali metal fluorides such as sodium fluoride, potassium floride and cesium floride. Before being used in the reaction the fluorinating agent should be dried so as to remove any residual water. Generally this can be performed by refluxing the fluorinating agent in a water immiscible solvent such as toluene. The solvent is then removed before combining the reaction ingredients.

The reaction is substantially complete after about 1 to 48 hours when conducted at a temperature in the range from about 75° C. to about 200° C., more preferably from 100° C. to about 150° C. The product is then generally isolated by pouring the cooled reaction mixture into ice water and collecting the precipitated solid by filtration. The product thus isolated may then be purified if desired by routine procedures.

Preparation of the 5-cyano-4-pyrazolecarboxylic acid ester starting materials can also be performed by procedures well known to those skilled in the art. Preferably these compounds are prepared by reacting the 5-halopyrazole derivative with an alkali metal cyanide agent in the presence of a suitable solvent. Suitable solvents include most of the aprotic solvents with DMF, DMSO and hexamethylphosphoramide being preferred. Typical alkali metal cyanide reagents include sodium cyanide, lithium cyanide, potassium cyanide and the like. Typically, these cyanide reagents are dried according to standard procedures to remove any residual moisture. The reaction is substantially complete after about 1 to 48 hours when conducted at a temperature in the range of from about 50° C. to about 200° C., more preferably from about 80° C. to 140° C. The product is then generally isolated by pouring the cooled reaction mixture into ice water and collecting the precipitated solid by filtration. The product thus isolated may then be purified if desired by routine procedures.

The carboxamides of the invention are finally prepared by reacting the 5-cyano-4-pyrazolecarboxylic acid ester derivative with an appropriately substituted amine under standard reaction conditions. This reaction can be carried out by combining the carboxylic acid derivative with about an equimolar quantity of the amine in a mutual solvent such as tetrahydrofuran, diethyl ether, dichloromethane, dioxane, dimethylsulfoxide, dimethylformamide, benzene, toluene and the like. The reaction is substantially complete after about 2 to 200 hours when carried out at a temperature from about 0° C. to 200° C., preferably from about 30° to about 100° C. The product of the reaction may then be isolated by simply removing the reaction solvent, for instance by evaporation under reduced pressure. Also the reaction mixture may be added to water and the product collected by filtration or extracted into a water immiscible solvent. The product thus isolated can be further purified if desired by any one of several well known techniques.

An alternative procedure for preparing the 1-aryl and 1-heteroaryl compounds of the invention involves a variation of the above described reactions. For example, a 5-halogen-4-pyrazolecarboxylic acid or ester may be converted directly to the 5-halo-4-pyrazolecarboxamide, which may then be reacted with the appropriate alkali metal cyanide reagent to provide a compound of the invention. The scheme for this reaction is as follows:

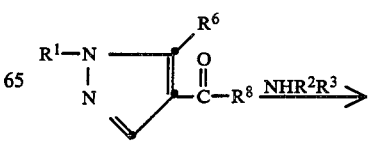

-continued

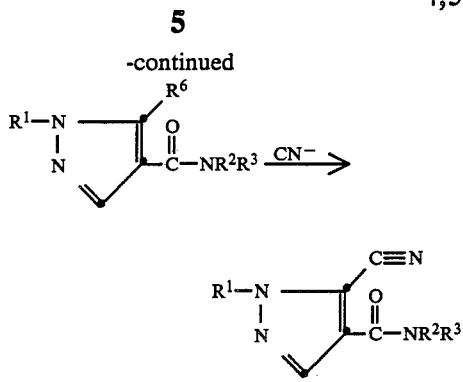

wherein $R^1$, $R^2$, $R^3$ and $R^6$ are as defined above and $R^8$ is hydroxy, $C_1$–$C_6$ alkoxy, halogen,

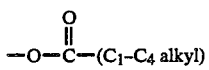

and the like.

The detailed procedures of each of these reaction steps are outlined above.

Compounds of the present invention wherein $R^1$ is $C_1$–$C_6$ alkyl or $C_5$–$C_6$ cycloalkyl are prepared according to the following reaction scheme wherein $R^1$ represents $C_1$–$C_6$ alkyl or $C_5$–$C_6$ cycloalkyl and $R^5$, as above, represents $C_1$–$C_6$ alkoxy.

and M. L. Bender, *J. Amer. Chem. Soc.*, 71, 1767 (1949) to obtain the corresponding 5-formyl compound.

The 5-formyl compound is then reacted with hydroxylamine. The reaction is conducted in a suitable solvent, which can be ethanol or methanol. Suitable reaction temperatures are from 20° C. to 100° C. The reaction yields the 5-(hydroxyiminomethyl) compound, which can be dehydrated to the corresponding 5-cyano compound. The dehydration can be accomplished in any of numerous known methods. One such method is dehydration by the use of thionyl chloride, conducted in a suitable solvent such as ether, toluene, or hexane. Reaction temperatures are desirably 20° C. to 100° C.

As a result of the foregoing reaction, 5-cyano-1-alkyl or cycloalkyl-1H-pyrazole-4-carboxylic esters are produced. They can be converted to the final cyanopyrazole herbicides in accordance with the present invention by the same techniques described above for 1-aryl and 1-heteroaryl compounds of the present invention.

The compounds of the present invention may also be prepared by hydrolyzing the 5-cyano-4-pyrazolecarboxylic acid ester starting material as prepared above to the corresponding 5-cyano-4-pyrazolecarboxylic acid. The carboxamide derivatives are then prepared by the direct coupling of a 5-cyano-4-pyrazolecarboxylic acid with an appropriately substituted amine in the presence of a coupling reagent to provide the corresponding carboxamide according to the following reaction scheme:

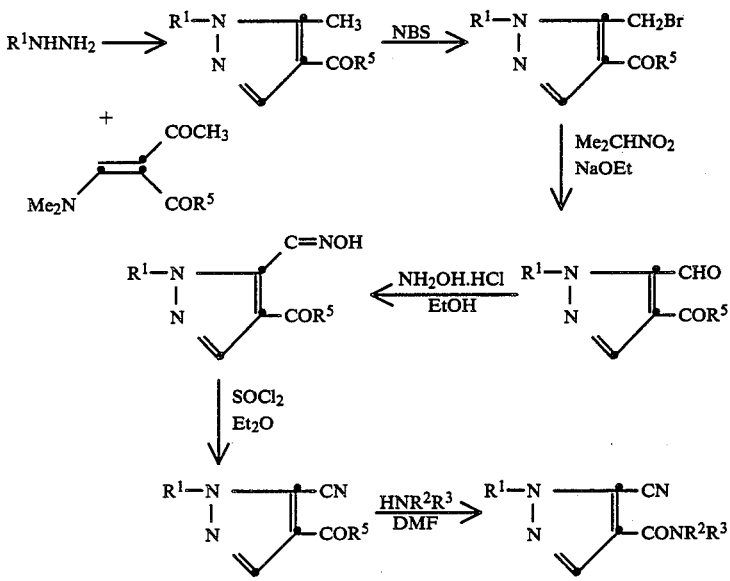

Thus, an alkyl- or cycloalkylhydrazine is reacted with an alkyl α-acetyl-α-(dimethylaminomethylene)acetate to produce a 5-methylpyrazole. The reaction is conducted in a suitable solvent, such as an alkanol and at temperatures of from 20° C. to 200° C., conveniently at the reflux temperature of the solvent. The product of the reaction is a 5-methyl-1-alkyl or cycloalkyl-1H-pyrazole-4-carboxylic acid ester.

This product is then brominated to obtain a 5-(bromomethyl) group. Conveniently, N-bromosuccinimide is employed, in a suitable solvent such as carbon tetrachloride and at reaction temperatures of from 20° C. to 100° C. The 5-(bromomethyl) product can then be treated in accordance with the procedures of H. B. Hass

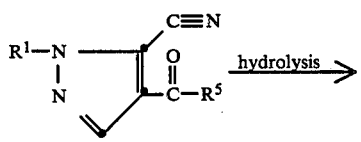

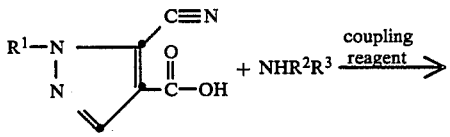

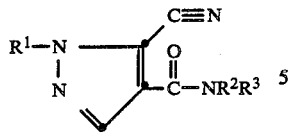

wherein R¹, R², R³ and R⁵ are as defined above.

This reaction process requires the use of a coupling reagent, for example any of the type of coupling reagents commonly employed in the synthesis of peptides. Examples of such coupling reagents include carbodiimides, such as N,N'-dicyclohexylcarbodiimide, N,N'-diisopropylcarbodiimide or N,N'-diethylcarbodiimide; the imidazoles such as carbonyldiimidazole as well as reagents such as N-ethoxycarbonyl-2-ethoxy-1,2-dihydroquinoline (EEDQ). The direct coupling of a 5-cyano-4-pyrazolecarboxylic acid and an amine is carried out by adding about an equimolar quantity of the amine starting material to a solution of the carboxylic acid in the presence of an equimolar quantity or slight excess of coupling reagent. The reaction generally is carried out in an unreactive organic solvent such as dichloromethane or dimethylformamide and is usually complete within about 24 hours when conducted at a temperature in the range of about 0° C. to about 30° C. The product is then typically isolated by filtration. The carboxamide product thus formed can be further purified if needed by any of several routine methods including crystallization from common solvents, chromatography over solid supports such as silica or alumina, and related purification techniques.

The conversion of the carboxylic acid ester derivative to the carboxylic acid is accomplished by well known hydrolysis conditions. This reaction is typically performed with a suitable base in a mutual organic solvent such as aqueous methanol or ethanol. Suitable bases include the alkali metal hydroxides, preferably sodium hydroxide and potassium hydroxide. Typically the reaction mixture is refluxed for about 1 to 10 minutes and then acidified. The resulting precipitate may then be either extracted into a water immiscible solvent or collected by filtration. Purification may be performed if desired by any one of several standard techniques.

The present compounds can also be prepared by reacting a 5-cyano-4-pyrazolecarboxylic acid halide with an appropriate amine according to the general procedure outlined above in the reaction of an amine with a carboxylic acid ester starting material. The acid halides are readily prepared by reacting a halogenating agent with a 4-pyrazolecarboxylic acid.

Thiocarboxamides defined by the above general formula wherein X is sulfur form another important group of compounds that are herbicidally and algicidally active and are a further embodiment of this invention. The thiocarboxamides of the invention are preferably prepared by thiating the corresponding carboxamide according to the following scheme:

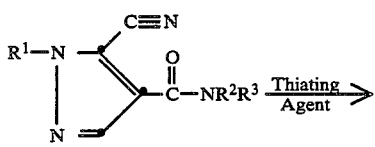

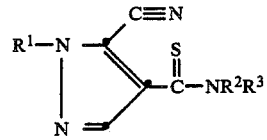

wherein R¹, R² and R³ are as defined above.

Any of several thiating agents can be employed in this reaction including phosphorous pentasulfide. Another preferred thiating agent is Lawesson's Reagent, which is 2,4-bis(4-methoxyphenyl)-1,3-dithia-2,4-diphosphetane-2,4-disulfide. This thiating agent and its general uses are described in detail in Tetrahedron Letters, 21, 4061 (1980). The thiation reaction is preferably carried out by combining approximately equimolar quantities of the carboxamide and Lawesson's Reagent in a mutual organic solvent such as toluene or dioxane. The reaction is generally complete within about 1 hour to about 10 hours when carried out at a temperature of about 50° C. to about 150° C. The thiocarboxamide thus formed can be isolated and purified by normal methods such as crystallization and the like.

Arylhydrazine and alkyl(alkoxymethylene)cyanoacetate starting materials are either commercially available or readily prepared by known procedures. For example, phenylhydrazine compounds are readily prepared by reacting an appropriately substituted aniline with nitrous acid and then stannous chloride according to standard procedures.

The following examples are illustrative of compounds of the present invention as well as methods of their preparation. These examples are not intended to be limiting to the scope in any respect and should not be so construed.

Examples 1 through 40 were prepared by the preferred process as outlined above, that is the reaction of a 5-cyano-4-pyrazolecarboxylic acid ester derivative with an appropriately substituted amine to give the corresponding carboxamide of the invention.

EXAMPLE 1

5-Cyano-1-(2-pyridinyl)-N-methyl-1H-pyrazole-4-carboxamide

A. 5-Amino-1-(2-pyridinyl)-1H-pyrazole-4-carboxylic acid, ethyl ester

A solution of 21.83 g of 2-hydrazinopyridine and 38.2 g of ethyl(ethoxymethylene)cyanoacetate dissolved in 150 ml of acetic acid and 50 ml of water was heated on a steam bath for approximately 16 hours. The reaction mixture was allowed to cool to room temperature and placed in a refrigerator whereupon crystals slowly formed. The precipitated solid was collected by filtration and washed with cold 50% aqueous ethanol to provide 23.62 g of 5-amino-1-(2-pyridinyl)-1H-pyrazole-4-carboxylic acid, ethyl ester. Yield 50.9%. MP=89°-91° C.

B. 5-Chloro-1-(2-pyridinyl)-1H-pyrazole-4-carboxylic acid, ethyl ester

Nitrosyl chloride was bubbled through a solution of 23.62 g. of 5-amino-1-(2-pyridinyl)-1H-pyrazole-4-carboxylic acid, ethyl ester in 100 ml of chloroform for approximately 5 minutes. The reaction mixture was heated on a steam bath for another 5 minutes and the volatiles were removed under reduced pressure to provide an oil. The residue was cooled in the refrigerator whereupon crystals formed. The solid was crystallized from ethanol and collected by filtration to provide 16.3 g of 5-chloro-1-(2-pyridinyl)-1H-pyrazole-4-carboxylic acid, ethyl ester. Yield 64.8%. MP=50°-51° C.

Analysis calculated for $C_{11}H_{10}ClN_3O_2$: Theory: C, 52.50; H, 4.01; N, 16.70; Found: C, 52.22; H, 3.75; N, 16.59.

C. 5-Cyano-1-(2-pyridinyl)-1H-pyrazole-4-carboxylic acid, ethyl ester

A solution of 7.36 g of 5-chloro-1-(2-pyridinyl)-1H-pyrazole-4-carboxylic acid, ethyl ester, 3.2 g of sodium cyanide and 25 ml of DMF was heated at approximately 100° C. for 3 hours. The reaction mixture was cooled and poured into 300 ml of ice water. The precipitated solid was collected by filtration to afford 5.79 g of solid. This material was recrystallized from ethanol to provide 4.72 g of 5-cyano-1-(2-pyridinyl)-1H-pyrazole-4-carboxylic acid, ethyl ester. MP=112°-114° C.

Analysis calculated for $C_{12}H_{10}N_4O_2$: Theory: C, 59.50; H, 4.16; N, 23.13; Found: C, 59.43; H, 4.11; N, 23.06.

D. To a solution of 2.5 g of 5-cyano-1-(2-pyridinyl)-1H-pyrazole-4-carboxylic acid, ethyl ester in 20 ml of DMF was added an excess of 40% aqueous monomethylamine so as not to precipitate out the pyrazole starting material. Approximately 24 hours later additional monomethylamine was added to the reaction mixture as well as additional DMF so as to keep these reactants in solution. The reaction mixture was heated and subsequently added to 150 ml of ice water. The precipitated solid was collected by filtration and recrystallized from methanol to afford 1.2 g of 5-cyano-1-(2-pyridinyl)-N-methyl-1H-pyrazole-4-carboxamide. MP=200°-202° C.

Analysis calculated for $C_{11}H_9N_4O$: Theory: C, 58.15; H, 3.99; N, 30.82; Found: C, 57.87; H, 3.83; N, 30.53.

EXAMPLE 2

5-Cyano-1-[2-(trifluoromethyl)-4-chlorophenyl]-N-methyl-1H-pyrazole-4-carboxamide

A.
5-Amino-1-[2-(trifluoromethyl)-4-chlorophenyl]-1H-pyrazole-4-carboxylic acid, ethyl ester A solution of 31.58 g of 2-(trifluoromethyl)-4-chlorophenylhydrazine and 27.92 g of ethyl(ethoxymethylene)cyanoacetate dissolved in 225 of acetic acid and 75 ml of water was heated on a steam bath for approximately 16 hours. The reaction mixture was cooled to room temperature and placed in the refrigerator. The precipitated solid was collected by filtration and combined with the solids isolated from the filtrate to provide 43 g of 5-amino-1-[2-(trifluoromethyl)-4-chlorophenyl]-1H-pyrazole-4-carboxylic acid, ethyl ester. MP=114°-116° C.

B.
5-Chloro-1-[2-(trifluoromethyl)-4-chlorophenyl]-1H-pyrazole-4-carboxylic acid, ethyl ester Hydrochloric acid gas was bubbled through a solution of 26 g of 5-amino-1-[2-(trifluoromethyl)-4-chlorophenyl]-1H-pyrazole-4-carboxylic acid, ethyl ester dissolved in 250 ml of chloroform for 1 minute. Nitrosyl chloride was next bubbled through the solution for 10 minutes. The reaction mixture was then heated on a steam bath and the volatiles were removed under reduced pressure. The residue was dissolved in hot ethanol, purified with charcoal and the product crystallized to provide 16.6 g of 5-chloro-1-[2-(trifluoromethyl)-4-chlorophenyl]-1H-pyrazole-4-carboxylic acid, ethyl ester. MP=67°-69° C.

Analysis calculated for $C_{13}H_9Cl_2F_3N_2O_2$: Theory: C, 44.22; H, 2.57; N, 7.93; Found: C, 44.48; H, 2.33; N, 7.80.

C.
5-Cyano-1-[2-(trifluoromethyl)-4-chlorophenyl]-1H-pyrazole-4-carboxylic acid, ethyl ester A solution of 3.15 g of 5-chloro-1-[2-(trifluoromethyl)-4-chlorophenyl]-1H-pyrazole-4-carboxylic acid, ethyl ester and 1.1 g of sodium cyanide in 25 ml of dimethylformamide was heated at approximately 100° C. for four and one-half hours. The reaction mixture also contained approximately 3 g of molecular sieve to insure dryness. The reaction mixture was cooled and poured into approximately 300 ml of ice water. The precipitated solid was collected by filtration and recrystallized from ethanol (charcoal) to provide 1 g of 5-cyano-1-[2-(trifluoromethyl)-4-chlorophenyl]-1H-pyrazole-4-carboxylic acid, ethyl ester. MP=70°-72° C.

Analysis calculated for $C_{14}H_9ClF_3N_3O_2$: Theory: C, 48.93; H, 2.64; N, 12.23; Found: C, 49.16; H, 2.39; N, 11.93.

D. A solution of 1.23 g of 5-cyano-1-[2-(trifluoromethyl)-4-chlorophenyl]-1H-pyrazole-4-carboxylic acid, ethyl ester and 8 ml of 40% aqueous monomethylamine in 20 ml of DMF was stirred at approximately 25° C. for 16 hours. The reaction mixture was poured into 150 ml of ice water and the precipitated solid was collected by filtration. The isolated material was recrystallized from ethanol to provide 535 mg of 5-cyano-1-[2-(trifluoromethyl)-4-chlorophenyl]-N-methyl-1H-pyrazole-4-carboxamide. MP=162.5°-164° C.

Analysis calculated for $C_{13}H_8ClF_3N_4O$: Theory: C, 47.51; H, 2.45; N, 17.05; Found: C, 47.74; H, 2.67; N, 17.20.

EXAMPLE 3

5-Cyano-1-(2,4-dichlorophenyl)-N-methyl-1H-pyrazole-4-carboxamide

A.
5-Cyano-1-(2,4-dichlorophenyl)-1H-pyrazole-4-carboxylic acid, ethyl ester A solution of 6.4 g. of 5-chloro-1-(2,4-dichlorophenyl)-1H-pyrazole-4-carboxylic acid, ethyl ester and 2 g of lithium cyanide dissolved in 30 ml of DMF was reacted at approximately 110° C. for 23 hours. One additional gram of lithium cyanide was added to the reaction mixture which was heated for an additional 7 hours. The mixture was poured into ice water and the precipitated solid was collected by filtration and recrystallized from 3 A alcohol (charcoal) to provide 3.75 g of 5-cyano-1-(3,4-dichlorophenyl)-1H-pyrazole-4-carboxylic acid, ethyl ester. Yield 61%. MP=79°-81° C.

Analysis calculated for $C_{13}H_9Cl_2N_3O_2$: Theory: C, 50.35; H, 2.93; N, 13.55; Found: C, 50.12; H, 3.11; N, 13.29.

B. To a solution of 2.5 g of 5-cyano-1-(2,4-dichlorophenyl)-1H-pyrazole-4-carboxylic acid, ethyl ester in 20 ml of DMF was added 20 ml of 40% aqueous monomethylamine. The reaction mixture was stirred at room temperature for approximately two and one-half hours whereupon the solution was poured into ice water. The precipitate was collected by filtration and recrystallized from methanol/water to afford 1.3 g of 5-cyano-1-(2,4- dichlorophenyl)-N-methyl-1H-pyrazole-4-carboxamide. MP=182°-183° C.

Analysis calculated for $C_{12}H_8Cl_2N_4O$: Theory: C, 48.84; H, 2.73; N, 18.98; Found: C, 48.69; H, 2.74; N, 19.23.

EXAMPLE 4

5-Cyano-1-(4-bromophenyl)-N-methyl-1H-pyrazole-4-carboxamide

A.

5-Cyano-1-(4-bromophenyl)-1H-pyrazole-4-carboxylic acid, ethyl ester

A solution of 6.6 g of 5-chloro-1-(4-bromophenyl)-1H-pyrazole-4-carboxylic acid, ethyl ester in 30 ml of DMF with 2 g of sodium cyanide was heated at approximately 95° C. for 3 hours. The reaction mixture was poured into ice water and the precipitated solid was collected by filtration. The product was recrystallized from 3 A alcohol to afford 5.3 g of 5-cyano-1-(4-bromophenyl)-1H-pyrazole-4-carboxylic acid, ethyl ester. MP=104°-105° C.

Analysis calculated for $C_{13}H_{10}BrN_3O_2$: Theory: C, 48.77; H, 3.15; N, 13.13; Found: C, 48.90; H, 2.91; N, 13.23.

B. A solution of 3.2 g of 5-cyano-1-(4-bromophenyl)-1H-pyrazole-4-carboxylic acid, ethyl ester in 40 ml of 3 A alcohol and 10 ml of 40% aqueous monomethylamine was refluxed for approximately 2 hours. Ten additional milliliters of 40% aqueous monomethylamine was added to the reaction mixture which was then refluxed for an additional 3 hours. The mixture was cooled and the precipitated solid was collected by filtration to provide 1 g of 5-cyano-1-(4-bromophenyl)-N-methyl-1H-pyrazole-4-carboxamide. MP=240°-241° C.

Analysis calculated for $C_{12}H_9BrN_4O$: Theory: C, 47.29; H, 2.97; N, 18.36; Found: C, 47.39; H, 3.07; N, 18.49.

The following compounds were prepared by the procedures described above.

EXAMPLE 5

5-Cyano-1-phenyl-N-cyclopropyl-1H-pyrazole-4-carboxamide, MP=220°-222° C.

Analysis calculated for $C_{14}H_{12}N_4O$: Theory: C, 66.66; H, 4.79; N, 22.21; Found: C, 66.47; H, 4.68; N, 22.06.

EXAMPLE 6

5-Cyano-1-(3-bromophenyl)-N-methyl-1H-pyrazole-4-carboxamide, MP=178.5°-180.5° C.

Analysis calculated for $C_{12}H_9BrN_4O$: Theory: C, 47.24; H, 2.97; N, 18.36; Found: C, 47.33; H, 3.03; N, 18.26.

EXAMPLE 7

5-Cyano-1-(3-bromophenyl)-N-ethyl-1H-pyrazole-4-carboxamide, MP=154.5°-156° C.

Analysis calculated for $C_{13}H_{11}BrN_4O$: Theory: C, 48.92; H, 3.47; N, 17.55; Found: C, 48.75; H, 3.46; N, 17.34.

EXAMPLE 8

5-Cyano-1-[3-(trifluoromethyl)phenyl]-N-methyl-1H-pyrazole-4-carboxamide, MP=151°-153° C.

Analysis calculated for $C_{13}H_9F_3N_4O$: Theory: C, 53.07; H, 3.08; N, 19.04; Found: C, 53.29; H, 3.28; N, 18.88.

EXAMPLE 9

5-Cyano-1-[3-(trifluoromethyl)phenyl]-N-ethyl-1H-pyrazole-4-carboxamide, MP=143°-145° C.

Analysis calculated for $C_{14}H_{11}F_3N_4O$: Theory: C, 54.55; H, 3.60; N, 18.17; Found: C, 54.75; H, 3.39; N, 18.28.

EXAMPLE 10

5-Cyano-1-(2,4-dibromophenyl)-N-methyl-1H-pyrazole-4-carboxamide, MP=198°-200° C.

Analysis calculated for $C_{12}H_8Br_2N_4O$: Theory: C, 37.53; H, 2.10; N, 14.59; Found: C, 37.50; H, 2.15; N, 14.47.

EXAMPLE 11

5-Cyano-1-(3-methylphenyl)-N-methyl-1H-pyrazole-4-carboxamide, MP=159°-161° C.

Analysis calculated for $C_{13}H_{12}N_4O$: Theory: C, 64.99; H, 5.03; N, 23.32; Found: C, 64.70; H, 5.09; N, 23.18.

EXAMPLE 12

5-Cyano-1-(3-fluorophenyl)-N-methyl-1H-pyrazole-4-carboxamide, MP=188°-189.5° C.

Analysis calculated for $C_{12}H_9FN_4O$: Theory: C, 59.02; H, 3.71; N, 22.94; Found: C, 58.81; H, 3.62; N, 22.70.

EXAMPLE 13

5-Cyano-1-(3-fluorophenyl)-N-ethyl-1H-pyrazole-4-carboxamide, MP=163°-164° C.

Analysis calculated for $C_{13}H_{11}FN_4O$: Theory: C, 60.46; H, 4.29; N, 21.69; Found: C, 60.64; H, 4.11; N, 21.46.

EXAMPLE 14

5-Cyano-1-(4-pyridinyl)-N-methyl-1H-pyrazole-4-carboxamide, MP=216°-218° C.

Analysis calculated for $C_{11}H_9N_5O$: Theory: C, 58.14; H, 3.99; N, 30.82; Found: C, 57.93; H, 3.86; N, 30.66.

EXAMPLE 15

5-Cyano-1-(3-chlorophenyl)-N-methyl-1H-pyrazole-4-carboxamide, MP=181°-182° C.

Analysis calculated for $C_{12}H_9ClN_4O$: Theory: C, 55.29; H, 3.48; N, 21.49; Found: C, 55.44; H, 3.56; N, 21.63.

EXAMPLE 16

5-Cyano-1-(3-chlorophenyl)-N-ethyl-1H-pyrazole-4-carboxamide, MP=135°-136° C.

Analysis calculated for $C_{13}H_{11}ClN_4O$: Theory: C, 56.84; H, 4.04; N, 20.39; Found: C, 56.94; H, 4.06; N, 20.38.

EXAMPLE 17

5-Cyano-1-(5-chloro-2-pyridinyl)-N-methyl-1H-pyrazole-4-carboxamide, MP=218°–219° C.

Analysis calculated for $C_{11}H_8ClN_5O$: Theory: C, 50.49; H, 3.08; N, 26.76; Found: C, 50.29; H, 3.27; N, 26.53.

EXAMPLE 18

5-Cyano-1-(2-pyridinyl)-N-ethyl-1H-pyrazole-4-carboxamide, MP=210.5°–212° C.

Analysis calculated for $C_{12}H_{11}N_5O$: Theory: C, 59.74; H, 4.60; N, 29.03; Found: C, 59.72; H, 4.54; N, 29.02.

EXAMPLE 19

5-Cyano-1-(2-chlorophenyl)-N-methyl-1H-pyrazole-4-carboxamide, MP=181°–183° C.

Analysis calculated for $C_{12}H_9ClN_4O$: Theory: C, 55.29; H, 3.48; N, 21.49; Found: C, 55.56; H, 3.46; N, 21.36.

EXAMPLE 20

5-Cyano-1-(4-methoxyphenyl)-N-methyl-1H-pyrazole-4-carboxamide, MP=190.5°–192° C.

Analysis calculated for $C_{13}H_{12}N_4O_2$: Theory: C, 60.93; H, 4.72; N, 21.86; Found: C, 60.66; H, 4.61; N, 21.61.

EXAMPLE 21

5-Cyano-1-(3,4-dichlorophenyl)-N-methyl-1H-pyrazole-4-carboxamide, MP=196°–197° C.

Analysis calculated for $C_{12}H_8Cl_2N_4O$: Theory: C, 48.44; H, 2.73; N, 18.98; Found: C, 48.54; H, 2.79; N, 18.89.

EXAMPLE 22

5-Cyano-1-(3,4-dichlorophenyl)-N-ethyl-1H-pyrazole-4-carboxamide, MP=151°–153° C.

Analysis calculated for $C_{13}H_{10}Cl_2N_4O$: Theory: C, 50.51; H, 3.26; N, 18.12; Found: C, 50.72; H, 3.16; N, 18.27.

EXAMPLE 23

5-Cyano-1-[2-(trifluoromethyl)phenyl]-N-methyl-1H-pyrazole-4-carboxamide, MP=182°–184° C.

Analysis calculated for $C_{13}H_9F_3N_4O$: Theory: C, 53.07; H, 3.08; N, 19.04; Found: C, 52.99; H, 3.04; N, 18.84.

EXAMPLE 24

5-Cyano-1-(4-fluorophenyl)-N-methyl-1H-pyrazole-4-carboxamide, MP=186°–188° C.

Analysis calculated for $C_{12}H_9FN_4O$: Theory: C, 59.02; H, 3.71; N, 22.94; Found: C, 58.80; H, 3.49; N, 22.71.

EXAMPLE 25

5-Cyano-1-(4-fluorophenyl)-N-ethyl-1H-pyrazole-4-carboxamide, MP=163°–165° C.

Analysis calculated for $C_{13}H_{11}FN_4O$: Theory: C, 60.46; H, 4.29; N, 21.69; Found: C, 60.21; H, 4.17; N, 21.44.

EXAMPLE 26

5-Cyano-1-(3-chloro-4-methylphenyl)-N-methyl-1H-pyrazole-4-carboxamide, MP=186°–190° C.

Analysis calculated for $C_{13}H_{11}ClN_4O$: Theory: C, 56.84; H, 4.04; N, 20.39; Found: C, 57.09; H, 3.90; N, 20.30.

EXAMPLE 27

5-Cyano-1-(2,3-dichlorophenyl)-N-methyl-1H-pyrazole-4-carboxamide, MP=212°–214° C.

Analysis calculated for $C_{12}H_8Cl_2N_4O$: Theory: C, 48.84; H, 2.73; N, 18.98; Found: C, 48.58; H, 2.61; N, 19.09.

EXAMPLE 28

5-Cyano-1-(3,4-dimethylphenyl)-N-methyl-1H-pyrazole-4-carboxamide, MP=195°–197° C.

Analysis calculated for $C_{14}H_{14}N_4O$: Theory: C, 66.13; H, 5.55; N, 22.03; Found: C, 65.86; H, 5.29; N, 21.75.

EXAMPLE 29

5-Cyano-1-(2-quinolinyl)-N-methyl-1H-pyrazole-4-carboxamide, MP=226°–227° C.

Analysis calculated for $C_{15}H_{11}N_5O$: Theory: C, 64.97; H, 4.00; N, 25.26; Found: C, 65.12; H, 3.80; N, 25.43.

EXAMPLE 30

5-Cyano-1-phenyl-N-propyl-1H-pyrazole-4-carboxamide, MP=168°–169° C.

Analysis calculated for $C_{14}H_{14}N_4O$: Theory: C, 66.13; H, 5.55; N, 22.03; Found: C, 65.88; H, 5.33; N, 21.85.

EXAMPLE 31

5-Cyano-1-phenyl-N-2-propenyl-1H-pyrazole-4-carboxamide, MP=163°–164° C.

Analysis calculated for $C_{14}H_{11}N_4O$: Theory: C, 66.66; H, 4.79; N, 22.21; Found: C, 66.39; H, 4.57; N, 22.08.

EXAMPLE 32

5-Cyano-1-phenyl-N-ethyl-1H-pyrazole-4-carboxamide, MP=199°–200° C.

Analysis calculated for $C_{13}H_{12}N_4O$: Theory: C, 64.99; H, 5.03; N, 23.32; Found: C, 65.18; H, 4.82; N, 23.48.

EXAMPLE 33

5-Cyano-1-(4-chlorophenyl)-N-methyl-1H-pyrazole-4-carboxamide, MP=211°–212° C.

Analysis calculated for $C_{12}H_9ClN_4O$: Theory: C, 55.29; H, 3.48; N, 21.49; Found: C, 55.13; H, 3.43; N, 21.32.

EXAMPLE 34

5-Cyano-1-(2,5-dichlorophenyl)-N-methyl-1H-pyrazole-4-carboxamide, MP=186°–187° C.

Analysis calculated for $C_{12}H_8Cl_2N_4O$: Theory: C, 48.84; H, 2.73; N, 18.98; Found: C, 48.73; H, 2.60; N, 18.84.

EXAMPLE 35

5-Cyano-1-(2,5-dichlorophenyl)-N-ethyl-1H-pyrazole-4-carboxamide, MP=170°–172° C.

Analysis calculated for $C_{13}H_{10}Cl_2N_4O$: Theory: C, 50.51; H, 3.26; N, 18.12; Found: C, 50.67; H, 3.27; N, 18.22.

EXAMPLE 36

5-Cyano-1-(4-methylphenyl)-N-methyl-1H-pyrazole-4-carboxamide, MP=205°–207° C.

Analysis calculated for $C_{13}H_{12}N_4O$: Theory: C, 64.99; H, 5.03; N, 23.32; Found: C, 65.19; H, 4.97; N, 23.04.

EXAMPLE 37

5-Cyano-1-(4-methylphenyl)-N-ethyl-1H-pyrazole-4-carboxamide, MP=209°–210° C.

Analysis calculated for $C_{14}H_{14}N_4O$: Theory: C, 66.17; H, 5.55; N, 22.03; Found: C, 66.36; H, 5.39; N, 22.16.

EXAMPLE 38

5-Cyano-1-(2,4-dichlorophenyl)-N-ethyl-1H-pyrazole-4-carboxamide, MP=140°–141° C.

Analysis calculated for $C_{13}H_{10}Cl_2N_4O$: Theory: C, 50.51; H, 3.26; N, 18.12; Found: C, 50.68; H, 3.28; N, 18.25.

EXAMPLE 39

5-Cyano-1-(4-chlorophenyl)-N-ethyl-1H-pyrazole-4-carboxamide, MP=166°–168° C.

Analysis calculated for $C_{13}H_{11}ClN_4O$: Theory: C, 56.84; H, 4.04; N, 20.39; Found: C, 56.92; H, 4.00; N, 20.23.

EXAMPLE 40

5-Cyano-1-(3-cyanophenyl)-N-methyl-1H-pyrazole-4-carboxamide, MP=206°–208° C.

Analysis calculated for $C_{13}H_9N_5O$: Theory: C, 62.15; H, 3.61; N, 27.87; Found: C, 62.10; H, 3.85; N, 27.60.

Examples 41 through 94 represent the preparation of compounds of the invention wherein a 5-cyano-4-pyrazolecarboxylic acid is converted to the corresponding compound of the invention.

EXAMPLE 41

5-Cyano-1-(3-cyanophenyl)-N-methyl-N-ethyl-1H-pyrazole-4-carboxamide

A.

5-Cyano-1-(3-cyanophenyl)-1H-pyrazole-4-carboxylic acid

Approximately 7.7 g of 5-cyano-1-(3-cyanophenyl)-1H-pyrazole-4-carboxylic acid, ethyl ester was dissolved in 75 ml of hot ethanol. To the reaction mixture was added 3.2 g of potassium hydroxide dissolved in ethanol. A small amount of water was added to the reaction mixture which was immediately poured into water. The solution was then acidified with concentrated hydrochloric acid and the precipitated solid was collected by filtration and dried to provide 4.3 g of 5-cyano-1-(3-cyanophenyl)-1H-pyrazole-4-carboxylic acid. MP=190°–192° C.

B. Two grams of carbonyldiimidazole was added to a solution of 2.0 g of 5-cyano-1-(3-cyanophenyl)-1H-pyrazole-4-carboxylic acid dissolved in 50 ml of DMF. The reaction mixture was stirred at room temperature for approximately 25 minutes whereupon 740 mg of N-ethyl-N-methylamine was added. The reaction mixture was allowed to stir for an additional 24 hours at which point the solution was poured into ice water. The precipitate solid was collected by filtration and dried to provide 1.2 g of 5-cyano-1-(3-cyanophenyl)-N-methyl-N-ethyl-1H-pyrazole-4-carboxamide following recrystallization from ethanol. MP=185°–187° C.

Analysis calculated for $C_{15}H_{13}N_5O$: Theory: C, 64.51; H, 4.69; N, 25.07; Found: C, 64.42; H, 4.47; N, 24.88.

EXAMPLE 42

5-Cyano-1-(4-chlorophenyl)-N-cyclopropyl-1H-pyrazole-4-carboxamide

A.

5-Cyano-1-(4-chlorophenyl)-1H-pyrazole-4-carboxylic acid

A hot solution of 5.61 g of potassium hydroxide dissolved in 110 ml of 3A ethanol was added to a hot solution of 11.3 g of 5-cyano-1-(4-chlorophenyl)-1H-pyrazole-4-carboxylic acid, ethyl ester dissolved in 225 ml of 3A ethanol. The precipitated salt that was formed was dissolved into 1 liter of water and the solution was acidified with concentrated hydrochloric acid. The precipitated solid was collected by filtraton and recrystallized from toluene to provide 8.47 g of 5-cyano-1-(4-chlorophenyl)-1H-pyrazole-4-carboxylic acid. MP=192°–195° C.

Analysis calculated for $C_{11}H_6ClN_3O_2$: Theory: C, 53.35; H, 2.24; N, 16.97; Found: C, 53.25; H, 2.50; N, 16.73.

B. A solution of 2.47 g of 5-cyano-1-(4-chlorophenyl)-1H-pyrazole-4-carboxylic acid and 2.03 g of carbonyldiimidazole dissolved in 25 ml of DMF was stirred at room temperature for approximately 15 minutes. Seven milliliters of cyclopropylamine was next added to the reaction mixture which was allowed to stir for approximately 16 hours. The mixture was poured into 150 ml of ice water and the precipitated solid was collected by filtration. This solid was recrystallized from ethanol and dried to afford 1.86 g of 5-cyano-1-(4-chlorophenyl)-N-cyclopropyl-1H-pyrazole-4-carboxamide. MP=204°–206° C.

Analysis calculated for $C_{14}H_{11}ClN_4O$: Theory: C, 58.65; H, 3.87; N, 19.54; Found: C, 58.70; H, 4.05; N, 19.31.

The following examples were prepared by reacting a pyrazolecarboxylic acid with an appropriate amine to provide a compound of the invention.

EXAMPLE 43

5-Cyano-1-(4-chlorophenyl)-N,N-dimethyl-1H-pyrazole-4-carboxamide, MP=123°–125° C.

Analysis calculated for $C_{13}H_{11}ClN_4O$: Theory: C, 56.84; H, 4.04; N, 20.39; Found: C, 56.78; H, 4.08; N, 20.32.

EXAMPLE 44

5-Cyano-1-(4-chlorophenyl)-N-methyl-N-ethyl-1H-pyrazole-4-carboxamide, MP=87°–89° C.

Analysis calculated for $C_{14}H_{13}ClN_4O$: Theory: C, 58.24; H, 4.54; N, 19.40; Found: C, 57.98; H, 4.49; N, 19.34.

EXAMPLE 45

5-Cyano-1-(4-chlorophenyl)-N,N-diethyl-1H-pyrazole-4-carboxamide, MP=109°–111° C.

Analysis calculated for $C_{15}H_{15}ClN_4O$: Theory: C, 59.51; H, 4.99; N, 18.50; Found: C, 59.32; H, 4.79; N, 18.33.

EXAMPLE 46

5-Cyano-1-(4-chlorophenyl)-N-ethyl-N-propyl-1H-pyrazole-4-carboxamide, MP=51°–52° C.

Analysis calculated for $C_{16}H_{17}ClN_4O$: Theory: C, 60.66; H, 5.41; N, 17.69; Found: C, 60.65; H, 5.50; N, 17.82.

EXAMPLE 47

5-Cyano-1-(4-chlorophenyl)-N,N-dipropyl-1H-pyrazole-4-carboxamide, MP=83°–84° C.

Analysis calculated for $C_{17}H_{19}ClN_4O$: Theory: C, 61.72; H, 5.79; N, 16.94; Found: C, 61.61; H, 5.58; N, 16.88.

EXAMPLE 48

1-[[1-(4-Chlorophenyl)-5-cyano-1H-pyrazole-4-yl]carbonyl]piperidine, MP=124°–125° C.

Analysis calculated for $C_{16}H_{15}ClN_4O$: Theory: C, 61.05; H, 4.80; N, 17.80; Found: C, 60.74; H, 4.74; N, 17.60.

EXAMPLE 49

5-Cyano-1-(3-chloro-4-methylphenyl)-N,N-dimethyl-1H-pyrazole-4-carboxamide, MP=109°–111° C.

Analysis calculated for $C_{14}H_{13}ClN_4O$: Theory: C, 58.24; H, 4.54; N, 19.40; Found: C, 57.96; H, 4.34; N, 19.39.

EXAMPLE 50

5-Cyano-1-(2,4-dichlorophenyl)-N,N-dimethyl-1H-pyrazole-4-carboxamide, MP=117°–119° C.

Analysis calculated for $C_{13}H_{10}Cl_2N_4O$: Theory: C, 50.51; H, 3.26; N, 18.12; Found: C, 50.25; H, 3.26; N, 17.80.

EXAMPLE 51

5-Cyano-1-(2,4-dichlorophenyl)-N-cyclopropyl-1H-pyrazole-4-carboxamide, MP=173°–174° C.

Analysis calculated for $C_{14}H_{10}Cl_2N_4O$: Theory: C, 52.36; H, 3.14; N, 17.44; Found: C, 52.38; H, 3.26; N, 17.71.

EXAMPLE 52

5-Cyano-1-(2,4-dichlorophenyl)-N-methyl-N-ethyl-1H-pyrazole-4-carboxamide, MP=75°–77° C.

Analysis calculated for $C_{14}H_{12}Cl_2N_4O$: Theory: C, 52.03; H, 3.74; N, 17.34; Found: C, 51.76; H, 3.74; N, 17.28.

EXAMPLE 53

5-Cyano-1-(2,4-dichlorophenyl)-N,N-diethyl-1H-pyrazole-4-carboxamide, MP=111°–112.5° C.

Analysis calculated for $C_{15}H_{14}Cl_2N_4O$: Theory: C, 53.43; H, 4.18; N, 16.61; Found: C, 53.23; H, 3.94; N, 16.56.

EXAMPLE 54

5-Cyano-1-(2,4-dichlorophenyl)-N-methyl-N-methoxy-1H-pyrazole-4-carboxamide, MP=143°–145° C.

Analysis calculated for $C_{13}H_{10}Cl_2N_4O_2$: Theory: C, 48.02; H, 3.10; N, 17.32; Found: C, 47.88; H, 3.09; N, 17.16.

EXAMPLE 55

5-Cyano-1-(3-bromophenyl)-N,N-dimethyl-1H-pyrazole-4-carboxamide, MP=125° C.

Analysis calculated for $C_{13}H_{11}BrN_4O$: Theory: C, 48.92; H, 3.47; N, 17.55; Found: C, 49.17; H, 3.30; N, 17.29.

EXAMPLE 56

5-Cyano-1-(3-bromophenyl)-N-methyl-N-methoxy-1H-pyrazole-4-carboxamide, MP=154°–155° C.

Analysis calculated for $C_{13}H_{11}BrN_4O_2$: Theory: C, 46.59; H, 3.31; N, 16.72; Found: C, 46.88; H, 3.45; N, 16.49.

EXAMPLE 57

5-Cyano-1-[3-(trifluoromethyl)phenyl]-N,N-dimethyl-1H-pyrazole-4-carboxamide, MP=97°–99° C.

Analysis calculated for $C_{14}H_{11}F_3N_4O$: Theory: C, 54.55; H, 3.60; N, 18.17; Found: C, 54.46; H, 3.88; N, 18.01.

EXAMPLE 58

5-Cyano-1-[3-(trifluoromethyl)phenyl]-N-cyclopropyl-1H-pyrazole-4-carboxamide, MP=180°–182° C.

Analysis calculated for $C_{15}H_{11}F_3N_4O$: Theory: C, 56.25; H, 3.46; N, 17.49; Found: C, 56.28; H, 3.50; N, 17.40.

EXAMPLE 59

5-Cyano-1-[3-(trifluoromethyl)phenyl]-N-methyl-N-ethyl-1H-pyrazole-4-carboxamide, MP=67°–68° C.

Analysis calculated for $C_{15}H_{13}F_3N_4O$: Theory: C, 55.90; H, 4.07; N, 17.38; Found: C, 55.61; H, 4.03; N, 17.64.

EXAMPLE 60

5-Cyano-1-[3-(trifluoromethyl)phenyl]-N-methyl-N-methoxy-1H-pyrazole-4-carboxamide, MP=121°–123° C.

Analysis calculated for $C_{14}H_{11}F_3N_4O_2$: Theory: C, 51.86; H, 3.42; N, 17.28; Found: C, 52.11; H, 3.51; N, 17.35.

EXAMPLE 61

5-Cyano-1-(4-bromophenyl)-N,N-dimethyl-1H-pyrazole-4-carboxamide, MP=131°–133° C.

Analysis calculated for $C_{13}H_{11}BrN_4O$: Theory: C, 48.92; H, 3.47; N, 17.55; Found: C, 48.79; H, 3.52; N, 17.51.

EXAMPLE 62

5-Cyano-1-(4-bromophenyl)-N-methyl-N-methoxy-1H-pyrazole-4-carboxamide, MP=147° C.

Analysis calculated for $C_{13}H_{11}BrN_4O_2$: Theory: C, 46.59; H, 3.31; N, 16.72; Found: C, 46.42; H, 3.24; N, 16.52.

EXAMPLE 63

5-Cyano-1-(4-bromophenyl)-N-methyl-N-ethyl-1H-pyrazole-4-carboxamide, MP=91°–93° C.

Analysis calculated for $C_{14}H_{13}BrN_4O$: Theory: C, 50.47; H, 3.93; N, 16.82; Found: C, 50.41; H, 3.76; N, 16.63.

EXAMPLE 64

5-Cyano-1-(4-bromophenyl)-N,N-diethyl-1H-pyrazole-4-carboxamide, MP=108°–110° C.

Analysis calculated for $C_{15}H_{15}BrN_4O$: Theory: C, 51.89; H, 4.35; N, 16.14; Found: C, 51.83; H, 4.32; N, 16.12.

EXAMPLE 65

5-Cyano-1-(4-bromophenyl)-N-cyclopropyl-1H-pyrazole-4-carboxamide, MP=217°–218° C.

Analysis calculated for $C_{14}H_{11}BrN_4O$: Theory: C, 50.78; H, 3.35; N, 16.92; Found: C, 50.61; H, 3.36; N, 16.80.

EXAMPLE 66

5Cyano-1-(3-fluorophenyl)-N,N-dimethyl-1H-pyrazole-4-carboxamide, MP=132°–133° C.

Analysis calculated for $C_{13}H_{11}FN_4O$: Theory: C, 60.46; H, 4.29; N, 21.69; Found: C, 60.71; H, 4.07; N, 21.70.

EXAMPLE 67

5-Cyano-1-(3-chlorophenyl)-N,N-dimethyl-1H-pyrazole-4-carboxamide, MP=111°–113° C.

Analysis calculated for $C_{13}H_{11}ClN_4O$: Theory: C, 56.84; H, 4.04; N, 20.39; Found: C, 56.66; H, 3.72; N, 20.21.

EXAMPLE 68

5-Cyano-1-(3-chlorophenyl)-N-cyclopropyl-1H-pyrazole-4-carboxamide, MP=178°–179° C.

Analysis calculated for $C_{14}H_{11}ClN_4O$: Theory: C, 58.65; H, 3.87; N, 19.54; Found: C, 58.88; H, 3.84; N, 19.68.

EXAMPLE 69

5-Cyano-1-(3-chlorophenyl)-N-methyl-N-methoxy-1H-pyrazole-4-carboxamide, MP=164°–166° C.

Analysis calculated for $C_{13}H_{11}ClN_4O_2$: Theory: C, 53.71; H, 3.81; N, 19.27; Found: C, 53.79; H, 3.81; N, 19.40.

EXAMPLE 70

5-Cyano-1-(2-pyridinyl)-N,N-diethyl-1H-pyrazole-4-carboxamide, MP=108° C.

Analysis calculated for $C_{14}H_{15}N_5O$: Theory: C, 62.44; H, 5.61; N, 26.00; Found: C, 62.37; H, 5.38; N, 26.21.

EXAMPLE 71

5-Cyano-1-(2-pyridinyl)-N-methyl-N-ethyl-1H-pyrazole-4-carboxamide, MP=106°–108° C.

Analysis calculated for $C_{13}H_{13}N_5O$: Theory: C, 61.17; H, 5.13; N, 27.43; Found: C, 60.91; H, 4.98; N, 27.17.

EXAMPLE 72

5-Cyano-1-(2-pyridinyl)-N-cyclopropyl-1H-pyrazole-4-carboxamide, MP=221°–222° C.

Analysis calculated for $C_{13}H_{11}N_5O$: Theory: C, 61.65; H, 4.38; N, 27.65; Found: C, 61.59; H, 4.48; N, b 27.55.

EXAMPLE 73

5-Cyano-1-(2-pyridinyl)-N-methyl-N-methoxy-1H-pyrazole-4-carboxamide, MP=113°–116° C.

Analysis calculated for $C_{13}H_{11}N_5O_2$: Theory: C, 56.03; H, 4.31; N, 27.22; Found: C, 55.81; H, 4.01; N, 27.03.

EXAMPLE 74

5-Cyano-1-(2-pyridinyl)-N,N-dimethyl-1H-pyrazole-4-carboxamide, MP=136°–138° C.

Analysis calculated for $C_{12}H_{11}N_5O$: Theory: C, 59.75; H, 4.56; N, 29.05; Found: C, 59.55; H, 4.87; N, 28.77.

EXAMPLE 75

1-[[5-Cyano-1-(2-pyridinyl)-1H-pyrazole-4-yl]carbonyl]morpholine, MP=115°–118° C.

Analysis calculated for $C_{14}H_{13}N_4O_2$: Theory: C, 59.36; H, 4.63; N, 24.72; Found: C, 59.24; H, 4.79; N, 24.97.

EXAMPLE 76

5-Cyano-1-phenyl-N-methyl-N-ethyl-1H-pyrazole-4-carboxamide, MP=79° C.

Analysis calculated for $C_{14}H_{14}N_4O$: Theory: C, 66.13; H, 5.55; N, 22.03; Found: C, 65.85; H, 5.31; N, 21.80.

EXAMPLE 77

5-Cyano-1-(4-methoxyphenyl)-N,N-dimethyl-1H-pyrazole-4-carboxamide, MP=113°–114° C.

Analysis calculated for $C_{14}H_{14}N_4O_2$: Theory: C, 62.21; H, 5.22; N, 20.73; Found: C, 62.46; H, 5.27; N, 20.92.

EXAMPLE 78

5-Cyano-1-(4-methoxyphenyl)-N-methyl-N-ethyl-1H-pyrazole-4-carboxamide, MP=121°–123° C.

Analysis calculated for $C_{15}H_{16}N_4O_2$: Theory: C, 63.37; H, 5.67; N, 19.71; Found: C, 63.32; N, 5.77; N, 19.65.

EXAMPLE 79

5-Cyano-1-(3,4-dichlorophenyl)-N,N-dimethyl-1H-pyrazole-4-carboxamide, MP=122°–124° C.

Analysis calculated for $C_{13}H_{10}Cl_2N_4O$: Theory: C, 50.51; H, 3.26; N, 18.12; Found: C, 50.43; H, 3.06; N, 18.08.

EXAMPLE 80

5-Cyano-1-(3,4-dichlorophenyl)-N-cyclopropyl-1H-pyrazole-4-carboxamide, MP=194°–196° C.

Analysis calculated for $C_{14}H_{10}Cl_2N_4O$: Theory: C, 52.36; H, 3.14; N, 17.44; Found: C, 52.57; H, 3.13; N, 17.50.

EXAMPLE 81

5-Cyano-1-(4-fluorophenyl)-N,N-dimethyl-1H-pyrazole-4-carboxamide, MP=118°–120° C.

Analysis calculated for $C_{13}H_{11}FN_4O$: Theory: C, 60.46; H, 4.29; N, 21.69; Found: C, 60.24; H, 4.06; N, 21.66.

EXAMPLE 82

5-Cyano-1-(2-quinolinyl)-N,N-dimethyl-1H-pyrazole-4-carboxamide, MP=167°–168° C.

Analysis calculated for $C_{16}H_{13}N_5O$: Theory: C, 65.97; H, 4.50; N, 24.04; Found: C, 66.30; H, 4.58; N, 24.03.

EXAMPLE 83

5-Cyano-1-phenyl-N,N-dimethyl-1H-pyrazole-4-carboxamide, MP=109°–110° C.

Analysis calculated for $C_{13}H_{12}N_4O$: Theory: C, 64.99; H, 5.03; N, 23.32; Found: C, 64.87; H, 5.03; N, 23.41.

EXAMPLE 84

5-Cyano-1-phenyl-N-(1-methylethyl)-1H-pyrazole-4-carboxamide, MP=208°–209° C.

Analysis calculated for $C_{14}H_{14}N_4O$: Theory: C, 66.13; H, 5.55; N, 22.03; Found: C, 65.88; H, 5.39; N, 21.90.

EXAMPLE 85

5-Cyano-1-phenyl-1H-pyrazole-4-carboxamide, MP=178°–179° C.

Analysis calculated for $C_{11}H_8N_4O$: Theory: C, 62.26; H, 3.80; N, 26.40; Found: C, 62.13; H, 3.76; N, 26.36.

EXAMPLE 86

5-Cyano-1-phenyl-N-methoxy-1H-pyrazole-4-carboxamide, MP=163°–164° C.

Analysis calculated for $C_{12}H_{10}N_4O_2$: Theory: C, 59.50; H, 4.16; N, 23.13; Found: C, 59.63; H, 3.92; N, 22.93.

EXAMPLE 87

5-Cyano-1-phenyl-N-methyl-N-methoxy-1H-pyrazole-4-carboxamide, MP=129° C.

Analysis calculated for $C_{13}H_{12}N_4O_2$: Theory: C, 60.93; H, 4.72; N, 21.86; Found: C, 61.06; H, 4.57; N, 21.67.

EXAMPLE 88

5-Cyano-1-phenyl-N,N-diethyl-1H-pyrazole-4-carboxamide, oil

Analysis calculated for $C_{15}H_{16}N_4O$: Theory: C, 67.15; H, 6.01; N, 20.88; Found: C, 66.88; H, 5.96; N, 20.63.

EXAMPLE 89

1-[(5-Cyano-1-phenyl-1H-pyrazol-4-yl)carbonyl]pyrrolidine, MP=139°–140° C.

Analysis calculated for $C_{15}H_{14}N_4O$: Theory: C, 67.65; H, 5.30; N, 21.04; Found: C, 67.87; H, 5.52; N, 21.07.

EXAMPLE 90

5-Cyano-1-phenyl-N,N-dipropyl-1H-pyrazole-4-carboxamide, oil

Analysis calculated for $C_{17}H_{20}N_4O$: Theory: C, 68.90; H, 6.80; N, 18.90; Found: C, 68.70; H, 6.57; N, 18.89.

EXAMPLE 91

5-Cyano-1-(4-methylphenyl)-N,N-dimethyl-1H-pyrazole-4-carboxamide, MP=149°–150° C.

Analysis calculated for $C_{14}H_{13}N_4O$: Theory: C, 66.13; H, 5.55; N, 22.03; Found: C, 65.88; H, 5.28; N, 21.82.

EXAMPLE 92

5-Cyano-1-(4-fluorophenyl)-N-cyclopropyl-1H-pyrazole-4-carboxamide, MP=185°–187° C.

Analysis calculated for $C_{14}H_{11}FN_4O$: Theory: C, 62.22; H, 4.10; N, 20.73; Found: C, 61.95; H, 3.83; N, 20.54.

EXAMPLE 93

5-Cyano-1-phenyl-N-methyl-N-2-propenyl-1H-pyrazole-4-carboxamide, MP=47°–50° C.

Analysis calculated for $C_{15}H_{14}N_4O$: Theory: C, 67.65; H, 5.30; N, 21.04; Found: C, 67.83; H, 5.09; N, 20.76.

EXAMPLE 94

5-Cyano-1-phenyl-N-methyl-N-cyclopropyl-1H-pyrazole-4-carboxamide, MP=79°–81° C.

Analysis calculated for $C_{15}H_{14}N_4O$: Theory: C, 67.65; H, 5.30; N, 21.04; Found: C, 67.44; H, 5.13; N, 21.00.

Examples 95 and 96 represent the reaction of a 5-halo-4-pyrazolecarboxamide derivative with a cyanating agent to give the corresponding compound of the invention.

EXAMPLE 95

5-Cyano-1-phenyl-N-methyl-1H-pyrazole-4-carboxamide

A solution of 5.6 g of 5-bromo-1-phenyl-N-methyl-1H-pyrazole-4-carboxamide and 2 g of sodium cyanide in 30 ml of DMF was heated at approximately 100° C. for 24 hours. An additional 2 g of sodium cyanide was next added to the reaction mixture which was then heated for an additional 24 hours at 100° C. The solution was poured into ice water and the precipitated solid was collected by filtration. The product thus isolated was recrystallized from 3A ethanol to provide 1.8 g of 5-cyano-1-phenyl-N-methyl-1H-pyrazole-4-carboxamide. MP=203°–204° C.

Analysis calculated for $C_{12}H_{10}N_4O$: Theory: C, 63.71; H, 4.46; N, 24.76; Found: C, 63.43; H, 4.67; N, 24.53.

EXAMPLE 96

5-Cyano-1-(4-ethylphenyl)-N-methyl-1H-pyrazole-4-carboxamide, MP=168°–170° C.

Analysis calculated for $C_{14}H_{14}N_4O$: Theory: C, 66.13; H, 5.55; N, 22.03; Found: C, 65.92; H, 5.60; N, 21.82.

Example 97 represents the modification of existing pyrazolecarboxamides of the invention to the corresponding thiocarboxamide.

EXAMPLE 97

5-Cyano-1-phenyl-N-methyl-1H-pyrazole-4-thiocarboxamide

Eight grams of Lawesson's Reagent was added to a stirring solution of 3 g of 5-cyano-1-phenyl-N-methyl-1H-pyrazole-4-carboxamide in 75 ml of toluene. The reaction mixture was refluxed for approximately 1 hour and the solution was evaporated to dryness. The residue was dissolved in methylene chloride and filtered. The filtrate was concentrated under reduced pressure and the residue was chromatographed employing high pressure liquid chromatography and methylene chloride as the eluent. Fractions containing the second spot were combined and the solvent was evaporated therefrom. The residue was recrystallized from toluene to provide 250 mg of 5-cyano-N-methyl-1-phenyl-1H-pyrazole-4-thiocarboxamide, MP=215°–217° C.

Analysis calculated for $C_{12}H_{10}N_4S$: Theory: C, 59.48; H, 4.16; N, 23.12; Found: C, 59.68; H, 4.21; N, 22.86.

Examples 98–101 illustrate the synthesis of 1-alkyl compounds in accordance with the present invention.

EXAMPLE 98

5-Cyano-1-tert-butyl-N-methyl-1H-pyrazole-4-carboxamide

A. 5-Methyl-1-tert-butyl-1H-pyrazole-4-carboxylic acid, ethyl ester tert-Butylhydrazine hydrochloride (33.6 grams, 0.27 mole) and α-acetyl-α-(dimethylaminomethylene)acetic acid, ethyl ester (50 grams, 0.27 mole) were added to 150 ml of ethanol and the resulting reaction mixture was refluxed for two hours. The reaction mixture was then cooled, and the solvent was removed in vacuo. The residue was taken up in 300 ml of ether, washed with water, washed with saturated sodium bicarbonate, washed with saturated brine, and dried using sodium sulfate and filter paper. The solvent was then removed in vacuo. The residue was distilled at 110° C. at 1.2 mm mercury pressure to provide 49.7 grams of 5-methyl-1-tert-butyl-1H-pyrazole-4-carboxylic acid, ethyl ester. Yield 88.0%.

Analysis calculated for $C_{11}H_{18}N_2O_2$: Theory: C, 62.83; H, 8.63; N, 13.32; Found: C, 62.88; H, 8.86; N, 13.50.

B. 5-(Bromomethyl)-1-tert-butyl-1H-pyrazole-4-carboxylic acid, ethyl ester

5-Methyl-1-tert-butyl-1H-pyrazole-4-carboxylic acid, ethyl ester (30 grams, 0.14 mole) and N-bromosuccinimide (25.4 grams, 0.14 mole) were combined in 100 ml of carbon tetrachloride. A heating lamp was turned onto the reaction mixture, and the reaction mixture was refluxed for three hours. The reaction mixture was then cooled and filtered to remove the succinimide. The filtrate was washed with water, washed with saturated brine, and dried over sodium sulfate and filter paper. The solvent was then removed in vacuo, providing 34.5 grams of the 5-(bromomethyl)-1-tert-butyl-1H-pyrazole-4-carboxylic acid, ethyl ester.

Analysis calculated for $C_{11}H_{17}BrN_2O_2$: Theory: C, 45.69; H, 5.93; N, 9.69; Br, 27.63; Found: C, 45.76; H, 5.65; N, 9.86; Br, 27.56.

C. 5-Formyl-1-tert-butyl-1H-pyrazole-4-carboxylic acid, ethyl ester

This reaction was conducted in accordance with the procedure described by H. B. Hass and M. L. Bender in J. Am. Chem. Soc., 71, 1767 (1949). Sodium (1.6 grams, 0.07 mole) was dissolved in 50 ml of absolute ethanol. Subsequently, 2-nitropropane (8.1 grams, 0.09 mole) and 5-(bromomethyl)-1-tert-butyl-1H-pyrazole-4-carboxylic acid, ethyl ester (20 grams, 0.07 mole) were added. The resulting reaction mixture was refluxed for two hours, then cooled and the solvent removed in vacuo. The residue was taken up in ether, washed with water, washed with 1N sodium hydroxide, washed with saturated brine, and dried using sodium sulfate and filter paper. The solvent was removed in vacuo and the residue was distilled at 110° C. at 1.6 mm mercury pressure, yielding 11 grams of the 5-formyl-1-tert-butyl-1H-pyrazole-4-carboxylic acid, ethyl ester.

Analysis calculated for $C_{11}H_{16}N_2O_3$: Theory: C, 58.91; H, 7.19; N, 12.49; Found: C, 58.78; H, 7.20; N, 12.72.

D. 5-(Hydroxyiminomethyl)-1-tert-butyl-1H-pyrazole-4-carboxamide

Hydroxylamine hydrochloride (4.3 grams, 0.062 mole) was added to a cold solution of 5-formyl-1-tert-butyl-1H-pyrazole-4-carboxylic acid, ethyl ester (7 grams, 0.031 mole) in absolute ethanol (40 ml). The reaction mixture was stirred in the cold for thirty minutes, then at room temperature for 16 hours. The reaction mixture was then poured over ice-water, and the precipitated product was separated, dried, and recrystallized from toluene, yielding 3 grams of 5-(hydroxyiminomethyl)-1-tert-butyl-1H-pyrazole-4-carboxylic acid, ethyl ester, m.p., 105° C.–107° C.

Analysis calculated for $C_{11}H_{16}N_3O_3$: Theory: C, 55.22; H, 7.16; N, 17.56; Found: C, 55.43; H, 7.21; N, 17.65.

E. 5-Cyano-1-tert-butyl-1H-pyrazole-4-carboxylic acid, ethyl ester

Thionyl chloride (6.6 ml, 0.092 mole) was added to a cold solution of 5-(hydroxyiminomethyl)-1-tert-butyl-1H-pyrazole-4-carboxylic acid, ethyl ester (11 grams, 0.046 mole) in 75 ml of ether. The solution was stirred in the cold for thirty minutes, then at room temperature for 16 hours. Water was added to the reaction mixture to neutralize the remaining thionyl chloride, then the reaction mixture was poured into a separatory funnel. The phases were separated and the organic phase was washed with water and dried using sodium sulfate and filter paper. The solvent was removed in vacuo, yielding 8.5 grams of 5-cyano-1-tert-butyl-1H-pyrazole-4-carboxylic acid, ethyl ester.

F. 5-Cyano-1-tert-butyl-1H-pyrazole-4-carboxylic acid

Potassium hydroxide (1.7 grams, 0.027 mole) was dissolved in 20 ml of ethanol. This solution was poured into a refluxing solution of 5-cyano-1-tert-butyl-1H-pyrazole-4-carboxylic acid, ethyl ester, in 50 ml of ethanol. The reaction mixture was heated on a steam bath for five minutes, then poured into ice-water, filtered, and acidified with concentrated hydrochloric acid. The precipitated product was collected and dried, yielding 3.2 grams of 5-cyano-1-tert-butyl-1H-pyrazole-4-carboxylic acid (72% yield).

G.
5-Cyano-1-tert-butyl-N-methyl-1H-pyrazole-4-carboxamide

Carbonyldiimidazole (2.5 grams, 0.015 mole) was added to a solution of 5-cyano-1-tert-butyl-1H-pyrazole-4-carboxylic acid (2.0 grams, 50.01 mole) in DMF. The solution was stirred at room temperature for twenty minutes. Aqueous methylamine (1.5 ml, 0.015 mole) was added and the reaction mixture was stirred at room temperature for 16 hours, then poured into ice-water. The product precipitated and was collected, dried, and recrystallized from ethanol, yielding 1.4 grams of 5-cyano-1-tert-butyl-N-methyl-1H-pyrazole-4-carboxamide, m.p., 164°–166° C.

Analysis calculated for $C_{10}H_{14}N_4O$: Theory: C, 58.24; H, 6.84; N, 27.16; Found: C, 58.43; H, 6.99; N, 27.42.

The following examples 99–101 were prepared in the same procedures as those reported in Example 98.

EXAMPLE 99

5-Cyano-1-tert-butyl-N-cyclopropyl-1L H-pyrazole-4-carboxamide, MP 140°–142° C.

EXAMPLE 100

5-Cyano-1-tert-butyl-N-ethyl-1H-pyrazole-4-carboxamide, MP 122°–124° C.

Analysis calculated for $C_{11}H_{16}N_4O$: Theory: C, 59.98; H, 7.32; N, 25.43; Found: C, 60.17; H, 7.31; N, 25.22.

EXAMPLE 101

5-Cyano-1-tert-butyl-N,N-dimethyl-1H-pyrazole-4-carboxamide, m.p. 93°–95° C.

Analysis calculated for $C_{11}H_{16}N_4O$: Theory: C, 59.98; H, 7.32; N, 25.43; Found: C, 60.20; H, 7.23; N, 25.43.

The compounds of the present invention are useful both as preemergent and postemergent herbicides. Therefore, yet another embodiment of the invention is a method for controlling undesired plants which comprises applying to the plants, or to the locus of the plants, a growth inhibiting amount of a present pyrazole derivative.

The compounds of the present invention display activity against a wide variety of weeds. Examples of typical weeds include, but are not limited to, the following:
Wild Oat (*Avena fatua*)
Catchweed Bedstraw (*Galium aparine*)
Scentless Mayweed (*Matricaria incdora*)
Ladysthumb (*Polygonum persicaria*)
Common Chickweed (*Stellaria media*)
Ivyleaf Speedwell (*Veronica hederaefolia*)
Blackgrass (*Alopecurus myosuroides*)
Chrysanthemum (Chrysanthemum spp.)
Common Purslane (*Portulaca oleracea*)
Sida (Sida spp.)
Bristly Starbur (*Acanthospermum hispidum*)
Goosegrass (*Eleusine indica*)
Smooth Pigweed (*Amaranthus hybridus*)
Alexandergrass (*Brachiaria plantaginea*)
Tall Morningglory (*Ipomoea purpurea*)
Common Lambsquarters (*Chenopodium album*)
Green Smartweed (*Polygonum scabrum*)
Green Foxtail (*Setaria viridis*)
Redroot Pigweed (*Amaranthus retroflexus*)
Wild Buckwheat (*Polygonum convolvulus*)
Brazil Calalilly (*Richardia brasiliensis*)
Natal Grass (*Rhynchelytrum roseum*)
Ryegrass (*Lolium rigidum*)
Kapeweed (*Cryptostemma calendula*)
Purple Loosestrife (*Lythrum salicaria*)
Wild radish (*Raphanus raphanistrum*)
Wireweed (*Polygonum aviculare*)
Henbit (*Laminum amplexicaule*)
Wild Mustard (*Brassica kaber*)
Barnyardgrass (*Echinochloa crus-galli*)
Foxtail Millet (*Setaria italica*)
Velvetleaf (*Abutilon theophrasti*)
Indian Mustard (*Brassica juncea*)
Birdseye Speedwell (*Veronica persica*)
Canada Thistle (*Cirsium arvense*)
Wild Chamomile (*Matricaria chamomilla*)
Annual Bluegrass (*Poa annua*)
Buttercup (Ranunculus spp.)
Field Speedwell (*Veronica agrestis*)
Field Violet (*Viola arvensis*)
Field Pennycress (*Thlaspi arvense*)
Wild Violet (*Viola tricolor*)
Shirley Poppy (*Papaver rhoeas*)
Field Poppy (*Papaver dubium*)
Foolsparsley (*Aethusa cynapium*)
Field Chickweed (*Cerastium arvense*)
Southern Sanbur (*Cenchrus echinatus*)
Large Crabgrass (*Digitaria sanguinalis*)
Cheat (*Bromus secalinus*)
Morningglory (Ipomea spp.)
Common Ragweed (*Ambrosia artemisiifolia*)
Common Milkweed (*Asclepias syriaca*)
Giant Foxtail (*Setaria faberi*)
Common Cocklebur (*Xanthium pensylvanicum*)
Spurred Anoda (*Anoda cristata*)
Sicklepod (*Cassia obtusifolia*)
Yellow Nutsedge (*Cyperus esculentus*)
Jimsonweed (*Datura stramonium*)
Large Crabgrass (*Digitaria sanguinalis*)
Prickly Sida (*Sida spinosa*)
Corn Gromwell (*Lithospermum arvense*)
Yellow Foxtail (*Setaria glauca*)
Tansymustard (*Descurainia pinnata*)
Pepperweed (Lepidium spp.)
Bromegrass (Bromus spp.)
Garden Spurge (*Euphorbia hirta*)
Crowfootgrass (*Dactyloctenium aegyptium*)
Florida Beggarweed (*Desmodium tortuosum*)
Spotted Spurge (*Euphorbia maculata*)
Smallflower Morningglory (*Jacquemontia tamnifolia*)
Browntop Millet (*Panicum ramosum*)
Coast Fiddleneck (*Amsinckia intermedia*)
Wild Turnip (*Brassica campestris*)
Black Mustard (*Brassica nigra*)
Shepherdspurse (*Capsella bursa-pastoris*)
Italian Ryegrass (*Lolium multiflorum*)
London Rocket (*Sisymbrium irio*)
Redmaids Rockpurslane (*Calandrinia caulescens*)
Common Groundsel (*Senecio vulgaris*)
Ivyleaf Morningglory (*Ipomoea hederacea*)
Fall Panicum (*Panicum dichotomiflorum*)
Powell Amaranth (*Amaranthus powellii*)
Texas Panicum (*Panicum texanum*)

Hemp Sesbania (*Sesbania exaltata*)
Annual Sowthistle (*Sonchus oleraceus*)
Field Bindweed (*Convolvulus arvensis*)
Erect Knotweed (*Polygonum erectum*)
Venice Mallow (*Hibiscus trionum*)
Zinnia (*Zinnia elegens*)
Nightshade (Solanum spp.)

The present compounds have also been found safe on a wide variety of desirable plant species, thereby exhibiting their unique selective capacity. Representative examples of relatively tolerant plant species, depending on the concentration of active employed, include the following:
Corn (*Zea mays*)
Wheat (*Triticum aestivum*)
Soybean (*Glycine max*)
Rice (*Oryza sativa*)
Barley (*Hordeum vulgare*)
Cotton (*Gossypium hirsutum*)
Sorghum (*Sorghum vulgare v. saccharatum*)
Sugarcane (*Saccharum officinarum*)
Peanut (*Arachis hypogaea*)
Pea (*Pisum sativum*)
Alfalfa (*Medicago sativa*)
Cucumber (*Cucumis sativus*)
Tomato (*Lycopersicon esculentum*)
Sugar beet (*Beta vulgaris*)
Cabbage (*Brassica oleracea capitata*)

The term "growth inhibiting amount", as defined herein, refers to an amount of a compound of the invention which either kills or stunts the growth of the weed species for which control is desired. This amount will generally be from about 0.05 to about 20.0 pounds or greater of a compound of the invention per acre (about 0.056 to about 22.4 kg/ha). The compounds are more preferably applied at rates of about 0.10 to about 8.0 pounds per acre (about 0.112 to about 8.96 kg/ha). The exact concentration of active ingredient required varies with the weed species to be controlled, type of formulation, soil type, climate conditions and the like.

The term "undesired plants", as defined herein, refers to both weeds and weed seeds which are present at the location to be treated with a compound of the invention. These compounds can be applied to the soil to selectively control undesired plants by soil contact when the weed seeds are germinating and emerging. They can also be used directly to kill emerged weeds by direct contact with the exposed portion of the weed.

The compounds of the present invention are preferably formulated with a suitable agriculturally-acceptable carrier for ease of application. Such compositions will contain from about 0.1 to about 95.0 percent by weight of the active ingredient, depending on the composition desired. Examples of typical herbicidal compositions contemplated as another aspect of the present invention include sprayable formulations, such as wettable powders, aqueous suspensions and emulsifiable concentrates; and solid compositions, such as dusts and granules.

The most convenient formulations are in the form of concentrated compositions to be applied by spraying as water dispersions or emulsions containing in the range from about 0.1 percent to about 10 percent of the active agent by weight. Water-dispersible or emulsifiable compositions may be either solids, usually known as wettable powders, or liquids, usually known as emulsifiable concentrates and aqueous suspensions.

A typical wettable powder comprises an intimate mixture of an active ingredient of the invention, an inert carrier, and one or more surfactants. The concentration of the active agent is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed naphthalenesulfonates, and the alkyl sulfates.

A typical emulsifiable concentrate comprises from about 0.1 to about 6 pounds of a compound of the invention per gallon of liquid (about 0.0112 to about 0.672 kg/l), dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as alkylphenol adducts of polyoxyethylene, and are used at similar percentages as for wettable powders.

An aqueous suspension, or flowable, is comprised of a finely ground suspension of the active ingredient dispersed in a water based system. This type of formulation is particularly useful for compounds with low water solubility. The concentration of active agent is usually from about 15 to 60 percent by weight. A typical aqueous suspension may comprise wetting and dispersing agents, antifreeze components, thickening or bulking agents, as well as water and the active ingredient.

Dust compositions containing a compound of the present invention usually contain from about 0.1 to about 10 percent by weight of the compound. Dusts are prepared by intimately mixing and finely grinding the active agent with an inert solid such as ground montmorillonite clay, attapulgite clay, talc, ground volcanic rock, kaolin clay, or other inert, relatively dense, inexpensive substances.

Solid, granular compositions are convenient for the application of compounds of this invention to the soil and will contain the active agent in an amount from about 0.1 to about 20 percent by weight. Granules comprise a compound of the invention dispersed on a granular inert carrier such as coarsely ground clay of from about 0.1 to about 3 mm particle size. The active ingredient is most conveniently applied to the clay by dissolving it in an inexpensive solvent, such as acetone, and applying the solution to the sized clay in an appropriate solids mixer. The solvent is then typically removed by evaporation prior to applying the granules to the application site.

When operating in accordance with the present invention, the present compounds or compositions thereof, may be applied to the site where herbicidal or algicidal control is desired by any convenient manner, e.g., by means of hand dusters or sprayers. Metering applicators can apply accurately measured quantities of granular compositions to the locus to be treated. Other applications can be carried out with power dusters, boom sprayers, high-pressure sprayers and spray dusters. In large scale operations, dusts or low-volume sprays can be applied aerially, for example from airplanes or helicopters, to the application site. When applying the formulations described above, it is important to apply the desired concentration of active ingredient uniformly to the plants or locus to be treated.

The performance of the compounds of the present invention suggests that their preferred utilization will be as herbicides on grass crops, especially wheat, corn, and possibly sorghum. The compounds exhibit activity against both grass and broadleaf weed species, but exhibit greater activity against broadleaf species. The preferred application time is preemergent, that is, following planting of the crop but prior to its emergence. However, the compounds also exhibit modest activity against weeds, with adequate crop safety, when applied early postemergence, that is, shortly after crop and weed emergence.

The following examples provide an illustration of typical agriculturally-acceptable compositions comprehended by this invention.

| Wettable Powder | |
|---|---|
| Ingredient | Concentration by Weight (Percent) |
| 5-Cyano-1-phenyl-N—methyl-1H—pyrazole-4-carboxamide | 50.0 |
| Igepal, a nonionic wetting agent, GAF Corporation | 5.0 |
| Polyfon O, lignosulfonate dispersant, Westvaco Corporation | 5.0 |
| Zeolex 7, a precipitated hydrated silica bulking agent, J. M. Huber Corporation | 5.0 |
| Barden Clay, a kaolinite clay, J. M. Huber Corporation | 35.0 |
| | 100.0 |

The ingredients are combined and finely ground to provide a free-flowing powder that can be suspended in water for convenient spray application.

| Aqueous Suspension | |
|---|---|
| Ingredient | Concentration by Weight (Percent) |
| 5-Cyano-1-phenyl-N—cyclopropyl-1H—pyrazole-4-carboxamide | 45.0 |
| Polyfon H, an anionioc lignosulfonate wetting agent and dispersant, Westvaco Corporation | 3.0 |
| Sponto 2174, an emulsifier, Witco Chemical Corporation | 4.0 |
| Ethylene Glycol | 8.0 |
| Xanthum Gum thickening agent | 0.2 |
| Antifoam C foam suppressant, Dow Corning Corporation | 0.5 |
| Water | 39.3 |
| | 100.0 |

The above ingredients are intimately admixed and finely ground to provide a suitable suspension, which is then further diluted with water at the application site.

| Dust | |
|---|---|
| Ingredient | Concentration by Weight (Percent) |
| 5-Cyano-1-(4-chlorophenyl)-N—methyl-N-ethyl-1H—pyrazole-4-carboxamide | 10.0 |
| Diatomite, a diatomaceous earth, Witco Chemical Corporation, Inorganic Specialties Division | 90.0 |
| | 100.0 |

The active ingredient and diatomaceous earth are intimately mixed and ground to a fine powder of uniform particle size of about 16 to about 40 microns. The dust thus formed may be applied by any number of conventional methods, for example by an aerial application.

| Granules | |
|---|---|
| Ingredient | Concentration by Weight (Percent) |
| 5-Cyano-1-(2-pyridinyl)-N—methyl-1H—pyrazole-4-carboxamide | 5.0 |
| Heavy aromatic naphtha | 5.0 |
| Bentonite 20/40 mesh granular clay, The Floridin Company | 90.0 |
| | 100.0 |

The compound is dissolved in the naphtha and sprayed onto the clay granules, typically under agitation, and the formulation granules are sieved to provide a uniform mesh size.

The herbicidal activity of representative compounds of the present invention is illustrated by the following experiments.

EXPERIMENT 1

The initial screen used to evaluate herbicidal efficacy, was conducted at a test compound concentration of 15 lbs/acre (16.8 kg/ha). In this test a standard sand:soil mixture (1:1) was added to separate containers and tomato, large crabgrass and pigweed seeds were planted by row. Each container was then fertilized before treatment.

The test compounds were formulated for application by dissolving the compound into a solvent prepared by combining Toximul R and Toximul S (proprietary blends of anionic and nonionic surfactants manufactured by Stepan Chemical Company, Northfield, Ill.) with a 1:1 (v/v) mixture of acetone:ethanol. The solvent/compound solution was diluted with deionized water and applied postemergence to some planted containers and preemergence to others using a DeVilbiss atomizer. Postemergence treatment was made 11 to 13 days after planting while preemergence treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. Also, the various types of injury of each test species were coded as follows:

A = abscission of leaves
B = burned
C = chlorosis
D = death
E = epinasty

F=formation effects
G=dark green
I=increased plant growth
L=local necrosis
N=no germination
P=purple pigmentation
R=reduced germination
S=stunting
U=unclassified injury Table I presents the herbicidal activity of typical 5-cyano-4-pyrazolecarboxamide derivatives of the invention when evaluated in the screen described above.

TABLE I

| | Herbicide Pretest at 15 lbs/acre (16.8 kg/ha) | | | | | |
|---|---|---|---|---|---|---|
| | Preemergence | | | Postemergence | | |
| Example No. of Compound Tested | Tomato | Large Crab-grass | Pig-weed | Tomato | Large Crab-grass | Pig-weed |
| 1 | 2CS | 2S | 3RS | 5D | 5D | 5D |
| 3 | 3CS | 3S | 3RS | 5D | 5D | 5D |
| 4 | 5D | 4BS | 4BS | 5D | 5D | 5D |
| 6 | 2CS | 1 | 3RS | 5D | 5D | 5D |
| 7 | 1 | 1 | 3S | 3CS | 1 | 1 |
| 9 | 1 | 1 | 2S | 3BS | 4BS | 4BS |
| 11 | 4BS | 2S | 4RS | 5D | 5D | 5D |
| 15 | 3CS | 4S | 3S | 5D | 5D | 5D |
| 16 | 1 | 1 | 3S | 5D | 4BCS | 2C |
| 18 | 1 | 1 | 1 | 1 | 1 | 1 |
| 21 | 1 | 1 | 3RS | 4BS | 4BS | 4BS |
| 22 | 1 | 1 | 4RS | 2B | 1 | 2B |
| 23 | 1 | 1 | 1 | 1 | 2C | 1 |
| 24 | 2CS | 2RS | 3RS | 5D | 5D | 5D |
| 25 | 4BS | 1 | 4BS | 5D | 5D | 5D |
| 26 | 1 | 1 | 1 | 2S | 4BS | 4BS |
| 27 | 4BS | 4S | 3RS | 5D | 4BS | 3BS |
| 28 | 1 | 2S | 4RS | 4BS | 2FS | 4BS |
| 29 | 1 | 1 | 1 | 2S | 1 | 1 |
| 30 | 1 | 2S | 3RS | 5D | 2BS | 4BS |
| 31 | 1 | 2S | 3RS | 4BS | 4BS | 4BS |
| 32 | 3RS | 4S | 4BS | 4BS | 4BS | 3BS |
| 36 | 5D | 2B | 4BS | 5D | 5D | 3BS |
| 37 | 1 | 2S | 3RS | 5D | 2BCS | 1 |

TABLE I-continued

| | Herbicide Pretest at 15 lbs/acre (16.8 kg/ha) | | | | | |
|---|---|---|---|---|---|---|
| | Preemergence | | | Postemergence | | |
| Example No. of Compound Tested | Tomato | Large Crab-grass | Pig-weed | Tomato | Large Crab-grass | Pig-weed |
| 40 | 3S | 4RS | 4RS | 5D | 5D | 5D |
| 41 | 2C | 2S | 4RS | 5D | 5D | 5D |
| 42 | 5N | 4RS | 4RS | 5D | 5D | 5D |
| 47 | 2CS | 2S | 3RS | 5D | 4BS | 5D |
| 53 | 3S | 1 | 3RS | 4BS | 3BS | 2B |
| 61 | 2CS | 1 | 4RS | 5D | 5D | 5D |
| 62 | 1 | 2S | 4RS | 5D | 5D | 5D |
| 63 | 1 | 1 | 3RS | 5D | 5D | 5D |
| 65 | 2CS | 2S | 2C | 5D | 5D | 5D |
| 66 | 1 | 2S | 3RS | 5D | 4BS | 3BS |
| 67 | 1 | 1 | 1 | 1 | 1 | 1 |
| 70 | 1 | 1 | 4RS | 4BS | 5D | 3BS |
| 71 | 1 | 1 | 1 | 5D | 4BS | 5D |
| 77 | 5N | 2RS | 4RS | 5D | 5D | 5D |
| 79 | 3CS | 3FS | 4RS | 5D | 5D | 5D |
| 80 | 5N | 2S | 2S | 1 | 1 | 1 |
| 81 | 4BS | 4CS | 5D | 5D | 5D | 5D |
| 82 | 1 | 2S | 2S | 2S | 1 | 1 |
| 83 | 1 | 1 | 1 | 3BS | 1 | 1 |
| 84 | 1 | 1 | 1 | 2S | 2S | 2BS |
| 85 | 1 | 1 | 2RS | 5D | 5D | 5D |
| 86 | 4BS | 1 | 5D | 5D | 5D | 5D |
| 87 | 1 | 1 | 3RS | 5D | 5D | 5D |
| 88 | 1 | 1 | 3RS | 5D | 5D | 5D |
| 89 | 4CS | 3S | 5N | 5D | 5D | 5D |
| 90 | 5N | 3BS | 5N | 5D | 5D | 5D |
| 91 | 2CS | 2S | 3RS | 5D | 5D | 5D |

EXPERIMENT 2

The herbicidal activity of some of the compounds of the present invention was further evaluated at various application rates in a multiple species greenhouse test. Several additional weed and crop species were utilized to determine the herbicidal activity and selectivity of the test compounds. Lower concentrations of the test compounds were obtained by serial dilution of the above described formulation with a mixture of the surfactant containing solvent and deionized water. The compounds were evaluated according to the general procedure outlined above. Table II presents the preemergence herbicidal test results, while Table III presents postemergence test data, both applications being administered at 8 lbs/acre (8.96 kg/ha) or less.

TABLE II

Preemergence

| Example No. of Compound Tested | Rate of Appln. lbs/acre (kg/ha) | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
|---|---|---|---|---|---|---|---|---|---|---|---|---|---|---|---|---|---|---|---|---|---|
| 65 | 8.0 (8.96) | 1 | — | — | — | 4 | 3 | — | 2 | 4 | 3 | — | 4 | 2 | 4 | 3 | — | 3 | — | — | 3 |
|  | 4.0 (4.48) | 1 | 1 | 2 | 2 | 4 | 3 | 1 | 2 | 2 | 2 | 5 | 4 | 4 | 5 | 3 | 3 | 5 | 3 | 2 | 5 |
|  | 2.0 (2.24) | 1 | 1 | 2 | — | 3 | 2 | 3 | 2 | 1 | 2 | 5 | 3 | 4 | 4 | 2 | 2 | 4 | 2 | 1 | 1 |
|  | 1.0 (1.12) | 1 | 1 | 1 | 1 | 2 | 3 | 1 | 2 | — | 1 | 4 | 3 | 2 | 4 | 1 | 1 | 2 | 2 | — | 2 |
|  | 1.0 (1.12) | 1 | 1 | 1 | 1 | 2 | 4 | 2 | 2 | — | 1 | — | 3 | 3 | 4 | 4 | — | 4 | 2 | 2 | 3 |
|  | 0.5 (0.56) | 1 | — | 1 | 1 | 1 | 1 | 1 | — | — | — | — | — | — | 3 | 3 | — | 2 | — | — | 2 |
|  | 0.25 (0.28) | 1 | — | 1 | 1 | 1 | 1 | 1 | 1 | — | — | 1 | — | — | 3 | 2 | — | 2 | — | — | 2 |
| 63 | 8.0 (8.96) | 2 | 4 | 3 | 3 | 5 | 4 | 1 | 5 | 5 | 4 | 5 | 4 | 4 | 5 | 5 | 4 | 5 | 5 | 4 | 5 |
|  | 4.0 (4.48) | 1 | 1 | 1 | 1 | 5 | 4 | 1 | 5 | 4 | 3 | 5 | 4 | 3 | 5 | 5 | 2 | 5 | 3 | 2 | 5 |
|  | 2.0 (2.24) | 1 | 1 | 1 | 1 | 3 | 1 | 1 | 2 | 3 | 2 | 3 | 1 | 2 | 3 | 3 | 1 | 3 | — | 2 | 3 |
|  | 1.0 (1.12) | 1 | 1 | 1 | 1 | 3 | 4 | — | 1 | — | 1 | 3 | 4 | 3 | 3 | 3 | 1 | 4 | 2 | 3 | 3 |
|  | 1.0 (1.12) | 1 | 1 | 1 | 1 | 2 | 3 | 2 | 2 | 2 | — | 3 | 3 | 2 | 2 | 3 | 1 | 3 | — | 2 | 3 |
|  | 0.5 (0.56) | 1 | 1 | 1 | 1 | 1 | 1 | 2 | — | — | 1 | 2 | 2 | 1 | 2 | 2 | — | 2 | — | 1 | 2 |
|  | 0.25 (0.28) | 1 | — | 1 | 1 | 1 | — | 2 | 2 | — | — | 1 | — | — | 2 | 1 | — | 2 | — | 1 | 1 |
| 62 | 8.0 (8.96) | 2 | 1 | 2 | 1 | 2 | 2 | 1 | 2 | 2 | 2 | 4 | 4 | 2 | 3 | 3 | 2 | 4 | 2 | 2 | 2 |
|  | 4.0 (4.48) | 1 | 2 | 2 | 1 | 1 | 3 | 1 | 2 | 2 | 1 | 2 | 5 | 3 | 2 | 2 | 2 | 4 | 1 | 2 | 2 |
|  | 2.0 (2.24) | — | 1 | 1 | 1 | 1 | 2 | 1 | 1 | — | — | 2 | 4 | 3 | 2 | 3 | 1 | 3 | — | 1 | 3 |
|  | 1.0 (1.12) | 1 | 1 | 1 | — | 1 | 2 | 2 | 1 | — | — | 1 | 3 | 2 | 4 | 3 | 1 | 2 | — | 2 | 3 |
|  | 1.0 (1.12) | 1 | 1 | 1 | — | 1 | 2 | 2 | 1 | — | — | — | 3 | 3 | 3 | 2 | — | 2 | — | 2 | 3 |
|  | 0.5 (0.56) | 1 | 1 | 1 | 1 | 1 | 2 | 2 | 1 | — | — | — | 2 | 2 | 2 | 2 | 1 | 2 | — | 2 | 2 |
|  | 0.25 (0.28) | 1 | 2 | — | — | — | 2 | 2 | — | 2 | 2 | 2 | — | — | — | 2 | 1 | — | — | 1 | 3 |
| 14 | 8.0 (8.96) | 1 | — | 2 | — | 2 | 3 | 2 | 3 | 3 | 2 | — | 4 | 4 | 4 | 4 | 2 | 4 | 2 | 2 | 3 |
|  | 4.0 (4.48) | 1 | — | 1 | — | 2 | 3 | 2 | 2 | 2 | — | — | 1 | 3 | 2 | 3 | 2 | 3 | — | 2 | 3 |
|  | 2.0 (2.24) | 1 | — | — | — | 1 | 2 | — | 1 | — | — | — | — | 2 | 2 | 2 | 1 | 2 | — | — | 2 |
|  | 1.0 (1.12) | 1 | — | — | — | 1 | 1 | — | — | — | — | 1 | — | — | 2 | 2 | 1 | 2 | 1 | — | 2 |
| 23 | 8.0 (8.96) | 2 | 2 | 2 | — | 2 | 3 | 2 | 3 | 4 | 4 | 4 | 5 | 5 | 4 | 5 | 5 | 4 | 5 | 4 | 5 |
| 61 | 8.0 (8.96) | 1 | 2 | 1 | 1 | 5 | 3 | 2 | 4 | 5 | 1 | 4 | 4 | 3 | 4 | 4 | 3 | 4 | 4 | 3 | 4 |
|  | 4.0 (4.48) | 1 | 2 | 2 | 1 | 3 | 2 | 2 | 1 | 4 | 1 | 4 | 4 | 3 | 4 | 3 | 3 | 3 | 3 | 3 | 4 |
|  | 2.0 (2.24) | 1 | 2 | 2 | 1 | 2 | 3 | 1 | 3 | 3 | — | 2 | 3 | 2 | 3 | 3 | 2 | 3 | — | 2 | 4 |
|  | 1.0 (1.12) | 2 | 2 | 2 | 1 | 2 | 2 | 1 | 2 | 3 | 2 | 3 | 3 | 3 | 2 | 3 | 2 | 2 | 4 | 3 | 2 |
|  | 1.0 (1.12) | 2 | 2 | 2 | 1 | 1 | 2 | 2 | 1 | 3 | 2 | 2 | 2 | 2 | 2 | 3 | 2 | 3 | 2 | 2 | 4 |
|  | 0.5 (0.56) | 2 | 2 | 2 | 1 | 2 | 2 | 2 | — | — | 1 | 1 | 1 | 2 | 2 | 2 | 2 | 2 | 1 | 2 | 2 |
|  | 0.25 (0.28) | 1 | 1 | — | — | 1 | 1 | 2 | — | — | — | — | — | — | — | 3 | — | 1 | — | — | 4 |
| 11 | 8.0 (8.96) | 2 | 2 | 2 | 2 | 4 | 3 | 2 | 5 | 5 | 4 | 4 | 5 | 4 | 4 | 5 | 5 | 5 | 5 | 5 | 5 |
|  | 4.0 (4.48) | 2 | 2 | 1 | 1 | 3 | 3 | 2 | 4 | 4 | 4 | 2 | 4 | 3 | 3 | 4 | 4 | 3 | 4 | 3 | 2 |
|  | 2.0 (2.24) | 1 | 1 | 2 | 1 | 2 | 2 | 2 | 3 | 3 | 2 | 2 | 3 | 2 | 3 | 3 | 3 | 3 | 3 | 2 | 3 |
|  | 1.0 (1.12) | 2 | 3 | 2 | 1 | 4 | 3 | 1 | 3 | 2 | 2 | 3 | 4 | 3 | 3 | 3 | 2 | 3 | — | 2 | 3 |
|  | 1.0 (1.12) | 2 | 2 | 2 | 1 | 2 | 3 | — | 2 | 2 | 2 | 2 | 3 | 2 | 3 | 3 | 2 | 3 | — | 2 | 3 |
|  | 0.5 (0.56) | 2 | 2 | 2 | 1 | 2 | 2 | 2 | 1 | 1 | 1 | 1 | 2 | 2 | 2 | 2 | 2 | 2 | 1 | 2 | 2 |
|  | 0.25 (0.28) | 1 | 1 | — | — | 1 | — | 1 | — | — | — | — | — | — | — | 1 | — | 2 | — | 1 | 1 |
| 42 | 8.0 (8.96) | 1 | 1 | 2 | 1 | 3 | 3 | 1 | 2 | 5 | 1 | 4 | 4 | 4 | 4 | 5 | 4 | 5 | 4 | 4 | 5 |
|  | 4.0 (4.48) | 1 | 1 | 2 | 1 | 1 | 5 | 2 | 3 | 4 | 1 | 5 | 5 | 4 | 3 | 4 | 4 | 4 | 3 | 2 | 2 |
|  | 2.0 (2.24) | 2 | — | 2 | 1 | — | 4 | 1 | — | 2 | — | 2 | 5 | 4 | 3 | 4 | 4 | 5 | 1 | 2 | 3 |
|  | 1.0 (1.12) | 1 | 2 | 2 | 1 | 4 | 4 | 1 | 3 | 2 | — | 2 | 4 | 4 | 3 | 4 | 2 | 5 | 4 | 3 | 4 |
|  | 1.0 (1.12) | 1 | 2 | 2 | 1 | 2 | 4 | — | 2 | 2 | 2 | 2 | 4 | 3 | 3 | 4 | 4 | 5 | 3 | 2 | 4 |
|  | 0.5 (0.56) | 1 | 2 | 2 | 1 | 4 | 4 | 2 | 3 | 2 | 1 | 4 | 5 | 3 | 3 | 4 | 2 | 4 | 4 | 2 | 2 |
|  | 0.25 (0.28) | 1 | 1 | 1 | 1 | 2 | 2 | 2 | — | 1 | — | 2 | 4 | 2 | 1 | 3 | 1 | 2 | — | 1 | 2 |

TABLE II-continued

| | | Crops | | | | | | | | | Preemergence Weeds | | | | | | | | | | |
|---|---|---|---|---|---|---|---|---|---|---|---|---|---|---|---|---|---|---|---|---|---|
| Example No. of Compound Tested | Rate of Appln. lbs/acre (kg/ha) | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
| 44 | 8.0 (8.96) | 1 | 1 | 2 | 3 | 5 | 4 | 3 | 5 | 5 | 4 | 5 | 5 | 4 | 5 | 5 | 4 | 5 | 3 | 4 | 5 |
| | 4.0 (4.48) | 1 | 1 | 2 | 2 | 5 | 5 | 2 | 5 | 5 | 4 | 4 | 4 | 4 | 5 | 5 | 4 | 4 | 5 | 5 | 5 |
| | 2.0 (2.24) | 1 | 1 | 1 | 1 | 3 | 4 | 2 | 2 | 4 | 3 | 4 | 4 | 3 | 5 | 4 | 2 | 4 | 3 | 2 | 3 |
| | 1.0 (1.12) | 1 | 1 | 2 | 2 | 5 | 5 | 2 | 5 | 4 | 3 | 5 | 3 | 3 | 5 | 4 | 2 | 4 | 4 | 5 | 3 |
| | 1.0 (1.12) | 1 | 1 | 2 | 1 | 2 | 4 | 1 | 2 | 2 | 2 | 5 | 3 | 3 | 4 | 4 | 2 | 4 | 3 | 4 | 4 |
| | 0.5 (0.56) | 1 | 2 | 2 | 1 | 2 | 2 | 2 | 2 | 3 | 1 | 4 | 3 | 3 | 3 | 3 | 1 | 3 | 1 | 3 | 3 |
| | 0.25 (0.28) | 1 | 1 | 2 | 1 | 2 | 2 | 1 | 1 | 2 | 1 | 3 | 2 | 2 | 3 | 2 | 1 | 2 | 2 | 3 | 2 |
| | 0.25 (0.28) | 1 | 1 | 1 | 1 | 2 | 2 | 2 | 1 | 1 | 1 | 2 | 2 | 3 | 2 | 2 | 1 | 2 | 2 | 3 | 1 |
| | 0.125 (0.14) | 1 | — | 1 | 1 | 1 | 1 | — | — | 1 | — | — | 2 | 1 | 2 | 2 | 1 | 1 | 1 | 1 | 1 |
| | 0.0625 (0.07) | 1 | — | — | — | 1 | — | — | — | — | — | — | — | — | 1 | — | — | — | — | — | — |
| 96 | 8.0 (8.96) | 2 | 1 | 1 | 1 | 2 | 2 | 1 | 2 | 3 | — | 2 | 4 | 2 | 4 | 4 | 3 | 5 | 3 | 4 | 3 |
| | 4.0 (4.48) | 1 | 1 | 1 | 1 | 1 | 1 | — | 1 | 2 | 1 | 3 | 3 | 2 | 4 | 4 | 1 | 2 | 1 | 1 | 2 |
| | 2.0 (2.24) | 1 | 1 | 1 | 1 | 1 | 2 | — | 1 | 1 | 1 | 3 | 2 | 2 | 3 | 3 | 3 | 2 | — | 2 | 2 |
| | 1.0 (1.12) | 1 | — | 1 | 1 | 1 | 3 | — | 1 | — | — | 1 | 2 | 2 | 2 | 1 | 1 | 2 | — | — | 1 |
| | 1.0 (1.12) | 1 | 2 | 1 | 1 | 2 | 3 | 1 | 2 | 2 | 3 | 5 | 3 | 3 | 5 | 4 | 2 | 2 | 2 | 2 | 2 |
| | 0.5 (0.56) | 1 | 1 | 1 | 1 | 3 | 2 | 1 | 1 | 1 | 1 | 4 | 2 | 2 | 3 | 3 | 1 | 2 | — | 2 | 2 |
| | 0.25 (0.28) | 1 | — | 1 | — | 2 | 1 | — | 1 | — | 1 | 3 | 2 | — | 3 | 2 | — | 2 | — | — | 1 |
| 58 | 8.0 (8.96) | — | — | — | — | — | — | — | — | — | — | — | — | — | 2 | — | — | 2 | — | — | 5 |
| | 4.0 (4.48) | — | — | 1 | — | 1 | — | 1 | — | 4 | 2 | 3 | 4 | 4 | 5 | 5 | 2 | 4 | — | 4 | 4 |
| | 2.0 (2.24) | — | — | 1 | — | 1 | — | — | 1 | 2 | 1 | 3 | 3 | 2 | 5 | 3 | 2 | 2 | — | 3 | 3 |
| | 1.0 (1.12) | 1 | 1 | 1 | — | 1 | — | 1 | 1 | 1 | 1 | 3 | 2 | 2 | 3 | 1 | 2 | 2 | — | 2 | 2 |
| | 0.25 (0.28) | — | — | — | — | — | — | — | — | — | — | — | — | — | — | — | — | — | — | — | 1 |
| 43 | 8.0 (8.96) | 2 | 3 | 3 | 2 | 4 | 3 | 2 | 3 | 5 | 5 | 5 | 5 | 4 | 5 | 5 | 4 | 5 | 4 | 4 | 4 |
| | 4.0 (4.48) | 1 | 1 | 2 | 2 | 3 | 2 | 1 | 3 | 2 | 2 | 4 | 4 | 3 | 5 | 5 | 3 | 5 | 2 | 4 | 3 |
| | 2.0 (2.24) | 1 | 1 | 2 | 1 | 4 | 3 | — | 3 | 2 | 3 | 3 | 3 | 2 | 5 | 5 | 2 | 3 | 2 | 3 | 3 |
| | 1.0 (1.12) | 1 | 3 | 3 | 2 | 3 | 4 | 2 | 5 | 4 | 2 | 5 | 4 | 3 | 5 | 5 | 2 | 4 | 3 | 3 | 5 |
| | 0.5 (0.56) | 1 | 3 | 2 | — | 2 | 4 | 1 | 3 | 3 | 1 | 4 | 3 | 2 | 5 | 4 | 2 | 3 | 5 | 4 | 3 |
| | 0.25 (0.28) | 1 | 1 | 1 | 1 | 2 | 2 | — | 2 | 1 | — | — | 2 | 1 | 3 | 3 | 1 | 1 | 1 | 3 | 3 |
| 68 | 8.0 (8.96) | 2 | 1 | 1 | 1 | 1 | 1 | 2 | 1 | 5 | 2 | 4 | 4 | 2 | 5 | 4 | 2 | 4 | 4 | 4 | 5 |
| | 4.0 (4.48) | 1 | 1 | 1 | 1 | 1 | 1 | 1 | 1 | 3 | 1 | 4 | 3 | 3 | 5 | 4 | 2 | 4 | 5 | 3 | 2 |
| | 2.0 (2.24) | 1 | 1 | 1 | 1 | 1 | 1 | — | — | 1 | 1 | 4 | 3 | 2 | 5 | 3 | 2 | 2 | 2 | 2 | 1 |
| | 1.0 (1.12) | 1 | 1 | 1 | 1 | 1 | 1 | 1 | 1 | 1 | 1 | 3 | 2 | 2 | 4 | 3 | 1 | 2 | 1 | 2 | 1 |
| | 1.0 (1.12) | 1 | 1 | 1 | 1 | 2 | 3 | 2 | 2 | 2 | 2 | 4 | 4 | 3 | 5 | 3 | 1 | 3 | — | 1 | 2 |
| | 0.5 (0.56) | — | — | — | 1 | 1 | 1 | 1 | — | 1 | — | 3 | 2 | 2 | 4 | 2 | 1 | 2 | — | 1 | 1 |
| | 0.25 (0.28) | — | — | 1 | — | 1 | 1 | — | — | — | — | 2 | 1 | — | 4 | 2 | — | 2 | — | — | — |
| 28 | 8.0 (8.96) | — | — | 1 | 1 | 2 | 3 | — | — | — | 2 | 4 | 4 | 4 | 5 | 5 | 3 | 5 | 4 | 3 | 3 |
| | 4.0 (4.48) | — | — | 1 | 1 | 2 | 2 | 2 | 4 | 4 | 2 | 4 | 3 | 3 | 5 | 4 | 3 | 4 | 2 | 1 | 5 |
| | 2.0 (2.24) | — | — | 1 | 1 | 1 | 1 | 1 | 2 | 2 | 1 | 4 | 2 | 2 | 5 | 3 | 1 | 3 | 1 | — | 5 |
| | 1.0 (1.12) | 1 | 1 | 1 | 1 | 1 | 1 | — | 1 | 1 | 1 | 3 | 2 | 2 | 4 | 3 | — | 2 | 1 | — | 2 |
| | 1.0 (1.12) | 1 | 1 | 1 | 1 | 2 | 1 | 1 | 5 | 4 | 4 | 4 | 5 | 3 | 5 | 5 | 4 | 5 | 4 | 3 | 4 |
| | 0.5 (0.56) | 1 | 1 | 1 | — | 1 | 1 | — | 2 | 5 | 5 | 4 | 3 | 3 | 4 | 4 | 4 | 4 | 3 | 1 | 1 |
| | 0.25 (0.28) | — | — | — | — | 1 | — | — | 2 | 4 | 3 | 3 | 3 | 3 | 4 | 3 | 1 | 3 | 2 | 2 | 1 |
| 19 | 8.0 (8.96) | 3 | 4 | 2 | 3 | 4 | 4 | 2 | 5 | — | 4 | 4 | 5 | 4 | 5 | 5 | 4 | 4 | 3 | 4 | 4 |
| | 4.0 (4.48) | 3 | 4 | 1 | 2 | 2 | 3 | — | 2 | 5 | 5 | 4 | 3 | 3 | 5 | 4 | 4 | 2 | 2 | 4 | 3 |
| | 2.0 (2.24) | 1 | 2 | 1 | 2 | 2 | 2 | 1 | 2 | 4 | 2 | 4 | 3 | 3 | 4 | 3 | 1 | 2 | 2 | 3 | 2 |
| | 1.0 (1.12) | 1 | 2 | 2 | 2 | 5 | 4 | 1 | 3 | 3 | 1 | 4 | 3 | 3 | 4 | 3 | 2 | 5 | 2 | 3 | 2 |
| | 1.0 (1.12) | 1 | 1 | 2 | — | 1 | — | — | — | 3 | — | — | — | — | 4 | 3 | 2 | 5 | 2 | 4 | 4 |

TABLE II-continued

| Example No. of Compound Tested | Rate of Appln. lbs/acre (kg/ha) | Premergence Crops | | | | | | | | | Weeds | | | | | | | | | | |
|---|---|---|---|---|---|---|---|---|---|---|---|---|---|---|---|---|---|---|---|---|---|
| | | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
| | 0.5 (0.56) | 1 | 1 | 1 | 1 | | 2 | 1 | 2 | 1 | 1 | 4 | 2 | 4 | 3 | 3 | 2 | 4 | 1 | 4 | 4 |
| | 0.25 (0.28) | 1 | 1 | 1 | 1 | | 1 | 1 | | 1 | | 3 | 2 | 3 | 3 | 3 | 1 | 3 | 1 | 2 | 1 |
| 67 | 8.0 (8.96) | 2 | 2 | 1 | | 2 | 3 | 1 | 3 | 5 | 4 | 5 | 4 | 5 | 5 | 5 | 3 | 5 | 5 | 5 | 5 |
| | 4.0 (4.48) | 2 | 2 | 1 | 1 | 1 | 4 | 1 | 3 | 3 | 3 | 4 | 4 | 3 | 5 | 4 | 2 | 4 | 3 | 3 | 4 |
| | 2.0 (2.24) | 1 | 1 | 1 | 1 | 2 | 2 | 1 | 3 | 4 | 2 | 2 | 2 | 2 | 4 | 4 | 2 | 4 | 2 | 2 | 2 |
| | 1.0 (1.12) | 1 | 1 | 2 | 1 | 1 | 2 | 1 | 3 | 2 | 1 | 2 | 2 | 2 | 4 | 4 | 1 | 2 | 3 | 2 | 3 |
| | 1.0 (1.12) | 1 | 1 | 1 | 1 | 2 | 2 | 1 | 2 | 2 | 1 | 3 | 2 | 2 | 4 | 3 | 2 | 3 | 4 | 3 | 2 |
| | 0.5 (0.56) | 1 | 1 | 1 | 1 | 1 | 1 | 1 | 1 | 1 | 1 | 1 | 2 | 1 | 2 | 3 | 1 | 2 | 2 | 2 | 2 |
| | 0.25 (0.28) | | | | | | | | | | | | 2 | | 1 | 1 | 1 | | 1 | | | |
| 73 | 8.0 (8.96) | 1 | 1 | | | 1 | 2 | 1 | 2 | 5 | 4 | 4 | 4 | 5 | 5 | 4 | 3 | 5 | 4 | 5 | 5 |
| | 4.0 (4.48) | 1 | 1 | 1 | 1 | 1 | 1 | 1 | 1 | 2 | 2 | 2 | 3 | 2 | 4 | 3 | 2 | 3 | 2 | 3 | 4 |
| | 2.0 (2.28) | | | 1 | 1 | 1 | 1 | 1 | 1 | | 1 | 1 | 2 | 2 | 2 | 3 | 1 | 2 | 2 | 3 | 2 |
| | 1.0 (1.12) | 1 | 2 | 2 | 2 | 5 | 3 | 2 | 4 | 2 | 2 | 3 | 4 | 5 | 5 | 4 | 2 | 5 | 2 | 4 | 2 |
| | 1.0 (1.12) | 1 | 1 | 3 | 1 | 2 | 2 | 1 | 3 | 2 | 1 | 1 | 2 | 2 | 3 | 3 | 2 | 3 | 1 | 2 | 3 |
| | 0.5 (0.56) | 1 | 1 | 1 | 1 | 1 | 1 | 1 | 1 | 1 | 1 | 1 | 2 | 2 | 2 | 2 | 1 | 2 | 2 | 1 | 2 |
| | 0.25 (0.28) | | | | | | | | | | | | 2 | | 2 | 1 | | | 1 | | | 1 |
| 69 | 8.0 (8.96) | 1 | 1 | | 1 | 1 | 3 | 1 | 1 | 1 | 1 | 4 | 3 | 4 | 5 | 5 | 2 | 4 | 1 | 5 | 5 |
| | 4.0 (4.48) | 1 | 1 | | 1 | 1 | 1 | 1 | 1 | 1 | | 3 | 2 | 3 | 2 | 3 | 2 | 4 | | 3 | 3 |
| | 2.0 (2.24) | 1 | 1 | | 1 | 1 | 1 | | 1 | 1 | | 2 | 2 | 2 | 3 | 2 | 1 | 2 | | 2 | 2 |
| | 1.0 (1.12) | 1 | 1 | | 1 | 1 | 1 | 1 | 1 | 1 | | 2 | 2 | 1 | 2 | 2 | 1 | 2 | | 1 | 1 |
| 77 | 8.0 (8.96) | 1 | 3 | 2 | 2 | 5 | 4 | 1 | 5 | 5 | 3 | 5 | 4 | 4 | 5 | 4 | 4 | 5 | 3 | 4 | 5 |
| | 4.0 (4.48) | 1 | 2 | 1 | 1 | 2 | 1 | 1 | 3 | 4 | 1 | 3 | 3 | 2 | 4 | 3 | 2 | 3 | 2 | 4 | 3 |
| | 2.0 (2.24) | 1 | 1 | 1 | 1 | 1 | 1 | 1 | 2 | 2 | 1 | 2 | 2 | 2 | 2 | 2 | 1 | 2 | 1 | 2 | 2 |
| | 1.0 (1.12) | 1 | 1 | 1 | 1 | 1 | 1 | 1 | 1 | 1 | 1 | 2 | 2 | 2 | 2 | 2 | 1 | 2 | | 1 | 3 |
| 9 | 8.0 (8.96) | 1 | 1 | 1 | 1 | 2 | 3 | 1 | 2 | 2 | 2 | 4 | 3 | 3 | 4 | 4 | 2 | 3 | 2 | 3 | 3 |
| | 4.0 (4.48) | 1 | 2 | 1 | 1 | 1 | 2 | 1 | 2 | 2 | 1 | 3 | 2 | 2 | 2 | 3 | 2 | 3 | 2 | 2 | 2 |
| | 2.0 (2.24) | 1 | 1 | 1 | 1 | 1 | 1 | 1 | 1 | 1 | 1 | 1 | 2 | 2 | 2 | 2 | 2 | 2 | 1 | 2 | 2 |
| | 1.0 (1.12) | 1 | 1 | | 1 | 1 | 1 | | 1 | 1 | | 1 | 1 | 1 | 2 | 1 | 1 | 1 | | 1 | 1 |
| 16 | 8.0 (8.96) | 1 | 1 | | 1 | 2 | 3 | 1 | 2 | 4 | 4 | 4 | 3 | 4 | 5 | 3 | 3 | 3 | 2 | 3 | 5 |
| | 4.0 (4.48) | 1 | 1 | | 1 | 1 | 2 | 1 | 2 | 2 | 2 | 2 | 2 | 2 | 2 | 2 | 1 | 3 | 1 | 2 | 3 |
| | 2.0 (2.24) | 1 | 1 | | 1 | 1 | 1 | 1 | 1 | 1 | 1 | 2 | 1 | 2 | 2 | 2 | 1 | 1 | | 1 | 2 |
| | 1.0 (1.12) | | | | | | | | | | | | | | 1 | 1 | | | | | 1 | 1 |
| 29 | 8.0 (8.96) | 1 | 1 | | 1 | 2 | 4 | 2 | 5 | 5 | 2 | 5 | 3 | 3 | 5 | 4 | 2 | 2 | 3 | 2 | 3 |
| 82 | 8.0 (8.96) | 1 | 1 | 1 | 1 | 1 | 3 | 2 | 2 | 3 | 3 | 5 | 4 | 3 | 5 | 5 | 2 | 2 | 2 | 5 | 5 |
| 57 | 8.0 (8.96) | 1 | 1 | 1 | 1 | 1 | 2 | 1 | 2 | 1 | 1 | 4 | 3 | 2 | 4 | 2 | 2 | 5 | 2 | 3 | 3 |
| | 4.0 (4.48) | 1 | 1 | 1 | 1 | 1 | 1 | 1 | 1 | 1 | 1 | 3 | 3 | 2 | 3 | 2 | 1 | 2 | 2 | 2 | 3 |
| | 2.0 (2.24) | 1 | 1 | 1 | 1 | 1 | 1 | 1 | 1 | 1 | 1 | 2 | 2 | 2 | 2 | 2 | 2 | 2 | 1 | 1 | 1 |
| | 1.0 (1.12) | | | | | | | | | | | 1 | 1 | | 2 | 1 | 1 | 1 | | 1 | | |
| | 1.0 (1.12) | 1 | 1 | 1 | 1 | 1 | 1 | | 1 | 1 | | 1 | 2 | | 2 | 1 | 1 | | | 1 | 1 |
| | 0.5 (0.56) | | | | | | | | | | | | | | | | | | | | | |
| | 0.25 (0.28) | | | | | | | | | | | | | | | | | | | | | |
| 27 | 8.0 (8.96) | 2 | 1 | 1 | 1 | | 1 | | 1 | 1 | | 4 | 3 | 3 | 3 | 4 | 4 | 4 | 4 | 4 | 5 |
| | 4.0 (4.48) | 2 | 3 | 1 | 1 | 1 | 1 | 1 | 1 | 1 | | 4 | 2 | 3 | 2 | 3 | 3 | 4 | 3 | 4 | 3 |
| | 2.0 (2.24) | 1 | 1 | 1 | 1 | 1 | 1 | 1 | 1 | 1 | | 3 | 2 | 2 | 2 | 2 | 2 | 2 | 1 | 2 | 2 |
| | 1.0 (1.12) | 1 | 1 | 1 | 1 | 1 | 1 | 1 | 1 | 1 | | 2 | 2 | 2 | 2 | 2 | 2 | 2 | 1 | 2 | 2 |
| | 1.0 (1.12) | 1 | 1 | | 1 | | 1 | | | | | | 2 | | 2 | 1 | | | | 1 | | 1 |
| | 0.5 (0.56) | 1 | 1 | | 1 | | 1 | | | 1 | | 1 | 2 | | 1 | 2 | | | | 1 | | 1 |

TABLE II-continued

| | | Crops | | | | | | | | Preemergence Weeds | | | | | | | | | |
|---|---|---|---|---|---|---|---|---|---|---|---|---|---|---|---|---|---|---|---|
| Example No. Compound Tested | Rate of Appln. lbs/acre (kg/ha) | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
| 89 | 0.25 (0.28) | 1 | 1 | 1 | 1 | 1 | 1 | 1 | 1 | 1 | | 1 | 1 | 1 | 3 | 1 | 1 | 1 | 1 | 2 | 1 |
| | 8.0 (8.96) | 1 | 1 | 2 | 1 | 1 | 2 | 2 | 3 | 3 | 3 | 4 | 4 | 4 | 4 | 2 | 1 | 4 | 1 | 2 | 3 |
| | 4.0 (4.48) | 1 | 1 | 1 | 1 | 1 | 2 | 1 | 2 | 3 | 2 | 3 | 4 | 2 | 4 | 3 | 2 | 2 | 1 | 2 | 4 |
| | 2.0 (2.24) | 1 | 1 | 1 | 1 | 1 | 1 | | 1 | 1 | 1 | 2 | 2 | 1 | 3 | 2 | 2 | 2 | | 2 | 1 |
| | 1.0 (1.12) | 1 | 1 | 1 | 1 | 1 | 1 | | | 1 | 1 | | 2 | 1 | 2 | 2 | 2 | 2 | | 3 | 2 |
| 90 | 8.0 (8.96) | | | | | | | | | | | | | | | | | | | | |
| 74 | 8.0 (8.96) | 3 | 3 | 3 | 2 | 5 | 4 | 2 | 4 | 5 | 3 | 5 | 4 | 5 | 5 | 4 | 4 | 4 | 5 | 3 | 5 |
| | 4.0 (4.48) | 2 | 3 | 3 | 1 | 4 | 4 | 2 | 4 | 4 | 4 | 5 | 4 | 4 | 5 | 4 | 4 | 5 | 4 | 4 | 5 |
| | 2.0 (2.24) | 1 | 1 | 3 | 1 | 2 | 2 | 1 | 4 | 4 | 2 | 4 | 3 | 3 | 5 | 3 | 2 | 4 | 3 | 3 | 3 |
| | 1.0 (1.12) | 1 | 3 | 3 | 1 | 3 | 2 | 2 | 4 | 4 | 2 | 3 | 4 | 4 | 5 | 3 | 1 | 3 | 2 | 3 | 3 |
| | 1.0 (1.12) | 1 | 1 | 2 | 1 | 1 | 2 | 1 | 3 | 2 | 1 | 3 | 2 | 2 | 4 | 3 | 2 | 3 | 1 | 3 | 2 |
| | 0.5 (0.56) | 1 | 1 | 2 | 1 | 1 | 1 | 2 | 2 | 3 | 2 | 1 | 2 | 2 | 2 | 2 | 2 | 2 | | 2 | 2 |
| | 0.25 (0.28) | | | | | | | | | 2 | | 2 | 2 | | 2 | 2 | | 1 | | 2 | 2 |
| 18 | 8.0 (8.96) | 1 | 1 | 2 | 1 | 4 | 3 | 2 | 3 | 3 | 2 | 4 | 4 | 3 | 5 | 4 | 4 | 5 | 3 | 2 | 4 |
| | 4.0 (4.48) | | 1 | 1 | 1 | 3 | 2 | 2 | 2 | 4 | 1 | 4 | 3 | 2 | 5 | 2 | 2 | 4 | | 2 | 3 |
| | 2.0 (2.28) | 1 | 1 | 1 | | 1 | 1 | 1 | 1 | 1 | 1 | 2 | 2 | 2 | 4 | 2 | 2 | 3 | 1 | 1 | 2 |
| | 1.0 (1.12) | 1 | 1 | | 1 | | | | | | 1 | | 2 | 1 | 3 | 1 | 1 | 1 | | 1 | 1 |
| 50 | 8.0 (8.96) | 3 | 3 | 3 | 4 | 5 | 5 | 2 | 5 | 5 | 4 | 5 | 5 | 5 | 5 | 5 | 5 | 5 | 5 | 5 | 5 |
| | 4.0 (4.48) | 1 | 2 | 1 | 1 | 5 | 4 | 2 | 5 | 4 | 3 | 5 | 4 | 4 | 5 | 4 | 4 | 4 | 4 | 4 | 5 |
| | 2.0 (2.24) | 1 | 1 | 1 | 1 | 3 | 4 | 1 | 3 | 4 | 4 | 4 | 4 | 4 | 5 | 4 | 2 | 4 | 4 | 3 | 3 |
| | 1.0 (1.12) | 1 | 1 | 2 | 2 | 4 | 4 | 2 | 5 | 3 | 3 | 5 | 4 | 4 | 5 | 2 | 2 | 4 | 4 | 3 | 2 |
| | 1.0 (1.12) | 1 | 1 | 1 | 1 | 2 | 2 | 2 | 2 | 2 | 2 | 4 | 2 | 3 | 4 | 3 | 2 | 3 | 1 | 4 | 4 |
| | 0.5 (0.56) | 1 | 1 | 1 | 1 | 1 | | 2 | 2 | 1 | 1 | 3 | 1 | 2 | 2 | 2 | 1 | 2 | | 1 | 2 |
| | 0.25 (0.28) | | | | | | | | | 1 | 1 | | | | 1 | 1 | | 1 | | 1 | 1 |
| 79 | 8.0 (8.96) | 2 | 1 | 2 | 1 | 2 | 4 | 2 | 2 | 4 | 4 | 5 | 4 | 5 | 5 | 4 | 4 | 5 | | 5 | 5 |
| | 4.0 (4.48) | 2 | 2 | 2 | 1 | 1 | 4 | 1 | 2 | 3 | 3 | 4 | 4 | 2 | 5 | 4 | 2 | 4 | 3 | 2 | 5 |
| | 2.0 (2.24) | 1 | 1 | 1 | 1 | 1 | 2 | 1 | 2 | 1 | 1 | 4 | 2 | 1 | 5 | 2 | 1 | 3 | 1 | 3 | 3 |
| | 1.0 (1.12) | 1 | 2 | 1 | 1 | 1 | 1 | 1 | 2 | 1 | 2 | 3 | 2 | | 4 | 2 | | 2 | | 1 | 2 |
| | 1.0 (1.12) | 1 | 1 | 2 | 1 | 1 | 2 | 1 | 2 | 1 | 1 | 3 | | 2 | 4 | 2 | | 2 | | 1 | 2 |
| | 0.5 (0.56) | 1 | 1 | 1 | 1 | | 1 | | 1 | 1 | 1 | | | 2 | 2 | 1 | 1 | 1 | | 1 | 1 |
| | 0.25 (0.28) | | | | | | | | | 1 | | | | 2 | 2 | | | 1 | | 1 | 1 |
| 45 | 8.0 (8.96) | 2 | 3 | 2 | 1 | 2 | 5 | 1 | 5 | 4 | 5 | 4 | 4 | 5 | 5 | 5 | 4 | 5 | 4 | 5 | 5 |
| | 4.0 (4.48) | 2 | 2 | 2 | 1 | 3 | 5 | 1 | 4 | 3 | 3 | 4 | 4 | 5 | 5 | 5 | 3 | 4 | 4 | 4 | 5 |
| | 2.0 (2.24) | 1 | 1 | 1 | 1 | 1 | 4 | | 3 | 3 | 3 | 4 | 4 | 5 | 5 | 4 | 2 | 3 | 4 | 3 | 5 |
| | 1.0 (1.12) | 1 | 1 | 2 | 1 | 1 | 4 | 2 | 2 | 2 | 2 | 4 | 4 | 2 | 4 | 2 | 1 | 3 | 3 | 2 | 2 |
| | 1.0 (1.12) | 1 | 1 | 1 | 1 | 1 | 3 | 2 | 2 | 1 | 1 | 3 | 3 | 2 | 4 | 2 | 1 | 2 | 1 | 2 | 1 |
| | 0.5 (0.56) | 1 | 1 | 2 | 1 | 1 | 2 | 2 | 2 | 2 | 2 | | 3 | | 2 | 1 | 1 | 2 | 1 | 2 | 1 |
| | 0.25 (0.78) | | | | | | | | | 1 | | | 1 | | 2 | | | 1 | | | 1 |
| 47 | 8.0 (8.96) | 1 | 1 | 1 | 1 | 1 | 3 | 1 | 1 | 2 | 2 | 4 | 3 | 3 | 5 | 5 | 1 | 4 | 4 | 5 | 5 |
| | 4.0 (4.48) | 1 | 1 | 1 | 1 | 1 | 3 | 1 | 1 | 1 | 1 | 4 | 3 | 3 | 4 | 3 | 1 | 3 | 2 | 4 | 5 |
| | 2.0 (2.24) | 1 | 1 | 1 | 1 | 1 | 1 | 1 | 1 | 1 | 1 | 3 | 2 | 2 | 3 | 3 | 1 | 2 | 3 | 3 | 2 |
| | 1.0 (1.12) | 1 | 1 | | 1 | 1 | | | 1 | 1 | 1 | | | 2 | 2 | 2 | 1 | 2 | 1 | 2 | 1 |
| 48 | 8.0 (8.96) | 1 | 1 | 1 | 1 | 1 | 3 | 1 | 1 | 2 | 2 | 4 | 3 | 4 | 4 | 4 | 2 | 4 | 4 | | 4 |
| | 4.0 (4.48) | 1 | 1 | 1 | 1 | 1 | 1 | 1 | 2 | 1 | 1 | 3 | 2 | 3 | 3 | 3 | 2 | 3 | 3 | 4 | 1 |
| | 2.0 (2.24) | 1 | 1 | 1 | 1 | 1 | 1 | 1 | 3 | 3 | 2 | 2 | 2 | 2 | 2 | 2 | 1 | 1 | 1 | 1 | 1 |
| | 1.0 (1.12) | 1 | 1 | 1 | 1 | 1 | 1 | 1 | 2 | 3 | 1 | 1 | 2 | 2 | 2 | 1 | 1 | 1 | 2 | 1 | 2 |
| 17 | 8.0 (8.96) | 1 | 1 | 1 | 1 | 1 | 1 | 1 | 3 | 3 | 3 | 2 | 4 | 3 | 5 | 5 | 4 | 5 | 3 | 5 | 5 |

TABLE II-continued

Preemergence

| Example No. of Compound Tested | Rate of Appln. lbs/acre (kg/ha) | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
|---|---|---|---|---|---|---|---|---|---|---|---|---|---|---|---|---|---|---|---|---|---|
| | 4.0 (4.48) | 2 | 5 | 3 | 2 | 3 | 5 | 2 | 2 | 4 | 4 | 5 | 4 | 4 | 5 | 5 | 5 | 5 | 5 | 5 | 5 |
| | 2.0 (2.24) | 3 | 4 | 4 | 2 | 5 | 5 | 2 | 2 | 5 | 4 | 5 | 4 | 4 | 5 | 5 | 4 | 5 | 5 | 5 | 4 |
| | 1.0 (1.12) | 2 | 5 | 2 | 1 | 4 | 5 | 2 | 2 | 4 | 3 | 4 | 4 | 3 | 4 | 4 | 2 | 4 | 4 | 2 | 5 |
| | 1.0 (1.12) | 1 | 1 | 1 | 1 | 1 | 4 | 1 | 2 | 3 | 1 | 4 | 3 | 3 | 4 | 3 | 2 | 5 | 2 | 3 | 3 |
| | 0.5 (0.56) | 1 | 2 | 1 | 1 | 1 | 4 | 1 | 1 | 1 | 1 | 3 | 3 | 3 | 3 | 1 | 1 | 3 | 1 | 1 | 2 |
| | 0.25 (0.28) | 1 | 1 | 1 | 1 | 1 | 2 | 1 | 1 | 1 | 1 | 3 | 3 | 2 | 3 | 1 | 2 | 2 | | 2 | 4 |
| 40 | 8.0 (8.96) | 2 | 2 | 1 | 1 | 3 | 4 | 2 | 3 | 4 | 1 | | 4 | 3 | 5 | 4 | 2 | 4 | 5 | 5 | 5 |
| | 4.0 (4.48) | 2 | 1 | 1 | 1 | 2 | 4 | 2 | 2 | 2 | 1 | 4 | 2 | 3 | 5 | 3 | 1 | 4 | 3 | 4 | 4 |
| | 2.0 (2.24) | 1 | 1 | 1 | 1 | 1 | 4 | 1 | 1 | 2 | 1 | 4 | 2 | 2 | 4 | 2 | 2 | 2 | 2 | 4 | 5 |
| | 1.0 (1.12) | 1 | 1 | 1 | 1 | 1 | 1 | 1 | 1 | 2 | 2 | | 3 | 1 | 3 | 2 | 1 | 3 | | 3 | 2 |
| 2 | 8.0 (8.96) | 1 | 1 | 1 | 1 | 2 | 2 | 3 | 1 | 2 | 3 | 5 | 3 | 4 | 5 | 3 | 2 | 5 | 4 | 4 | 5 |
| 10 | 4.0 (4.48) | 1 | 1 | 1 | 1 | 2 | 4 | 1 | 1 | 2 | 3 | 5 | 3 | 3 | 4 | 2 | 1 | 2 | 2 | 2 | 2 |
| | 2.0 (2.24) | 1 | 2 | 2 | 3 | 3 | 5 | 2 | 2 | 2 | 4 | 1 | 5 | 2 | 5 | 3 | 3 | 5 | 3 | 3 | 3 |
| | 1.0 (1.12) | 1 | 1 | 1 | 1 | 3 | 1 | 2 | 1 | 2 | 2 | 5 | 2 | 3 | 4 | 3 | 2 | 3 | 5 | 2 | 2 |
| | 1.0 (1.12) | 1 | 1 | 1 | 1 | 1 | 1 | 1 | 1 | 1 | 1 | 3 | 2 | 2 | 3 | 2 | 1 | 2 | 2 | 2 | 2 |
| | 0.5 (0.56) | 1 | 1 | 1 | 1 | 1 | 1 | 1 | 1 | 1 | 1 | 3 | 2 | 2 | 3 | 2 | 1 | 2 | 1 | 1 | 1 |
| | 0.25 (0.28) | 1 | 1 | 1 | 1 | 1 | 1 | 1 | 1 | 1 | 1 | | | | | | | | | | |
| 64 | 8.0 (8.96) | 1 | | 2 | | 4 | 5 | 2 | 3 | 3 | 4 | 5 | 4 | 4 | 4 | 5 | 2 | 4 | 5 | 3 | 5 |
| | 4.0 (4.48) | | 1 | 2 | 1 | 4 | 4 | 2 | 3 | 2 | 3 | 4 | 4 | 4 | 5 | 5 | 5 | 2 | 2 | 4 | 4 |
| | 2.0 (2.24) | 1 | 2 | | 1 | 1 | 5 | 1 | 2 | 2 | 4 | 4 | 5 | 3 | 5 | 5 | 2 | 3 | 1 | 3 | 3 |
| | 1.0 (1.12) | 1 | 1 | 1 | 1 | 1 | 1 | 1 | 2 | 2 | 2 | 4 | 3 | 3 | 4 | 3 | 2 | 3 | 2 | 3 | 2 |
| | 1.0 (1.12) | 1 | 1 | 1 | 1 | 1 | 1 | 1 | 2 | 2 | 2 | 3 | 3 | 3 | 4 | 3 | 2 | 2 | | 2 | 2 |
| | 0.5 (0.56) | 1 | 1 | 1 | 1 | 1 | 1 | 1 | 1 | 1 | 1 | 2 | 2 | 2 | 3 | 3 | 1 | 2 | 2 | 1 | 2 |
| | 0.25 (0.28) | 1 | 1 | 1 | 1 | 1 | 1 | 1 | 2 | 1 | 1 | | | 2 | 3 | 1 | 1 | 2 | 1 | 1 | 1 |
| 71 | 8.0 (8.96) | 1 | 4 | 4 | | 5 | 4 | 2 | 5 | 5 | 4 | 4 | | 4 | 5 | 5 | 5 | 5 | 5 | 5 | 5 |
| | 4.0 (4.48) | 1 | 2 | 2 | 3 | 2 | 2 | 2 | 4 | 4 | 2 | 3 | | 4 | 5 | 5 | 4 | 5 | 2 | 5 | 4 |
| | 2.0 (2.24) | 1 | 1 | 1 | 1 | 3 | 4 | 2 | 3 | 3 | 4 | 4 | 4 | 4 | 4 | 5 | 2 | 5 | 4 | 4 | 3 |
| | 1.0 (1.12) | 1 | 2 | 1 | 1 | 2 | 4 | 2 | 2 | 2 | 2 | 2 | 4 | 4 | 4 | 2 | 2 | 2 | 3 | 3 | 3 |
| | 1.0 (1.12) | 1 | 2 | 2 | 2 | 1 | 4 | 2 | 2 | 2 | 2 | 2 | 3 | 2 | 5 | 2 | 2 | 2 | 2 | 3 | 3 |
| | 0.5 (0.56) | 1 | 1 | 1 | 1 | 1 | 2 | 1 | 2 | 1 | 2 | 1 | 2 | 3 | 3 | 3 | 2 | 2 | | 3 | 3 |
| | 0.25 (0.28) | 1 | 1 | 1 | 1 | 1 | 1 | 1 | 1 | 1 | 1 | | | | | 1 | 1 | | | 2 | 2 |
| 72 | 8.0 (8.96) | 4 | 3 | 4 | 2 | 3 | 4 | 2 | 5 | 5 | 4 | 4 | 5 | 5 | 5 | 5 | 5 | 5 | 5 | 5 | 5 |
| | 4.0 (4.48) | 1 | 3 | 3 | 1 | 3 | 4 | 2 | 3 | 4 | 3 | 5 | 4 | 4 | 5 | 4 | 4 | 5 | 5 | 4 | 4 |
| | 2.0 (2.24) | 1 | 1 | 1 | 2 | 1 | 4 | 2 | 2 | 3 | 2 | 4 | 3 | 4 | 4 | 5 | 3 | 4 | 5 | 3 | 3 |
| | 1.0 (1.12) | 2 | 2 | 2 | 2 | 4 | 4 | 2 | 4 | 4 | 4 | 4 | 4 | 4 | 4 | 4 | 2 | 4 | 2 | 3 | 3 |
| | 1.0 (1.12) | 1 | 2 | 1 | 1 | 1 | 2 | 2 | 2 | 3 | 1 | 4 | 4 | 3 | 4 | 3 | 2 | 2 | 3 | 2 | 2 |
| | 0.5 (0.56) | 1 | 2 | 2 | 1 | 2 | 4 | 2 | 2 | 3 | 1 | 2 | 4 | 2 | 3 | 3 | 2 | 2 | 2 | 2 | 2 |
| | 0.25 (0.28) | 1 | 2 | 1 | 1 | 1 | 2 | 2 | 2 | 2 | 1 | 2 | 4 | 2 | 3 | 3 | 2 | 2 | 2 | 2 | 2 |
| | 0.125 (0.14) | 1 | 1 | 1 | 1 | 1 | 2 | 1 | 1 | 1 | 1 | 1 | | 2 | 4 | 3 | 1 | 2 | 4 | 2 | 2 |
| | 0.0625 (0.07) | 1 | 1 | 1 | 1 | 1 | 1 | 1 | 1 | 1 | 1 | 1 | | 3 | 1 | 2 | 1 | 1 | | 1 | 1 |
| 22 | 8.0 (8.96) | 1 | 2 | 1 | 1 | 1 | 4 | 1 | 2 | 1 | 1 | | 3 | 2 | 2 | 2 | 1 | 3 | 3 | 2 | 2 |
| | 4.0 (4.48) | 1 | 1 | 1 | 1 | 1 | 1 | 1 | 1 | 1 | 1 | | 1 | 2 | 2 | 2 | 1 | 2 | 1 | 1 | 1 |
| 35 | 2.0 (2.24) | 1 | | 1 | 1 | 1 | 3 | | | 3 | 1 | 5 | 3 | 3 | 4 | 4 | 2 | 2 | | 4 | 4 |
| | 1.0 (1.12) | 1 | 1 | | 1 | 1 | | 1 | 2 | 2 | 2 | 5 | | 4 | 2 | 3 | 1 | 2 | 1 | 1 | 1 |
| | 8.0 (8.96) | | | | | | | | | | | | | | | | | | | | |
| | 4.0 (4.48) | | | | | | | | | | | | | | | | | | | | |

TABLE II-continued

Preemergence

| Example No. of Compound Tested | Rate of Appln. lbs/acre (kg/ha) | Crops | | | | | | | | | Weeds | | | | | | | | |
|---|---|---|---|---|---|---|---|---|---|---|---|---|---|---|---|---|---|---|---|
| | | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
| 49 | 2.0 (2.24) | 1 | 1 | 2 | 1 | 1 | 2 | 2 | 3 | 2 | 2 | 2 | 3 | 1 | 4 | 2 | 1 | 2 | 1 | 1 | 1 |
| | 1.0 (1.12) | 1 | 1 | 1 | 1 | 1 | 1 | 1 | 1 | 1 | 1 | 4 | 3 | 2 | 3 | 2 | 1 | 2 | 1 | 2 | 1 |
| | 8.0 (8.96) | 2 | 2 | 1 | 1 | 1 | 4 | 2 | 2 | 4 | 4 | 4 | 4 | 4 | 5 | 4 | 4 | 5 | 3 | 1 | 5 |
| | 4.0 (4.48) | 1 | 2 | 1 | 1 | 2 | 5 | 2 | 2 | 2 | 3 | 4 | 3 | 2 | 5 | 4 | 2 | 3 | 3 | 1 | 5 |
| | 2.0 (2.24) | 1 | 1 | 1 | 1 | 1 | 2 | 1 | 2 | 3 | 3 | 4 | 2 | 2 | 4 | 4 | 2 | 2 | 1 | 1 | 4 |
| | 1.0 (1.12) | 1 | 1 | 1 | 1 | 1 | 1 | 1 | 1 | 1 | 1 | 2 | 1 | 2 | 2 | 2 | 1 | 1 | 1 | 1 | 3 |
| 15 | 8.0 (8.96) | 3 | 5 | 3 | 4 | 5 | 5 | 4 | 5 | 5 | 4 | 4 | 5 | 4 | 4 | 5 | 3 | 5 | 5 | 3 | 5 |
| | 4.0 (4.48) | 4 | 3 | 2 | 3 | 3 | 4 | 3 | 5 | 4 | 4 | 2 | 5 | 2 | 4 | 4 | 2 | 5 | 5 | 5 | 5 |
| | 2.0 (2.24) | 1 | 1 | 1 | 1 | 2 | 2 | 2 | 3 | 1 | 2 | 1 | 3 | 2 | 3 | 3 | 1 | 3 | 4 | 1 | 2 |
| 66 | 8.0 (8.96) | 3 | 4 | 4 | 3 | 5 | 4 | 2 | 5 | 4 | 4 | 5 | 5 | 5 | 5 | 5 | 4 | 5 | 5 | 5 | 5 |
| | 4.0 (4.48) | 2 | 3 | 3 | 2 | 5 | 4 | 2 | 5 | 5 | 4 | 5 | 5 | 4 | 5 | 4 | 3 | 4 | 4 | 4 | 5 |
| | 2.0 (2.24) | 1 | 1 | 1 | 1 | 3 | 3 | 2 | 3 | 4 | 2 | 4 | 3 | 3 | 4 | 3 | 3 | 4 | 4 | 2 | 3 |
| | 1.0 (1.12) | 1 | 1 | 2 | 1 | 2 | 4 | 2 | 3 | 4 | 3 | 5 | 4 | 3 | 5 | 4 | 2 | 4 | 4 | 1 | 4 |
| | 1.0 (1.12) | 1 | 1 | 1 | 1 | 1 | 1 | 2 | 1 | 1 | 1 | 2 | 3 | 2 | 3 | 3 | 2 | 3 | 1 | 1 | 2 |
| | 0.5 (0.56) | 1 | 1 | 1 | 1 | 1 | 1 | 1 | 1 | 1 | 1 | 1 | 2 | 2 | 2 | 3 | 1 | 1 | 1 | 1 | 2 |
| | 0.25 (0.28) | 1 | 1 | 1 | 1 | 1 | 1 | 1 | 1 | 1 | 1 | 1 | 1 | 1 | 1 | 1 | 1 | 1 | 1 | 1 | 1 |
| 26 | 8.0 (8.96) | 2 | 2 | 1 | 2 | 2 | 4 | 2 | 3 | 4 | 3 | 4 | 5 | 4 | 4 | 5 | 4 | 5 | 2 | 1 | 4 |
| | 4.0 (4.48) | 1 | 3 | 2 | 1 | 3 | 2 | 2 | 2 | 1 | 2 | 3 | 5 | 3 | 4 | 4 | 2 | 3 | 2 | 4 | 4 |
| | 2.0 (2.24) | 1 | 1 | 1 | 1 | 1 | 2 | 1 | 1 | 1 | 3 | 4 | 3 | 2 | 5 | 3 | 2 | 4 | 2 | 2 | 4 |
| | 1.0 (1.12) | 1 | 1 | 1 | 1 | 1 | 1 | 1 | 1 | 1 | 1 | 3 | 2 | 1 | 3 | 3 | 1 | 3 | 1 | 1 | 3 |
| | 1.0 (1.12) | 1 | 1 | 1 | 1 | 1 | 1 | 1 | 1 | 1 | 2 | 4 | 2 | 2 | 3 | 3 | 1 | 2 | 1 | 1 | 2 |
| | 0.5 (0.56) | 1 | 1 | 1 | 1 | 1 | 1 | 1 | 1 | 1 | 1 | 1 | 1 | 1 | 1 | 1 | 1 | 1 | 1 | 1 | 1 |
| | 0.25 (0.28) | 1 | 1 | 1 | 1 | 1 | 1 | 1 | 1 | 1 | 1 | 1 | 1 | 1 | 1 | 1 | 1 | 1 | 1 | 1 | 1 |
| 81 | 8.0 (8.96) | 2 | 3 | 3 | 3 | 5 | 5 | 2 | 5 | 4 | 4 | 4 | 5 | 4 | 4 | 5 | 4 | 5 | 5 | 5 | 5 |
| | 4.0 (4.48) | 1 | 3 | 2 | 3 | 4 | 4 | 2 | 5 | 4 | 3 | 4 | 5 | 3 | 4 | 4 | 4 | 4 | 4 | 5 | 5 |
| | 2.0 (2.24) | 1 | 3 | 1 | 2 | 4 | 4 | 2 | 4 | 3 | 2 | 4 | 4 | 3 | 5 | 3 | 3 | 5 | 2 | 2 | 4 |
| | 1.0 (1.12) | 1 | 1 | 1 | 1 | 2 | 3 | 2 | 5 | 4 | 2 | 3 | 4 | 2 | 5 | 3 | 2 | 3 | 1 | 2 | 2 |
| | 1.0 (1.12) | 1 | 1 | 1 | 1 | 1 | 1 | 1 | 2 | 1 | 1 | 1 | 3 | 2 | 2 | 2 | 1 | 2 | 1 | 1 | 2 |
| 55 | 8.0 (8.96) | 1 | 1 | 1 | 1 | 2 | 3 | 2 | 5 | 3 | 4 | 5 | 5 | 5 | 4 | 5 | 3 | 5 | 2 | 5 | 5 |
| | 4.0 (4.48) | 1 | 1 | 1 | 1 | 1 | 3 | 2 | 5 | 4 | 1 | 4 | 4 | 4 | 5 | 3 | 3 | 3 | 3 | 5 | 3 |
| | 2.0 (2.24) | 1 | 1 | 1 | 1 | 1 | 2 | 1 | 3 | 3 | 1 | 3 | 4 | 2 | 5 | 3 | 1 | 4 | 1 | 2 | 2 |
| | 1.0 (1.12) | 1 | 1 | 1 | 1 | 1 | 1 | 1 | 1 | 3 | 3 | 3 | 3 | 2 | 4 | 3 | 1 | 4 | 1 | 2 | 2 |
| 13 | 8.0 (8.96) | 2 | 2 | 3 | 3 | 5 | 4 | 2 | 5 | 5 | 4 | 5 | 5 | 4 | 5 | 5 | 5 | 5 | 4 | 5 | 5 |
| | 4.0 (4.48) | 1 | 2 | 2 | 1 | 5 | 3 | 2 | 5 | 4 | 3 | 5 | 5 | 4 | 5 | 4 | 4 | 5 | 2 | 5 | 5 |
| | 2.0 (2.24) | 1 | 1 | 2 | 1 | 2 | 3 | 2 | 3 | 5 | 4 | 5 | 3 | 3 | 3 | 5 | 2 | 2 | 2 | 2 | 2 |
| | 1.0 (1.12) | 1 | 1 | 1 | 1 | 1 | 1 | 1 | 2 | 1 | 3 | 5 | 3 | 2 | 3 | 3 | 1 | 3 | 1 | 1 | 2 |
| 1 | 8.0 (8.96) | 2 | 5 | 4 | 4 | 5 | 4 | 3 | 5 | 5 | 5 | 5 | 5 | 4 | 5 | 5 | 5 | 5 | 5 | 5 | 5 |
| | 4.0 (4.48) | 1 | 2 | 3 | 2 | 5 | 4 | 2 | 5 | 4 | 4 | 4 | 5 | 3 | 5 | 4 | 4 | 5 | 4 | 2 | 5 |
| | 2.0 (2.24) | 1 | 2 | 2 | 1 | 3 | 4 | 2 | 4 | 4 | 3 | 5 | 4 | 3 | 5 | 3 | 2 | 2 | 2 | 2 | 4 |
| | 1.0 (1.12) | 1 | 1 | 1 | 1 | 5 | 4 | 2 | 3 | 2 | 2 | 5 | 3 | 3 | 5 | 3 | 3 | 5 | 1 | 3 | 2 |
| | 1.0 (1.12) | 1 | 1 | 1 | 1 | 1 | 2 | 2 | 2 | 2 | 1 | 3 | 2 | 3 | 3 | 3 | 1 | 4 | 1 | 1 | 2 |
| | 0.5 (0.56) | 2 | 2 | 1 | 1 | 1 | 1 | 2 | 1 | 1 | 1 | 1 | 2 | 3 | 3 | 2 | 1 | 3 | 1 | 1 | 2 |
| | 0.25 (0.28) | 2 | 1 | 2 | 1 | 1 | 1 | 2 | 1 | 1 | 1 | 1 | 3 | 3 | 3 | 3 | 1 | 2 | 1 | 1 | 1 |
| 7 | 8.0 (8.96) | 2 | 2 | 2 | 1 | 1 | 1 | 2 | 1 | 1 | 1 | 2 | 3 | 3 | 4 | 3 | 1 | 4 | 2 | 3 | 2 |

TABLE II-continued

Preemergence

| Example No. of Compound Tested | Rate of Appln. lbs/acre (kg/ha) | Crops | | | | | | | | Weeds | | | | | | | | |
|---|---|---|---|---|---|---|---|---|---|---|---|---|---|---|---|---|---|---|
| | | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
| 87 | 4.0 (4.48) | 1 | 1 | 1 | 1 | 1 | 1 | 1 | 3 | 2 | 2 | 1 | 3 | 3 | 4 | 2 | 1 | 3 | 1 | 1 | 3 |
| | 2.0 (2.24) | 1 | 1 | 1 | 1 | 1 | 1 | 1 | 1 | 1 | 1 | 3 | 2 | 2 | 3 | 1 | 1 | 1 | 1 | 1 | 5 |
| | 1.0 (1.12) | 1 | 1 | 1 | 1 | 1 | 1 | 1 | 1 | 1 | 1 | 1 | 2 | 1 | 4 | 1 | 1 | 2 | 1 | 1 | 5 |
| | 8.0 (8.96) | 1 | 4 | 3 | 3 | 4 | 4 | 2 | 5 | 4 | 4 | 4 | 4 | 5 | 5 | 4 | 2 | 5 | 4 | 5 | 5 |
| | 4.0 (4.48) | 1 | 2 | 2 | 1 | 2 | 4 | 2 | 4 | 4 | 4 | 5 | 4 | 5 | 5 | 4 | 2 | 5 | 5 | 5 | 5 |
| | 2.0 (2.24) | 1 | 2 | 1 | 1 | 2 | 2 | 2 | 3 | 3 | 2 | 4 | 4 | 4 | 4 | 3 | 2 | 5 | 2 | 4 | 4 |
| | 1.0 (1.12) | 1 | 1 | 2 | 1 | 2 | 2 | 2 | 2 | 2 | 1 | 4 | 3 | 3 | 3 | 3 | 1 | 3 | 1 | 2 | 3 |
| | 0.5 (0.56) | 1 | 1 | 1 | 1 | 1 | 3 | 2 | 2 | 2 | 1 | 3 | 3 | 3 | 3 | 2 | 1 | 3 | 1 | 2 | 3 |
| | 0.25 (0.28) | 1 | 1 | 1 | 1 | 1 | 2 | 1 | 2 | 1 | 1 | 2 | 2 | 2 | 2 | 1 | 1 | 2 | 1 | 1 | 2 |
| 34 | 8.0 (8.96) | 3 | 4 | 4 | 3 | 5 | 4 | 2 | 5 | 5 | 4 | 5 | 4 | 5 | 5 | 5 | 5 | 4 | 5 | 5 | 5 |
| | 4.0 (4.48) | 2 | 3 | 2 | 3 | 5 | 4 | 2 | 5 | 2 | 3 | 4 | 3 | 3 | 4 | 3 | 4 | 4 | 3 | 5 | 5 |
| | 2.0 (2.24) | 1 | 2 | 1 | 1 | 1 | 2 | 2 | 2 | 1 | 1 | 4 | 2 | 3 | 3 | 2 | 2 | 3 | 2 | 4 | 4 |
| | 1.0 (1.12) | 1 | 2 | 1 | 1 | 2 | 4 | 1 | 1 | 1 | 1 | 4 | 3 | 4 | 4 | 3 | 2 | 3 | 1 | 3 | 4 |
| | 0.5 (0.56) | 1 | 1 | 1 | 1 | 2 | 4 | — | 2 | 1 | 1 | 5 | 2 | 2 | 3 | 2 | 3 | 4 | 1 | 1 | 1 |
| | 0.25 (0.28) | 1 | 1 | 1 | 1 | 1 | 1 | — | 1 | 1 | 1 | 3 | — | 2 | 2 | — | 1 | 2 | 1 | 1 | 4 |
| 21 | 8.0 (8.96) | 1 | 1 | 1 | 3 | 3 | 3 | 2 | 2 | 4 | 1 | — | 4 | 3 | 3 | 3 | 2 | 3 | 4 | 3 | 3 |
| | 4.0 (4.48) | 1 | 1 | 1 | 1 | 2 | 4 | 3 | 2 | 1 | 1 | — | 3 | 3 | 3 | 3 | 1 | 4 | 3 | 1 | 2 |
| | 2.0 (2.24) | 1 | 1 | 1 | 1 | 1 | 2 | 1 | 1 | 1 | 1 | 2 | — | 2 | — | 2 | 1 | 3 | 2 | 1 | 1 |
| 76 | 8.0 (8.96) | 3 | 5 | 4 | 4 | 5 | 5 | 4 | 5 | 5 | 4 | 4 | 5 | 4 | 5 | 5 | 4 | 5 | 5 | 5 | 5 |
| | 4.0 (4.48) | 2 | 4 | 2 | 2 | 4 | 4 | 3 | 5 | 5 | 4 | 4 | 5 | 4 | 5 | 4 | 2 | 4 | 5 | 5 | 5 |
| | 2.0 (2.24) | 1 | 3 | 2 | 1 | 2 | 4 | 2 | 5 | 2 | 2 | 3 | 4 | 3 | 4 | 3 | 2 | 3 | 4 | 4 | 4 |
| | 1.0 (1.12) | 1 | 2 | 2 | 1 | 2 | 4 | 1 | 4 | 2 | 2 | 3 | 4 | 2 | 3 | 2 | 2 | 3 | 4 | 4 | 4 |
| | 0.5 (0.56) | 1 | 1 | 1 | 1 | 2 | 3 | — | 2 | 1 | 1 | 2 | 2 | 2 | 2 | 1 | 1 | 2 | 1 | 2 | 2 |
| 12 | 8.0 (8.96) | 4 | 5 | 4 | 4 | 5 | 5 | 4 | 5 | 5 | 4 | 4 | 5 | 5 | 5 | 5 | 4 | 5 | 5 | 5 | 5 |
| | 4.0 (4.48) | 4 | 5 | 4 | 2 | 5 | 4 | 3 | 5 | 5 | 4 | 4 | 4 | 4 | 5 | 4 | 3 | 5 | 5 | 5 | 5 |
| | 2.0 (2.24) | 2 | 3 | 3 | 2 | 4 | 5 | 2 | 5 | 5 | 4 | 3 | 5 | 4 | 4 | 4 | 3 | 4 | 4 | 5 | 5 |
| | 1.0 (1.12) | 3 | 4 | 3 | 2 | 4 | 3 | 1 | 3 | 3 | 2 | 2 | 4 | 3 | 3 | 3 | 2 | 5 | 3 | 4 | 4 |
| 12 | 0.5 (0.56) | 1 | 1 | 1 | 1 | 1 | 2 | 1 | 1 | 1 | 1 | — | 4 | 2 | 3 | 3 | 1 | 3 | 3 | 3 | 3 |
| | 0.25 (0.28) | 1 | 3 | 2 | 1 | 1 | 1 | 1 | 3 | 2 | 1 | 2 | — | 2 | — | — | 1 | 2 | 1 | 1 | 1 |
| | 0.25 (0.28) | 1 | 1 | 1 | 1 | 1 | 1 | — | 1 | 1 | 1 | 1 | — | 2 | 1 | 2 | — | 1 | 2 | 2 | 2 |
| | 0.125 (0.14) | 1 | 1 | 1 | 1 | 1 | 1 | — | — | — | — | — | — | — | — | — | — | 1 | — | 1 | — |
| | 0.0625 (0.07) | 1 | — | — | — | — | — | — | — | — | — | — | — | — | — | — | — | — | — | — | — |
| 91 | 8.0 (8.96) | 2 | 4 | 2 | 2 | 3 | 5 | 2 | 5 | 1 | 1 | 4 | 5 | 4 | 3 | 5 | 4 | 4 | 5 | 4 | 5 |
| | 4.0 (4.48) | 1 | 2 | 1 | 1 | 2 | 5 | 2 | 5 | 1 | 1 | 3 | 4 | 3 | 3 | 5 | 4 | 5 | 4 | 3 | 4 |
| | 2.0 (2.24) | 1 | 1 | 1 | 1 | 2 | 3 | 1 | 4 | 1 | 1 | 2 | 3 | 2 | 2 | 4 | 3 | 3 | 3 | 3 | 4 |
| | 1.0 (1.12) | 1 | 1 | 1 | 1 | 2 | 2 | 1 | 2 | 1 | 1 | 2 | 3 | 2 | 2 | 3 | 2 | 3 | 2 | 2 | 4 |
| | 1.0 (1.12) | 1 | 1 | 1 | 1 | 1 | 1 | 1 | 1 | 1 | 1 | 1 | 2 | 2 | 1 | 2 | 1 | 2 | 1 | 1 | 4 |
| | 0.5 (0.56) | 1 | 1 | 1 | 1 | 1 | 1 | — | 1 | 1 | 1 | 1 | 1 | — | 1 | 1 | — | 1 | 1 | 1 | 3 |
| | 0.25 (0.28) | 1 | 3 | — | — | 3 | 2 | — | 4 | — | — | 3 | 4 | 4 | 3 | 5 | 2 | 5 | 5 | 2 | 4 |
| 37 | 8.0 (8.96) | 1 | 3 | 1 | 1 | 5 | 4 | 2 | 4 | 1 | 1 | 4 | 4 | 4 | 4 | 5 | 4 | 4 | 5 | 2 | 3 |
| | 4.0 (4.48) | 1 | — | 1 | 1 | 5 | 4 | 2 | 4 | 1 | 1 | 4 | 4 | 2 | 4 | 4 | 1 | 4 | 5 | 2 | 4 |

TABLE II-continued

| | | Crops | | | | | | | | Weeds | | | | | | | | |
|---|---|---|---|---|---|---|---|---|---|---|---|---|---|---|---|---|---|---|
| Example No. of Compound Tested | Rate of Appln. lbs/acre (kg/ha) | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |

Preemergence

| Example No. of Compound Tested | Rate of Appln. lbs/acre (kg/ha) | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
|---|---|---|---|---|---|---|---|---|---|---|---|---|---|---|---|---|---|---|---|---|---|
| | 2.0 (2.24) | 1 | 2 | 1 | 1 | 4 | 4 | 1 | 2 | 1 | 3 | 2 | 2 | 2 | 5 | 4 | 2 | 4 | 4 | 2 | 4 |
| | 1.0 (1.12) | 1 | 1 | 1 | 1 | 2 | 1 | 1 | 2 | 1 | 1 | 4 | 2 | 2 | 4 | 4 | 1 | 2 | 3 | 2 | 2 |
| | 1.0 (1.12) | 1 | 2 | 1 | 1 | 2 | 2 | 1 | 1 | 1 | 1 | 4 | 3 | 2 | 5 | 3 | 2 | 4 | 2 | 1 | 2 |
| | 0.5 (0.56) | 1 | 2 | 1 | 1 | 2 | 2 | 1 | 1 | 1 | 1 | 2 | 2 | 1 | 3 | 3 | 1 | 2 | 1 | 1 | 2 |
| | 0.25 (0.28) | 1 | 1 | 1 | 1 | 1 | 2 | 1 | 1 | 1 | 1 | 2 | 2 | 1 | 3 | 1 | 1 | 2 | 1 | 1 | 1 |
| 88 | 8.0 (8.96) | | | | | | | | | 5 | 4 | | 5 | 5 | 5 | 5 | 4 | 4 | 5 | 5 | 4 |
| | 4.0 (4.48) | 3 | 4 | 4 | 3 | 4 | 4 | 3 | 5 | 3 | 3 | 4 | 4 | 4 | 5 | 4 | 3 | 5 | 4 | 5 | 5 |
| | 2.0 (2.24) | 3 | 2 | 2 | 2 | 2 | 4 | 2 | 5 | 2 | 3 | 4 | 3 | 3 | 4 | 5 | 2 | 3 | 3 | 5 | 5 |
| | 1.0 (1.12) | 1 | 1 | 1 | 1 | 1 | 2 | 2 | 5 | 1 | 2 | 3 | 2 | 2 | 4 | 4 | 2 | 2 | 3 | 5 | 3 |
| | 1.0 (1.12) | 1 | 1 | 2 | 1 | 1 | 2 | 2 | 3 | 1 | 1 | 4 | 3 | 2 | 4 | 4 | 1 | 2 | 2 | 3 | 2 |
| | 0.5 (0.56) | 1 | 1 | 1 | 1 | 1 | 2 | 2 | 2 | 1 | 1 | 2 | 2 | 1 | 3 | 1 | 1 | 1 | 1 | 2 | 1 |
| | 0.25 (0.28) | 1 | 2 | 1 | 1 | 1 | 2 | 1 | 2 | 1 | 1 | 4 | 3 | 3 | 3 | 2 | 1 | 1 | 1 | 1 | 2 |
| 25 | 8.0 (8.96) | | | | | | | | | 2 | 4 | | 5 | 4 | 5 | 4 | 2 | 4 | 5 | 4 | 5 |
| | 4.0 (4.48) | 2 | 3 | 3 | 3 | 4 | 5 | 2 | 5 | 4 | 4 | 4 | 4 | 3 | 5 | 5 | 4 | 4 | 3 | 4 | 5 |
| | 2.0 (2.24) | 2 | 2 | 2 | 2 | 3 | 4 | 2 | 4 | 2 | 4 | 2 | 3 | 3 | 4 | 5 | 2 | 5 | 3 | 4 | 4 |
| | 1.0 (1.12) | 2 | 1 | 1 | 1 | 2 | 4 | 2 | 3 | 2 | 3 | 2 | 5 | 2 | 5 | 3 | 2 | 4 | 2 | 4 | 3 |
| | 1.0 (1.12) | 1 | 2 | 2 | 2 | 3 | 4 | 2 | 3 | 2 | 1 | 3 | 4 | 2 | 4 | 3 | 2 | 4 | 2 | 3 | 3 |
| | 0.5 (0.56) | 1 | 1 | 1 | 1 | 1 | 1 | 1 | 3 | 1 | 1 | 3 | 4 | 2 | 4 | 3 | 2 | 2 | 2 | 3 | 3 |
| | 0.25 (0.28) | 1 | 1 | 1 | 1 | 1 | 1 | 1 | 1 | 1 | 1 | 1 | 1 | 1 | 1 | 1 | 1 | 2 | 1 | 1 | 1 |
| 6 | 8.0 (8.96) | | | | | | | | | 2 | 4 | | 5 | 4 | 5 | 5 | 4 | 4 | 4 | 5 | 5 |
| | 4.0 (0.48) | 2 | 3 | 2 | 2 | 4 | 4 | 2 | 5 | 4 | 4 | 4 | 4 | 3 | 5 | 5 | 4 | 4 | 4 | 5 | 5 |
| | 2.0 (2.24) | 2 | 2 | 2 | 1 | 3 | 5 | 2 | 4 | 5 | 4 | 5 | 5 | 3 | 4 | 5 | 2 | 5 | 3 | 4 | 4 |
| | 1.0 (1.12) | 1 | 1 | 1 | 1 | 2 | 3 | 1 | 3 | 2 | 3 | 4 | 3 | 2 | 4 | 3 | 2 | 3 | 4 | 5 | 4 |
| | 1.0 (1.12) | 1 | 1 | 1 | 1 | 2 | 1 | 1 | 2 | 1 | 1 | 4 | 4 | 2 | 4 | 3 | 2 | 5 | 4 | 2 | 4 |
| | 0.5 (0.56) | 1 | 1 | 1 | 1 | 1 | 1 | 1 | 1 | 1 | 1 | 3 | 2 | 1 | 3 | 2 | 2 | 3 | 3 | 2 | 2 |
| | 0.25 (0.28) | 1 | 1 | 1 | 1 | 1 | 1 | 1 | 1 | 1 | 1 | 1 | 1 | 1 | 1 | 1 | 1 | 1 | 1 | 1 | 1 |
| 3 | 8.0 (8.96) | | | | | | | | | 4 | 4 | | 5 | 4 | 5 | 4 | 4 | 4 | 4 | 5 | 5 |
| | 4.0 (4.48) | 3 | 4 | 4 | 2 | 3 | 4 | 3 | 4 | 5 | 5 | 5 | 4 | 4 | 5 | 5 | 4 | 5 | 4 | 5 | 5 |
| | 2.0 (2.24) | 3 | 5 | 3 | 4 | 5 | 5 | 2 | 5 | 4 | 4 | 5 | 4 | 3 | 4 | 4 | 4 | 5 | 4 | 5 | 3 |
| | 1.0 (1.12) | 2 | 3 | 1 | 2 | 3 | 4 | 1 | 3 | 2 | 3 | 4 | 3 | 3 | 5 | 3 | 2 | 5 | 3 | 4 | 4 |
| | 1.0 (1.12) | 1 | 1 | 1 | 1 | 1 | 2 | 1 | 1 | 1 | 1 | 2 | 2 | 1 | 4 | 3 | 3 | 3 | 4 | 2 | 3 |
| | 0.5 (0.56) | 1 | 1 | 1 | 1 | 1 | 1 | 1 | 1 | 1 | 1 | 1 | 1 | 1 | 2 | 2 | 1 | 2 | 1 | 2 | 1 |
| 30 | 8.0 (8.96) | | | | | | | | | 2 | 4 | | 4 | 3 | 5 | 4 | 4 | 4 | 3 | 5 | 5 |
| | 4.0 (4.48) | 1 | 1 | 4 | 1 | 2 | 3 | 3 | 3 | 2 | 3 | 4 | 3 | 3 | 4 | 4 | 4 | 4 | 1 | 3 | 3 |
| | 2.0 (2.24) | 1 | 1 | 2 | 2 | 2 | 4 | 1 | 2 | 1 | 2 | 3 | 3 | 2 | 3 | 3 | 2 | 3 | 1 | 3 | 3 |
| | 1.0 (1.12) | 1 | 1 | 2 | 1 | 1 | 2 | 1 | 1 | 1 | 1 | 1 | 3 | 1 | 3 | 2 | 1 | 3 | 1 | 2 | 3 |
| 31 | 8.0 (8.96) | | | | | | | | | 1 | 3 | | 3 | 3 | 5 | 4 | 3 | 4 | 3 | 5 | 4 |
| | 4.0 (4.48) | 1 | 1 | 2 | 3 | 4 | 4 | 2 | 3 | 2 | 3 | 3 | 4 | 4 | 5 | 4 | 3 | 4 | 1 | 3 | 4 |
| | 2.0 (2.28) | 1 | 1 | 2 | 2 | 4 | 4 | 2 | 5 | 2 | 2 | 3 | 4 | 2 | 4 | 4 | 2 | 4 | 1 | 4 | 4 |
| | 1.0 (1.12) | 1 | 1 | 1 | 1 | 1 | 1 | 2 | 4 | 1 | 3 | 1 | 3 | 2 | 4 | 3 | 2 | 3 | 1 | 3 | 3 |
| | 1.0 (1.12) | 1 | 1 | 1 | 1 | 2 | 2 | 1 | 3 | 1 | 2 | 2 | 2 | 2 | 3 | 3 | 2 | 2 | 1 | 3 | 3 |
| | 0.5 (0.56) | 1 | 1 | 1 | 1 | 1 | 1 | 1 | 2 | 1 | 2 | 4 | 2 | 2 | 4 | 1 | 1 | 3 | 1 | 3 | 2 |
| | 0.25 (0.28) | 1 | 1 | 1 | 1 | 1 | 1 | 1 | 1 | 1 | 1 | 1 | 1 | 1 | 2 | 1 | 1 | 1 | 1 | 1 | 1 |
| 36 | 8.0 (8.96) | 4 | 4 | 4 | 2 | 3 | 4 | 4 | 4 | 4 | 4 | 5 | 5 | 4 | 5 | 5 | 5 | 5 | 5 | 4 | 5 |
| | 4.0 (4.48) | 3 | 3 | 2 | 1 | 3 | 4 | 2 | 5 | 3 | 5 | 4 | 4 | 1 | 5 | 4 | 3 | 5 | 4 | 3 | 5 |
| | 2.0 (2.24) | | | | | | | | | 4 | 4 | | 4 | | 5 | 5 | | 4 | | 2 | 5 |

TABLE II-continued

| Example No. of Compound Tested | Rate of Appln. lbs/acre (kg/ha) | Crops | | | | | | | | | Preemergence Weeds | | | | | | | | | |
|---|---|---|---|---|---|---|---|---|---|---|---|---|---|---|---|---|---|---|---|---|
| | | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
| | 1.0 (1.12) | 1 | 1 | 2 | 1 | 1 | 1 | 2 | 2 | 2 | 3 | 4 | 4 | 1 | 4 | 4 | 1 | 3 | 1 | 2 | 3 |
| | 1.0 (1.12) | 2 | 3 | 2 | 1 | 3 | 1 | 1 | 3 | 2 | 2 | 4 | 4 | 3 | 4 | 3 | 2 | 5 | 2 | 3 | 4 |
| | 0.5 (0.56) | 1 | 1 | 1 | 1 | 2 | 1 | 1 | 3 | 2 | 3 | 2 | 3 | 2 | 3 | 2 | 2 | 4 | 1 | 1 | 5 |
| | 0.25 (0.28) | 1 | 1 | 1 | 1 | 3 | 2 | 1 | 2 | 1 | 4 | 1 | 2 | 1 | 3 | 3 | 1 | 3 | 1 | 1 | 1 |
| 5 | 8.0 (8.96) | | | | | | | | | 4 | 4 | 5 | 5 | 2 | 5 | 5 | 4 | 4 | 5 | 5 | 5 |
| | 4.0 (4.48) | 3 | 4 | 4 | 3 | 4 | 5 | 2 | 4 | 4 | 4 | 5 | 5 | 5 | 5 | 5 | 4 | 5 | 5 | 5 | 5 |
| | 2.0 (2.24) | 4 | 5 | 4 | 3 | 5 | 5 | 2 | 5 | 4 | 4 | 5 | 5 | 5 | 5 | 5 | 3 | 5 | 4 | 5 | 5 |
| | 1.0 (1.12) | 1 | 2 | 2 | 1 | 5 | 4 | 2 | 3 | 4 | 3 | 4 | 5 | 4 | 5 | 4 | 3 | 4 | 3 | 4 | 5 |
| 5 | 0.5 (0.56) | 1 | 1 | 1 | 1 | 4 | 4 | 2 | 5 | 4 | 2 | 4 | 5 | 3 | 5 | 4 | 3 | 4 | 4 | 4 | 3 |
| | 0.25 (0.28) | 1 | 1 | 1 | 1 | 3 | 3 | 1 | 2 | 3 | 3 | 4 | 3 | 2 | 3 | 2 | 1 | 3 | 3 | 1 | 3 |
| 24 | 8.0 (8.96) | | | | | | | | | 5 | 1 | 4 | 1 | 2 | 1 | 2 | 1 | 1 | | 1 | 1 |
| | 4.0 (4.48) | 5 | 5 | 4 | 3 | 5 | 5 | 3 | 5 | 4 | 5 | 5 | 5 | 5 | 5 | 5 | 5 | 5 | 5 | 5 | 5 |
| | 2.0 (2.24) | 2 | 2 | 2 | 2 | 3 | 3 | 1 | 2 | 2 | 4 | 5 | 4 | 4 | 5 | 4 | 2 | 5 | 2 | 5 | 5 |
| | 1.0 (1.12) | 1 | 4 | 1 | 1 | 1 | 1 | 3 | 1 | 2 | 2 | 4 | 4 | 2 | 5 | 5 | 5 | 4 | 4 | 4 | 4 |
| | 0.5 (0.56) | 2 | 4 | 2 | 3 | 4 | 4 | 3 | 5 | 4 | 3 | 4 | 4 | 4 | 5 | 5 | 5 | 5 | 4 | 5 | 5 |
| | 0.25 (0.28) | 1 | 3 | 1 | 1 | 1 | 1 | 1 | 1 | 1 | 1 | 3 | 2 | 1 | 4 | 2 | 1 | 2 | 1 | 3 | 3 |
| 8 | 4.0 (4.48) | 3 | 3 | 3 | 3 | 5 | 5 | 3 | 5 | 4 | 3 | 5 | 5 | 3 | 5 | 5 | 4 | 5 | 5 | 5 | 5 |
| | 2.0 (2.24) | 2 | 1 | 2 | 2 | 2 | 2 | 3 | 2 | 2 | 3 | 5 | 4 | 3 | 5 | 3 | 2 | 3 | 3 | 2 | 3 |
| | 1.0 (1.12) | 1 | 1 | 1 | 1 | 1 | 1 | 1 | 1 | 1 | 1 | 1 | 2 | 2 | 2 | 1 | 1 | 1 | 1 | 2 | 1 |
| | 0.5 (0.56) | 1 | 1 | 2 | 1 | 2 | 2 | 2 | 1 | 2 | 1 | 2 | 2 | 2 | 2 | 2 | 2 | 2 | 1 | 2 | 2 |
| | 0.25 (0.28) | 1 | 1 | 1 | 1 | 1 | 1 | 1 | 1 | 1 | 1 | 1 | 2 | 1 | 3 | 1 | 2 | 1 | 1 | 1 | 1 |
| 39 | 8.0 (8.96) | | | | | | | | | 4 | 4 | 4 | 4 | 4 | 5 | 4 | 2 | 5 | 3 | 3 | 5 |
| | 4.0 (4.48) | 2 | 3 | 2 | 2 | 5 | 5 | 2 | 5 | 4 | 4 | 5 | 5 | 4 | 5 | 5 | 4 | 5 | 2 | 5 | 5 |
| | 2.0 (2.24) | 1 | 1 | 1 | 1 | 3 | 4 | 1 | 5 | 3 | 3 | 4 | 4 | 3 | 5 | 3 | 2 | 4 | 1 | 2 | 2 |
| | 1.0 (1.12) | 1 | 1 | 1 | 1 | 2 | 2 | 2 | 4 | 2 | 3 | 3 | 3 | 2 | 4 | 2 | 2 | 4 | 1 | 2 | 3 |
| | 0.5 (0.56) | 1 | 1 | 1 | 1 | 2 | 2 | 2 | 2 | 1 | 1 | 3 | 2 | 2 | 2 | 2 | 2 | 2 | 1 | 1 | 1 |
| | 0.25 (0.28) | 1 | 1 | 1 | 1 | 1 | 1 | 1 | 1 | 1 | 1 | 2 | 1 | 1 | 3 | 1 | 1 | 1 | 1 | 1 | 2 |
| 84 | 8.0 (8.96) | | | | | | | | | 4 | 4 | 5 | 5 | 4 | 5 | 5 | 4 | 5 | 5 | 5 | 5 |
| 33 | 8.0 (8.96) | 3 | 5 | 5 | 4 | 5 | 5 | 3 | 5 | 5 | 4 | 5 | 5 | 5 | 5 | 5 | 4 | 5 | 3 | 4 | 5 |
| | 4.0 (4.48) | 3 | 3 | 3 | 3 | 5 | 4 | 2 | 5 | 5 | 3 | 5 | 4 | 5 | 5 | 5 | 2 | 5 | 3 | 3 | 4 |
| | 2.0 (2.24) | 1 | 1 | 2 | 1 | 2 | 4 | 2 | 5 | 3 | 1 | 3 | 4 | 3 | 4 | 3 | 1 | 4 | 2 | 2 | 3 |
| | 1.0 (1.12) | 1 | 3 | 4 | 1 | 2 | 3 | 3 | 5 | 3 | 2 | 2 | 3 | 2 | 2 | 2 | 4 | 4 | 2 | 4 | 4 |
| | 1.0 (1.12) | 3 | 1 | 2 | 1 | 2 | 2 | 2 | 4 | 2 | 2 | 2 | 3 | 2 | 3 | 2 | 1 | 3 | 1 | 3 | 3 |
| | 0.5 (0.56) | 1 | 1 | 1 | 1 | 1 | 1 | 1 | 1 | 1 | 1 | 1 | 2 | 1 | 1 | 1 | 1 | 1 | 1 | 1 | 1 |
| | 0.25 (0.28) | | | | | | | | | | | | | | | | | | | | |
| 83 | 8.0 (8.96) | 3 | 5 | 5 | 3 | 5 | 5 | 3 | 5 | 5 | 4 | 5 | 5 | 5 | 5 | 5 | 4 | 5 | 5 | 5 | 5 |
| | 4.0 (4.48) | 1 | 3 | 4 | 2 | 2 | 4 | 2 | 5 | 3 | 3 | 5 | 5 | 5 | 5 | 5 | 3 | 5 | 5 | 4 | 3 |
| | 2.0 (2.24) | 1 | 1 | 2 | 1 | 2 | 3 | 1 | 4 | 2 | 2 | 3 | 4 | 3 | 4 | 3 | 3 | 3 | 4 | 3 | 3 |
| | 1.0 (1.12) | 1 | 4 | 4 | 1 | 2 | 2 | 2 | 4 | 3 | 2 | 3 | 4 | 2 | 4 | 3 | 1 | 3 | 2 | 3 | 3 |
| | 1.0 (1.12) | 1 | 1 | 2 | 1 | 1 | 2 | 2 | 2 | 2 | 2 | 2 | 4 | 4 | 4 | 3 | 3 | 3 | 2 | 1 | 1 |
| | 0.5 (0.56) | 1 | 1 | 1 | 1 | 1 | 1 | 1 | 2 | 1 | 1 | 3 | 4 | 1 | 4 | 3 | 1 | 2 | 1 | 3 | 3 |
| | 0.25 (0.28) | 3 | 1 | 1 | 1 | 1 | 1 | 1 | 2 | 1 | 1 | 3 | 3 | 3 | 3 | 2 | 1 | 1 | 2 | 2 | 3 |

TABLE II-continued

|  |  | Crops | | | | | | | | Preemergence | Weeds | | | | | | | | |
|---|---|---|---|---|---|---|---|---|---|---|---|---|---|---|---|---|---|---|---|
| Example No. of Compound Tested | Rate of Appln. lbs/acre (kg/ha) | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
| 85 | 0.125 (0.14) | 1 | 1 |  |  |  |  |  | 2 | 1 | 1 | 2 | 2 | 1 | 2 | 2 | 1 | 2 | 1 | 1 | 1 |
| 86 | 0.0625 (0.07) | 1 | 1 |  |  |  |  |  | 2 | 1 | 1 | 1 | 2 | 1 | 2 | 1 | 1 | 1 | 1 | 1 | 1 |
| 95 | 8.0 (8.96) |  |  |  |  |  |  |  |  |  | 3 |  | 2 | 3 | 2 | 1 | 1 | 1 | 1 | 1 | 2 |
|  | 8.0 (8.96) |  |  |  |  |  |  |  |  | 1 | 1 |  | 2 | 1 | 2 | 1 | 1 | 1 | 1 | 1 | 2 |
|  | 8.0 (8.96) |  |  |  |  |  |  |  | 5 | 5 | 4 | 5 | 5 | 5 | 5 | 5 | 5 | 5 | 5 | 5 | 5 |
|  | 4.0 (4.48) | 4 | 5 | 4 | 4 | 5 | 5 | 4 | 5 | 5 | 4 | 5 | 5 | 5 | 5 | 5 | 4 | 5 | 5 | 5 | 5 |
|  | 2.0 (2.24) | 3 | 5 | 4 | 4 | 5 | 4 | 4 | 5 | 5 | 4 | 4 | 4 | 5 | 5 | 5 | 2 | 5 | 4 | 5 | 5 |
|  | 1.0 (1.12) | 2 | 4 | 3 | 2 | 5 | 5 | 2 | 4 | 4 | 3 | 5 | 4 | 4 | 5 | 4 | 3 | 5 | 5 | 5 | 5 |
|  | 1.0 (1.12) | 2 | 3 | 3 | 1 | 3 | 4 | 2 | 4 | 2 | 1 | 4 | 4 | 4 | 4 | 4 | 2 | 5 | 3 | 3 | 2 |
|  | 0.5 (0.56) | 1 | 1 | 5 | 1 | 4 | 5 | 2 | 4 | 1 | 1 | 5 | 3 | 5 | 4 | 3 | 3 | 4 | 3 | 3 | 4 |
| 95 | 0.25 (0.28) | 1 | 1 | 1 | 1 | 3 | 3 | 2 | 3 | 3 | 1 | 4 | 2 | 4 | 2 | 3 | 2 | 4 | 2 | 3 | 1 |
|  | 0.25 (0.28) | 1 | 1 | 1 | 1 | 3 | 3 | 2 | 1 | 1 | 1 | 2 | 2 | 3 | 2 | 3 | 4 | 5 | 1 | 1 | 1 |
|  | 0.125 (0.14) | 1 | 1 | 1 | 1 | 2 | 1 | 2 | 1 | 1 | 1 | 2 | 1 | 2 | 2 | 1 | 2 | 1 | 1 | 1 | 1 |
|  | 0.0625 (0.07) | 1 | 1 | 1 | 1 | 1 | 1 | 1 | 1 | 1 |  |  | 2 | 1 | 1 | 1 | 1 | 1 | 1 | 1 | 1 |
| 32 | 8.0 (8.96) |  |  |  |  |  |  |  | 4 | 4 | 4 | 4 | 5 | 4 | 5 | 4 | 4 | 5 | 5 | 4 | 4 |
|  | 4.0 (4.48) | 3 | 2 | 2 | 2 | 5 | 4 | 3 | 4 | 3 | 4 | 4 | 5 | 3 | 4 | 2 | 2 | 5 | 5 | 5 | 5 |
|  | 2.0 (2.24) | 1 | 1 | 1 | 1 | 3 | 4 | 3 | 5 | 1 | 2 | 3 | 4 | 3 | 5 | 3 | 2 | 4 | 3 | 4 | 4 |
|  | 1.0 (1.12) | 1 | 2 | 2 | 1 | 3 | 4 | 2 | 4 | 1 | 1 | 3 | 4 | 3 | 4 | 4 | 2 | 5 | 3 | 4 | 3 |
|  | 1.0 (1.12) | 1 | 2 | 2 | 1 | 3 | 4 | 2 | 4 | 1 | 1 | 3 | 3 | 3 | 4 | 2 | 2 | 3 | 3 | 3 | 2 |
|  | 0.5 (0.56) | 1 | 1 | 1 | 1 | 2 | 2 | 1 | 1 | 1 | 1 | 2 | 2 | 2 | 3 | 3 | 1 | 3 | 1 | 1 | 1 |
|  | 0.25 (0.28) | 1 | 1 | 1 | 1 | 1 | 1 | 1 | 1 | 1 |  |  | 1 | 1 | 2 | 1 | 1 | 1 | 1 | 1 | 1 |
| 4 | 8.0 (8.96) |  |  |  |  |  |  |  | 5 | 5 | 5 | 5 | 5 | 5 | 5 | 5 | 5 | 5 | 5 | 5 | 5 |
|  | 4.0 (4.48) | 3 | 4 | 4 | 2 | 4 | 5 | 5 | 5 | 4 | 5 | 5 | 5 | 5 | 5 | 5 | 4 | 5 | 5 | 5 | 5 |
|  | 2.0 (2.24) | 3 | 5 | 3 | 3 | 4 | 4 | 3 | 5 | 5 | 4 | 5 | 4 | 5 | 5 | 5 | 3 | 5 | 5 | 5 | 5 |
|  | 1.0 (1.12) | 2 | 2 | 2 | 1 | 2 | 5 | 4 | 3 | 2 | 2 | 4 | 3 | 4 | 4 | 3 | 3 | 4 | 3 | 4 | 4 |
|  | 1.0 (1.12) | 1 | 1 | 1 | 2 | 2 | 4 | 2 | 2 | 1 | 1 | 2 | 3 | 2 | 4 | 3 | 1 | 3 | 2 | 3 | 2 |
|  | 0.5 (0.56) | 1 | 1 | 1 | 1 | 1 | 1 | 1 | 1 | 1 | 1 | 1 | 1 | 1 | 2 | 1 | 1 | 1 | 1 | 1 | 1 |
|  | 0.25 (0.28) | 1 | 1 | 1 | 1 | 1 | 1 | 1 | 1 | 1 | 1 | 1 | 1 | 1 | 1 | 1 | 1 | 1 | 1 | 1 | 1 |
| 20 | 8.0 (8.96) |  |  |  |  |  |  |  | 5 | 5 | 5 | 5 | 5 | 5 | 5 | 5 | 5 | 5 | 5 | 5 | 5 |
|  | 4.0 (4.48) | 3 | 5 | 3 | 4 | 5 | 5 | 5 | 5 | 4 | 4 | 5 | 4 | 5 | 5 | 5 | 4 | 5 | 5 | 5 | 5 |
|  | 2.0 (2.24) | 3 | 2 | 4 | 2 | 4 | 4 | 4 | 5 | 3 | 4 | 5 | 4 | 5 | 4 | 4 | 3 | 4 | 4 | 5 | 5 |
|  | 1.0 (1.12) | 2 | 3 | 3 | 2 | 2 | 5 | 3 | 2 | 2 | 2 | 5 | 3 | 4 | 3 | 4 | 3 | 5 | 5 | 5 | 4 |
|  | 1.0 (1.12) | 1 | 1 | 4 | 1 | 2 | 3 | 2 | 1 | 1 | 1 | 4 | 2 | 3 | 2 | 2 | 3 | 3 | 2 | 2 | 2 |
|  | 0.5 (0.56) | 1 | 1 | 1 | 1 | 1 | 2 | 2 | 2 | 2 | 2 | 1 | 2 | 2 | 2 | 1 | 1 | 2 | 1 | 1 | 1 |
|  | 0.25 (0.28) | 1 | 1 | 1 | 1 | 1 | 1 |  |  | 1 | 1 |  | 1 | 1 | 1 | 1 | 1 | 1 | 1 | 1 | 1 |
| 92 | 8.0 (8.96) |  |  |  |  |  |  |  | 5 | 5 | 4 | 5 | 5 | 5 | 5 | 5 | 5 | 5 | 5 | 5 | 5 |
|  | 4.0 (4.48) | 4 | 4 | 3 | 2 | 5 | 4 | 2 | 5 | 4 | 3 | 4 | 5 | 4 | 5 | 5 | 3 | 5 | 4 | 5 | 5 |
|  | 2.0 (2.24) | 5 | 4 | 4 | 2 | 5 | 5 | 4 | 5 | 3 | 4 | 5 | 5 | 4 | 5 | 5 | 3 | 5 | 4 | 3 | 3 |
|  | 1.0 (1.12) | 3 | 3 | 4 | 2 | 3 | 3 | 4 | 3 | 2 | 2 | 3 | 3 | 3 | 3 | 2 | 3 | 3 | 2 | 3 | 4 |
|  | 1.0 (1.12) | 1 | 1 | 1 | 1 | 2 | 2 | 1 | 1 | 1 | 1 | 2 | 2 | 3 | 3 | 1 | 2 | 2 | 2 | 2 | 2 |
|  | 0.25 (0.28) | 1 | 1 | 1 | 1 | 1 | 2 | 1 | 1 | 2 | 1 | 1 | 1 | 1 | 1 | 1 | 1 | 1 | 1 | 1 | 1 |
| 93 | 0.125 (0.14) |  |  |  |  |  |  |  |  |  |  |  |  |  |  |  |  |  |  |  |  |
|  | 0.0625 (0.07) |  |  |  |  |  |  |  |  |  |  |  |  |  |  |  |  |  |  |  |  |
|  | 8.0 (8.96) |  |  |  |  |  |  |  | 5 | 4 | 4 | 4 | 5 | 5 | 5 | 5 | 4 | 5 | 4 | 5 | 5 |
|  | 4.0 (4.48) | 1 | 4 | 2 | 2 | 5 | 4 | 2 | 5 | 2 | 2 | 4 | 4 | 4 | 4 | 3 | 2 | 3 | 2 | 3 | 3 |
|  | 2.0 (2.24) | 1 | 4 | 1 | 1 | 4 | 3 | 2 | 2 | 2 | 2 | 4 | 3 | 3 | 3 | 2 | 2 | 5 | 4 | 3 | 1 |
|  | 1.0 (1.12) | 1 | 3 | 1 | 1 | 4 | 4 | 2 | 1 | 1 | 1 | 5 | 2 | 1 | 3 | 1 | 1 | 1 | 2 | 1 | 1 |
| 94 | 8.0 (8.96) | 1 | 1 | 2 | 2 |  | 4 | 2 | 5 | 2 | 4 |  | 4 | 5 | 4 | 5 | 5 | 5 | 4 | 5 | 5 |
|  | 4.0 (4.48) | 1 | 4 | 1 | 1 | 5 | 3 | 2 | 2 | 2 | 2 | 4 | 4 | 4 | 3 | 3 | 4 | 4 | 2 | 3 | 3 |
|  | 2.0 (2.24) | 2 | 4 | 2 | 1 | 4 | 4 | 2 | 2 | 1 | 2 | 4 | 3 | 4 | 2 | 2 | 2 | 2 | 2 | 1 | 1 |
|  | 1.0 (1.12) | 1 | 3 | 1 | 1 | 4 |  | 2 | 1 | 1 | 1 | 2 | 1 | 4 | 1 | 1 | 1 | 1 |  |  |  |
|  | 8.0 (8.96) |  |  |  |  |  |  | 2 | 1 | 4 | 5 |  |  | 5 | 5 | 5 | 5 | 5 | 5 | 2 | 5 |

TABLE II-continued

Preemergence

| Example No. of Compound Tested | Rate of Appln. lbs/acre (kg/ha) | Crops | | | | | | | | | Weeds | | | | | | | | | |
|---|---|---|---|---|---|---|---|---|---|---|---|---|---|---|---|---|---|---|---|---|
| | | Corn | Cotton | Soybean | Wheat | Alfalfa | Sugar Beet | Rice | Cucumber | Tomato | Barnyard Grass | Lambs-quarter | Large Crab-grass | Mus-tard | Pig-weed | Fox-tail | Wild Oat | Velvet-leaf | Jimson-weed | Morning-glory | Zinnia |
| | 4.0 (4.48) | 2 | 3 | 4 | 2 | 4 | 5 | 3 | 5 | 3 | 4 | 5 | 5 | 5 | 5 | 5 | 3 | 5 | 5 | 3 | 5 |
| | 2.0 (2.24) | 2 | 5 | 4 | 1 | 4 | 4 | 2 | 5 | 4 | 5 | 5 | 5 | 5 | 5 | 5 | 2 | 5 | 5 | 4 | 5 |
| | 1.0 (1.12) | 1 | 3 | 4 | 1 | 4 | 4 | 2 | 5 | 3 | 4 | 5 | 4 | 4 | 3 | 5 | 1 | 3 | 4 | 3 | 5 |
| 98 | 8.0 (8.96) | | | | | | | | | 5 | 4 | | 5 | 4 | 4 | 5 | 5 | 5 | | | 5 |
| | 4.0 (4.48) | 3 | 4 | 4 | 3 | 5 | 5 | 3 | 5 | 5 | 4 | 5 | 5 | 5 | 5 | 5 | 3 | 5 | 4 | 4 | 5 |
| | 2.0 (2.24) | 2 | 4 | 3 | 2 | 5 | 4 | 2 | 5 | 5 | 3 | 5 | 5 | 5 | 5 | 5 | 2 | 5 | 5 | 5 | 5 |
| | 1.0 (1.12) | 1 | 3 | 2 | 1 | 5 | 5 | 3 | 5 | 5 | 4 | 5 | 5 | 5 | 5 | 5 | 1 | 5 | 5 | 5 | 5 |
| | 1.0 (1.12) | 3 | 4 | 5 | 5 | 5 | 5 | 5 | 5 | 5 | 5 | 5 | 5 | 5 | 5 | 4 | 4 | 5 | 5 | 5 | 5 |
| | 0.5 (0.56) | 3 | 5 | 3 | 4 | 5 | 5 | 2 | 5 | 4 | 3 | 4 | 5 | 5 | 5 | 5 | 5 | 5 | 5 | 5 | 5 |
| | 0.25 (0.28) | 1 | 3 | 3 | 2 | 4 | 5 | 2 | 5 | 4 | 3 | 4 | 5 | 5 | 5 | 4 | 4 | 5 | 5 | 5 | 5 |
| | 0.25 (0.28) | 1 | 3 | 2 | 2 | 4 | 4 | 2 | 5 | 3 | 2 | 4 | 5 | 4 | 5 | 5 | 2 | 5 | 5 | 5 | 5 |
| | 0.125 (0.14) | 1 | 2 | 1 | 2 | 4 | 4 | 2 | 5 | 3 | 1 | 4 | 5 | 4 | 5 | 4 | 1 | 4 | 3 | 3 | 3 |
| | 0.0625 (0.07) | 1 | 1 | 1 | 1 | 2 | 4 | 1 | 2 | 2 | 1 | 3 | 3 | 3 | 3 | 2 | 1 | 2 | 2 | 2 | 1 |
| 99 | 8.0 (8.96) | | | | | | | | | 5 | 4 | | 5 | 5 | 5 | 5 | 5 | 5 | | | 5 |
| | 4.0 (4.48) | 3 | 5 | 4 | 3 | 5 | 5 | 4 | 5 | 5 | 4 | 5 | 5 | 5 | 5 | 5 | 5 | 5 | 4 | 4 | 5 |
| | 2.0 (2.24) | 2 | 4 | 1 | 1 | 5 | 5 | 2 | 5 | 4 | 4 | 4 | 5 | 5 | 5 | 5 | 5 | 5 | 4 | 4 | 5 |
| | 1.0 (1.12) | 1 | 3 | 2 | 2 | 5 | 5 | 2 | 5 | 5 | 3 | 5 | 5 | 5 | 5 | 5 | 4 | 5 | 4 | 5 | 5 |
| | 1.0 (1.12) | 2 | 4 | 3 | 2 | 5 | 5 | 2 | 5 | 5 | 4 | 5 | 5 | 5 | 5 | 5 | 4 | 5 | 4 | 4 | 5 |
| | 0.5 (0.56) | 2 | 2 | 2 | 2 | 5 | 4 | 2 | 5 | 5 | 2 | 5 | 5 | 5 | 5 | 5 | 2 | 4 | 4 | 4 | 4 |
| | 0.25 (0.28) | 1 | 2 | 3 | 1 | 4 | 4 | 2 | 5 | 4 | 1 | 5 | 4 | 5 | 4 | 3 | 1 | 3 | 3 | 2 | 3 |
| | 0.25 (0.28) | 1 | 2 | 2 | 1 | 2 | 4 | 1 | 4 | 2 | 2 | 4 | 2 | 3 | 4 | 3 | 1 | 3 | 3 | 3 | 3 |
| | 0.125 (0.14) | 1 | 2 | 2 | 1 | 2 | 4 | 1 | 2 | 1 | 1 | 3 | 2 | 2 | 3 | 2 | 1 | 2 | 2 | 2 | 2 |
| | 0.0625 (0.07) | 1 | 1 | 1 | 1 | 2 | 2 | 1 | 1 | 1 | 1 | 2 | 1 | 1 | 2 | 1 | 1 | 2 | 2 | 1 | 1 |
| 100 | 8.0 (8.96) | | | | | | | | | 5 | 5 | | 5 | 5 | 5 | 5 | 5 | 5 | | | 5 |
| | 4.0 (4.48) | 1 | 4 | 4 | 3 | 5 | 5 | 3 | 5 | 5 | 4 | 5 | 5 | 5 | 5 | 5 | 5 | 5 | 5 | 5 | 5 |
| | 2.0 (2.24) | 1 | 4 | 3 | 3 | 5 | 5 | 3 | 5 | 5 | 4 | 5 | 5 | 5 | 5 | 4 | 3 | 5 | 4 | 4 | 4 |
| | 1.0 (1.12) | 1 | 4 | 3 | 2 | 5 | 5 | 2 | 3 | 3 | 2 | 5 | 4 | 5 | 5 | 4 | 2 | 5 | 4 | 5 | 4 |
| | 1.0 (1.12) | 1 | 2 | 2 | 1 | 2 | 4 | 1 | 2 | 2 | 1 | 4 | 4 | 4 | 4 | 4 | 2 | 4 | 4 | 4 | 3 |
| | 0.5 (0.56) | 1 | 2 | 1 | 1 | 4 | 4 | 1 | 3 | 2 | 1 | 4 | 3 | 3 | 4 | 3 | 1 | 3 | 3 | 3 | 3 |
| | 0.25 (0.28) | 1 | 1 | 1 | 1 | 2 | 3 | 1 | 2 | 1 | 1 | 3 | 2 | 3 | 3 | 2 | 1 | 3 | 2 | 2 | 2 |
| | 0.25 (0.28) | 1 | 2 | 1 | 1 | 2 | 4 | 2 | 2 | 1 | 1 | 4 | 2 | 2 | 3 | 2 | 1 | 2 | 2 | 2 | 1 |
| | 0.125 (0.14) | 1 | 1 | 1 | 1 | 2 | 3 | 1 | 1 | 1 | 1 | 2 | 1 | 1 | 2 | 1 | 1 | 2 | 1 | 1 | 1 |
| | 0.0625 (0.07) | 1 | 1 | 1 | 1 | 2 | 2 | 1 | 1 | 1 | 1 | 2 | 1 | 1 | 2 | 1 | 1 | 1 | 1 | 1 | 1 |
| 101 | 8.0 (8.96) | | | | | | | | | 5 | 4 | | 5 | 5 | 5 | 5 | 5 | 5 | | | 5 |
| | 4.0 (4.48) | 2 | 4 | 4 | 3 | 5 | 5 | 4 | 5 | 4 | 4 | 5 | 5 | 5 | 5 | 5 | 5 | 5 | 5 | 5 | 5 |
| | 2.0 (2.24) | 1 | 3 | 2 | 3 | 5 | 5 | 2 | 4 | 3 | 3 | 5 | 5 | 5 | 5 | 5 | 4 | 5 | 5 | 4 | 4 |
| | 1.0 (1.12) | 1 | 3 | 2 | 1 | 4 | 4 | 2 | 4 | 4 | 1 | 5 | 4 | 4 | 5 | 4 | 2 | 4 | 4 | 4 | 4 |
| | 1.0 (1.12) | 1 | 2 | 2 | 2 | 4 | 5 | 2 | 4 | 4 | 3 | 5 | 5 | 5 | 5 | 5 | 2 | 5 | 3 | 3 | 4 |
| | 0.5 (0.56) | 1 | 1 | 1 | 1 | 5 | 4 | 2 | 2 | 3 | 1 | 5 | 4 | 4 | 4 | 3 | 1 | 4 | 3 | 2 | 4 |
| | 0.25 (0.28) | 1 | 1 | 1 | 2 | 5 | 3 | 2 | 2 | 2 | 1 | 5 | 3 | 3 | 4 | 2 | 1 | 3 | 2 | 2 | 3 |
| | 0.25 (0.28) | 1 | 1 | 1 | 1 | 2 | 3 | 1 | 2 | 2 | 1 | 4 | 3 | 3 | 4 | 2 | 1 | 3 | 2 | 2 | 3 |
| | 0.125 (0.14) | 1 | 1 | 1 | 1 | 2 | 3 | 1 | 2 | 1 | 1 | 3 | 3 | 2 | 3 | 2 | 1 | 2 | 2 | 2 | 2 |
| | 0.0625 (0.07) | 1 | 1 | 1 | 1 | 2 | 2 | 1 | 1 | 1 | 1 | 3 | 2 | 1 | 2 | 1 | 1 | 1 | 1 | 1 | 1 |

TABLE III

Postemergence

| Example No. of Compound Tested | Rate of Appln. lbs/acre (kg/ha) | Tomato | Large Crab-grass | Pig-weed | Fox-tail | Velvet-leaf | Morning-glory | Zinnia | Barn-yard Grass | Mus-tard | Wild Oats |
|---|---|---|---|---|---|---|---|---|---|---|---|
| 65 | 8.0 (8.96) | 3 | 3 | 5 | 2 | 2 | 2 | 5 | 1 | 5 | 1 |
|  | 4.0 (4.48) | 4 | 3 | 5 | 2 | 3 | 3 | 4 | 1 | 5 | 1 |
|  | 2.0 (2.24) | 2 | 3 | 5 | 2 | 2 | 3 | 3 | 1 | 5 | 1 |
|  | 1.0 (1.12) | 2 | 2 | 5 | 2 | 2 | 3 | 3 | 1 | 5 | 1 |
|  | 1.0 (1.12) | 4 | 3 | 5 | 2 | 3 | 3 | 4 | 1 | 5 | 1 |
|  | 0.5 (0.56) | 4 | 3 | 4 | 2 | 2 | 3 | 4 | 1 | 4 | 1 |
|  | 0.25 (0.28) | 3 | 2 | 5 | 2 | 2 | 3 | 4 | 1 | 4 | 1 |
|  | 0.25 (0.28) | 2 | 2 | 4 | 2 | 2 | 2 | 3 | 1 | 4 | 1 |
|  | 0.125 (0.14) | 1 | 2 | 2 | 2 | 2 | 2 | 4 | 1 | 3 | 1 |
|  | 0.0625 (0.07) | 1 | 2 | 2 | 1 | 1 | 1 | 2 | 1 | 3 | 1 |
| 63 | 8.0 (8.96) | 5 | 5 | 5 | 5 | 4 | 5 | 5 | 4 | 5 | 3 |
|  | 4.0 (4.48) | 5 | 4 | 5 | 4 | 5 | 5 | 4 | 3 | 4 | 3 |
|  | 2.0 (2.24) | 4 | 4 | 4 | 4 | 4 | 5 | 5 | 3 | 4 | 3 |
|  | 1.0 (1.12) | 4 | 4 | 4 | 3 | 4 | 4 | 4 | 3 | 4 | 3 |
|  | 1.0 (1.12) | 5 | 4 | 4 | 3 | 4 | 4 | 4 | 3 | 4 | 2 |
|  | 0.5 (0.56) | 5 | 3 | 4 | 3 | 4 | 3 | 4 | 2 | 4 | 2 |
|  | 0.25 (0.28) | 4 | 3 | 3 | 3 | 3 | 3 | 3 | 3 | 4 | 2 |
|  | 0.25 (0.28) | 4 | 3 | 4 | 2 | 4 | 3 | 4 | 2 | 4 | 2 |
|  | 0.125 (0.14) | 3 | 2 | 4 | 2 | 4 | 2 | 3 | 2 | 4 | 2 |
|  | 0.0625 (0.07) | 2 | 2 | 4 | 2 | 2 | 2 | 2 | 1 | 3 | 2 |
| 62 | 8.0 (8.96) | 3 | 3 | 5 | 3 | 2 | 2 | 2 | 1 | 5 | 1 |
|  | 4.0 (4.48) | 4 | 4 | 5 | 4 | 5 | 3 | 4 | 3 | 5 | 1 |
|  | 2.0 (2.24) | 3 | 4 | 5 | 4 | 4 | 3 | 5 | 2 | 5 | 1 |
|  | 1.0 (1.12) | 4 | 4 | 5 | 3 | 3 | 3 | 5 | 1 | 5 | 1 |
|  | 1.0 (1.12) | 3 | 3 | 5 | 3 | 3 | 3 | 5 | 1 | 5 | 1 |
|  | 0.5 (0.56) | 3 | 3 | 5 | 3 | 3 | 3 | 4 | 1 | 5 | 1 |
|  | 0.25 (0.28) | 3 | 3 | 4 | 3 | 2 | 2 | 5 | 1 | 5 | 1 |
|  | 0.25 (0.28) | 2 | 2 | 3 | 2 | 2 | 2 | 3 | 1 | 4 | 1 |
|  | 0.125 (0.14) | 2 | 2 | 2 | 2 | 2 | 2 | 3 | 2 | 3 | 1 |
|  | 0.0625 (0.07) | 1 | 2 | 2 | 2 | 2 | 2 | 2 | 1 | 4 | 1 |
| 14 | 8.0 (8.96) | 1 | 1 | 3 | 1 | 2 | 1 | 2 | 1 | 3 | 1 |
| 23 | 8.0 (8.96) | 1 | 1 | 1 | 1 | 1 | 1 | 1 | 1 | 1 | 1 |
| 61 | 8.0 (8.96) | 4 | 4 | 5 | 3 | 3 | 3 | 4 | 2 | 4 | 1 |
|  | 4.0 (4.48) | 4 | 3 | 5 | 3 | 3 | 3 | 3 | 2 | 4 | 2 |
|  | 2.0 (2.24) | 4 | 4 | 5 | 3 | 3 | 3 | 3 | 2 | 4 | 2 |
|  | 1.0 (1.12) | 3 | 3 | 4 | 2 | 4 | 3 | 4 | 2 | 4 | 2 |
|  | 1.0 (1.12) | 4 | 4 | 4 | 2 | 2 | 3 | 4 | 3 | 4 | 2 |
|  | 0.5 (0.56) | 4 | 4 | 5 | 3 | 4 | 3 | 5 | 2 | 4 | 2 |
|  | 0.25 (0.28) | 3 | 4 | 3 | 2 | 2 | 3 | 3 | 2 | 4 | 2 |
|  | 0.25 (0.28) | 2 | 2 | 4 | 2 | 2 | 2 | 3 | 1 | 4 | 2 |
|  | 0.125 (0.14) | 2 | 1 | 3 | 2 | 2 | 2 | 2 | 1 | 3 | 2 |
|  | 0.0625 (0.07) | 1 | 2 | 2 | 1 | 1 | 2 | 2 | 1 | 3 | 2 |
| 11 | 8.0 (8.96) | 5 | 4 | 4 | 3 | 4 | 4 | 3 | 3 | 4 | 1 |
|  | 4.0 (4.48) | 5 | 4 | 5 | 4 | 4 | 4 | 4 | 2 | 5 | 2 |
|  | 2.0 (2.24) | 5 | 4 | 5 | 4 | 4 | 4 | 4 | 2 | 5 | 2 |
|  | 1.0 (1.12) | 4 | 3 | 5 | 3 | 4 | 4 | 3 | 2 | 4 | 2 |
|  | 1.0 (1.12) | 4 | 3 | 4 | 2 | 2 | 3 | 4 | 1 | 4 | 1 |
|  | 0.5 (0.56) | 4 | 2 | 4 | 2 | 2 | 3 | 3 | 1 | 3 | 1 |
|  | 0.25 (0.28) | 4 | 3 | 3 | 3 | 2 | 3 | 3 | 2 | 3 | 2 |
| 42 | 8.0 (8.96) | 3 | 3 | 5 | 2 | 1 | 4 | 5 | 1 | 5 | 1 |
|  | 4.0 (4.48) | 4 | 4 | 5 | 3 | 4 | 3 | 5 | 1 | 5 | 1 |
|  | 2.0 (2.24) | 4 | 4 | 5 | 3 | 3 | 3 | 5 | 1 | 5 | 1 |
|  | 1.0 (1.12) | 4 | 3 | 5 | 4 | 2 | 4 | 4 | 2 | 5 | 1 |
|  | 1.0 (1.12) | 3 | 3 | 4 | 2 | 2 | 1 | 5 | 2 | 4 | 1 |
|  | 0.5 (0.56) | 2 | 3 | 4 | 2 | 3 | 2 | 5 | 1 |  | 1 |
|  | 0.25 (0.28) | 2 | 4 | 4 | 2 | 2 | 1 | 2 | 1 | 4 | 1 |
|  | 0.25 (0.28) | 2 | 2 | 4 | 2 | 2 | 2 | 2 | 1 | 4 | 1 |
|  | 0.125 (0.14) | 2 | 2 | 2 | 2 | 2 | 2 | 3 | 1 | 2 | 1 |
|  | 0.0625 (0.07) | 1 | 2 | 3 | 1 | 2 | 1 | 2 | 1 | 3 | 1 |
| 44 | 8.0 (8.96) | 4 | 5 | 5 | 4 | 3 | 3 | 5 | 3 | 5 | 2 |
|  | 4.0 (4.48) | 5 | 5 | 5 | 4 | 5 | 5 | 5 | 4 | 5 | 3 |
|  | 2.0 (2.24) | 5 | 4 | 5 | 4 | 5 | 4 | 5 | 4 | 5 | 2 |
|  | 1.0 (1.12) | 5 | 4 | 5 | 4 | 4 | 4 | 5 | 3 | 5 | 2 |
|  | 1.0 (1.12) | 5 | 5 | 5 | 4 | 5 | 4 | 5 | 4 | 5 | 3 |
|  | 0.5 (0.56) | 4 | 4 | 5 | 3 | 3 | 2 | 5 | 3 | 4 | 2 |
| 44 | 0.25 (0.28) | 3 | 3 | 4 | 3 | 2 | 3 | 3 | 2 | 4 | 2 |
|  | 0.25 (0.28) | 5 | 4 | 3 | 4 | 5 | 3 | 5 | 2 | 4 | 3 |
|  | 0.125 (0.14) | 4 | 3 | 4 | 3 | 4 | 3 | 3 | 2 | 4 | 2 |
|  | 0.062 (0.07) | 4 | 2 | 4 | 3 | 3 | 2 | 3 | 2 | 4 | 2 |
|  | 0.062 (0.07) | 1 | 1 | 2 | 1 | 1 | 1 | 1 | 1 | 2 | 1 |
|  | 0.062 (0.07) | 3 | 2 | 3 | 3 | 3 | 3 | 3 | 2 | 3 | 1 |
| 93 | 8.0 (8.96) | 5 | 3 | 5 | 4 | 4 | 2 | 3 | 2 | 4 | 2 |
|  | 4.0 (4.48) | 5 | 3 | 3 | 4 | 5 | 4 | 4 | 4 | 4 | 1 |
|  | 2.0 (2.24) | 5 | 3 | 3 | 4 | 5 | 4 | 4 | 3 | 5 | 1 |
|  | 1.0 (1.12) | 5 | 3 | 3 | 5 | 4 | 3 | 4 | 3 | 4 | 1 |
|  | 1.0 (1.12) | 4 | 3 | 5 | 3 | 3 | 2 | 4 | 2 | 4 | 2 |
|  | 0.5 (0.56) | 4 | 2 | 5 | 4 | 3 | 1 | 4 | 2 | 4 | 2 |

TABLE III-continued

Postemergence

| Example No. of Compound Tested | Rate of Appln. lbs/acre (kg/ha) | Tomato | Large Crab-grass | Pig-weed | Fox-tail | Velvet-leaf | Morning-glory | Zinnia | Barn-yard Grass | Mus-tard | Wild Oats |
|---|---|---|---|---|---|---|---|---|---|---|---|
| | 0.25 (0.28) | 4 | 3 | 3 | 4 | 2 | 2 | 4 | 2 | 4 | 2 |
| | 0.25 (0.28) | 5 | 3 | 4 | 4 | 3 | 2 | 5 | 2 | 4 | 2 |
| | 0.125 (0.14) | 4 | 2 | 4 | 4 | 2 | 2 | 5 | 1 | 3 | 2 |
| | 0.062 (0.07) | 2 | 2 | 4 | 3 | 2 | 1 | 3 | 1 | 3 | 1 |
| 58 | 8.0 (8.96) | 2 | 3 | 5 | 2 | 2 | 2 | 4 | 1 | 3 | 1 |
| | 4.0 (4.48) | 2 | 3 | 3 | 1 | 1 | 1 | 3 | 1 | 3 | 1 |
| | 2.0 (2.24) | 2 | 2 | 2 | 1 | 1 | 1 | 3 | 1 | 3 | 1 |
| | 1.0 (1.12) | 2 | 1 | 2 | 1 | 1 | 1 | 2 | 1 | 2 | 1 |
| 43 | 8.0 (8.96) | 5 | 4 | 5 | 2 | 4 | 4 | 2 | 2 | 5 | 1 |
| | 4.0 (4.48) | 5 | 4 | 5 | 4 | 4 | 4 | 5 | 3 | 5 | 2 |
| | 2.0 (2.24) | 4 | 3 | 5 | 3 | 3 | 3 | 3 | 1 | 5 | 2 |
| | 1.0 (1.12) | 4 | 2 | 5 | 2 | 3 | 3 | 3 | 1 | 5 | 1 |
| | 1.0 (1.12) | 4 | 3 | 4 | 2 | 3 | 4 | 3 | 2 | 5 | 2 |
| | 0.5 (0.56) | 4 | 4 | 4 | 2 | 4 | 2 | 3 | 2 | 4 | 2 |
| | 0.75 (0.28) | 3 | 3 | 5 | 2 | 2 | 3 | 2 | 2 | 4 | 3 |
| | 0.25 (0.28) | 3 | 2 | 2 | 2 | 2 | 3 | 3 | 2 | 4 | 3 |
| | 0.12 (0.14) | 2 | 2 | 3 | 2 | 4 | 3 | 3 | 2 | 3 | 2 |
| | 0.062 (0.07) | 1 | 2 | 3 | 2 | 2 | 2 | 3 | 2 | 3 | 2 |
| 68 | 8.0 (8.96) | 5 | 1 | 4 | 2 | 3 | 2 | 4 | 1 | 5 | 2 |
| | 4.0 (4.48) | 4 | 3 | 4 | 3 | 3 | 2 | 5 | 1 | 5 | 1 |
| | 2.0 (2.24) | 4 | 3 | 4 | 3 | 2 | 2 | 4 | 1 | 5 | 1 |
| | 1.0 (1.12) | 2 | 3 | 4 | 1 | 2 | 2 | 2 | 1 | 4 | 1 |
| | 1.0 (1.12) | 1 | 2 | 4 | 2 | 2 | 2 | 3 | 1 | 4 | 1 |
| | 0.5 (0.56) | 1 | 2 | 2 | 1 | 1 | 1 | 2 | 1 | 3 | 1 |
| | 0.25 (0.28) | 1 | 2 | 2 | 1 | 1 | 1 | 1 | 1 | 3 | 1 |
| 28 | 8.0 (8.96) | 4 | 1 | 4 | 4 | 2 | 2 | 4 | 1 | 4 | 1 |
| | 4.0 (4.48) | 3 | 1 | 5 | 2 | 2 | 1 | 3 | 1 | 4 | 1 |
| | 2.0 (2.24) | 3 | 1 | 4 | 2 | 2 | 1 | 3 | 1 | 3 | 1 |
| | 1.0 (1.12) | 2 | 1 | 4 | 1 | 2 | 1 | 2 | 1 | 3 | 1 |
| 19 | 8.0 (8.96) | 3 | 4 | 5 | 2 | 3 | 3 | 4 | 2 | 4 | 2 |
| | 4.0 (4.48) | 4 | 4 | 5 | 2 | 4 | 3 | 4 | 1 | 5 | 1 |
| | 2.0 (2.28) | 4 | 3 | 5 | 2 | 3 | 3 | 3 | 1 | 4 | 1 |
| | 1.0 (1.12) | 2 | 2 | 2 | 2 | 2 | 2 | 3 | 1 | 3 | 1 |
| 67 | 8.0 (8.96) | 5 | 5 | 5 | 5 | 5 | 5 | 5 | 2 | 5 | 2 |
| | 4.0 (4.48) | 5 | 4 | 5 | 4 | 3 | 4 | 4 | 2 | 5 | 1 |
| | 2.0 (2.24) | 3 | 3 | 5 | 2 | 2 | 4 | 5 | 1 | 4 | 1 |
| | 1.0 (1.12) | 3 | 4 | 5 | 2 | 2 | 2 | 4 | 1 | 4 | 1 |
| | 1.0 (1.12) | 4 | 3 | 4 | 2 | 4 | 4 | 3 | 2 | 3 | 2 |
| | 0.5 (0.56) | 3 | 3 | 4 | 3 | 3 | 4 | 3 | 2 | 4 | 1 |
| | 0.25 (0.28) | 3 | 2 | 3 | 2 | 3 | 3 | 2 | 1 | 3 | 1 |
| 73 | 8.0 (8.96) | 4 | 4 | 5 | 4 | 5 | 5 | 5 | 3 | 5 | 1 |
| | 4.0 (4.48) | 4 | 5 | 5 | 4 | 5 | 3 | 5 | 2 | 4 | 1 |
| | 2.0 (2.24) | 2 | 5 | 5 | 2 | 4 | 2 | 3 | 2 | 5 | 1 |
| | 1.0 (1.12) | 2 | 4 | 5 | 2 | 4 | 2 | 3 | 2 | 4 | 1 |
| | 1.0 (1.12) | 4 | 3 | 3 | 3 | 4 | 5 | 5 | 2 | 4 | 2 |
| | 0.5 (0.56) | 3 | 3 | 3 | 2 | 3 | 3 | 4 | 2 | 3 | 2 |
| | 0.25 (0.28) | 2 | 2 | 2 | 2 | 3 | 2 | 2 | 2 | 3 | 2 |
| 69 | 8.0 (8.96) | 1 | 1 | 3 | 3 | 1 | 1 | 2 | 1 | 4 | 1 |
| 77 | 8.0 (8.96) | 4 | 4 | 5 | 4 | 4 | 4 | 5 | 3 | 5 | 3 |
| | 4.0 (4.48) | 4 | 4 | 4 | 3 | 5 | 2 | 4 | 3 | 4 | 2 |
| | 2.0 (2.24) | 2 | 4 | 5 | 2 | 2 | 3 | 2 | 1 | 4 | 2 |
| | 1.0 (1.12) | 2 | 3 | 4 | 2 | 2 | 2 | 2 | 1 | 3 | 2 |
| 9 | 8.0 (8.96) | 1 | 2 | 2 | 2 | 1 | 2 | 1 | 1 | 2 | 1 |
| 16 | 8.0 (8.96) | 5 | 5 | 4 | 5 | 5 | 3 | 5 | 2 | 5 | 2 |
| | 4.0 (4.48) | 2 | 2 | 3 | 1 | 1 | 1 | 1 | 1 | 2 | 1 |
| | 2.0 (2.24) | 1 | 1 | 1 | 1 | 1 | 1 | 1 | 1 | 2 | 1 |
| | 1.0 (1.12) | 1 | 1 | 2 | 1 | 1 | 1 | 1 | 1 | 2 | 1 |
| 29 | 8.0 (8.96) | 2 | 2 | 2 | 3 | 2 | 2 | 3 | 1 | 4 | 1 |
| 87 | 8.0 (8.96) | 2 | 2 | 2 | 2 | 2 | 2 | 2 | 1 | 4 | 1 |
| 57 | 8.0 (8.96) | 4 | 4 | 5 | 4 | 4 | 4 | 4 | 2 | 4 | 1 |
| | 4.0 (4.48) | 3 | 2 | 5 | 3 | 3 | 3 | 4 | 1 | 5 | 1 |
| | 2.0 (2.24) | 2 | 3 | 5 | 4 | 2 | 3 | 5 | 1 | 4 | 1 |
| | 1.0 (1.12) | 2 | 3 | 4 | 2 | 2 | 3 | 5 | 1 | 4 | 1 |
| | 1.0 (1.12) | 2 | 1 | 4 | 1 | 1 | 3 | 3 | 1 | 3 | 1 |
| | 0.5 (0.56) | 2 | 1 | 4 | 1 | 1 | 3 | 1 | 1 | 2 | 1 |
| | 0.25 (0.28) | 1 | 1 | 3 | 1 | 1 | 1 | 1 | 1 | 2 | 1 |
| 27 | 8.0 (8.96) | 4 | 5 | 4 | 4 | 4 | 4 | 5 | 3 | 4 | 2 |
| | 4.0 (4.48) | 4 | 3 | 4 | 2 | 4 | 2 | 5 | 1 | 4 | 2 |
| | 2.0 (2.24) | 4 | 2 | 4 | 2 | 2 | 2 | 5 | 1 | 3 | 1 |
| | 1.0 (1.12) | 4 | 2 | 3 | 2 | 2 | 2 | 5 | 1 | 3 | 2 |
| | 1.0 (1.12) | 4 | 3 | 3 | 3 | 4 | 5 | 5 | 1 | 4 | 1 |
| | 0.5 (0.56) | 4 | 3 | 2 | 3 | 4 | 3 | 4 | 1 | 4 | 1 |
| | 0.25 (0.28) | 3 | 2 | 3 | 2 | 4 | 3 | 3 | 1 | 5 | 1 |
| | 0.25 (0.28) | 3 | 4 | 4 | 2 | 4 | 4 | 4 | 1 | 4 | 1 |
| | 0.125 (0.14) | 3 | 3 | 2 | 3 | 3 | 3 | 3 | 1 | 3 | 1 |
| | 0.0625 (0.07) | 2 | 2 | 2 | 2 | 2 | 2 | 2 | 1 | 3 | 1 |
| 89 | 8.0 (8.96) | 2 | 3 | 5 | 2 | 2 | 3 | 4 | 3 | 4 | 2 |

TABLE III-continued

Postemergence

| Example No. of Compound Tested | Rate of Appln. lbs/acre (kg/ha) | Tomato | Large Crab-grass | Pig-weed | Fox-tail | Velvet-leaf | Morning-glory | Zinnia | Barn-yard Grass | Mus-tard | Wild Oats |
|---|---|---|---|---|---|---|---|---|---|---|---|
| | 4.0 (4.48) | 3 | 3 | 4 | 2 | 2 | 2 | 5 | 2 | 4 | 2 |
| | 2.0 (2.24) | 2 | 3 | 2 | 2 | 2 | 2 | 3 | 1 | 4 | 1 |
| | 1.0 (1.12) | 2 | 3 | 2 | 2 | 2 | 2 | 3 | 1 | 4 | 1 |
| 90 | 8.0 (8.96) | 2 | 3 | 4 | 5 | 1 | 2 | 2 | 1 | 3 | 2 |
| | 4.0 (4.48) | 2 | 3 | 2 | 2 | 2 | 2 | 1 | 1 | 3 | 1 |
| | 2.0 (2.24) | 2 | 3 | 2 | 2 | 1 | 2 | 1 | 1 | 3 | 2 |
| | 1.0 (1.12) | 1 | 2 | 2 | 2 | 1 | 1 | 1 | 1 | 3 | 1 |
| 74 | 8.0 (8.96) | 4 | 4 | 5 | 2 | 4 | 4 | 5 | 2 | 4 | 3 |
| | 4.0 (4.48) | 4 | 4 | 5 | 3 | 5 | 4 | 4 | 2 | 4 | 2 |
| | 2.0 (2.24) | 4 | 4 | 4 | 2 | 4 | 3 | 4 | 2 | 4 | 1 |
| | 1.0 (1.12) | 4 | 4 | 4 | 3 | 4 | 3 | 3 | 2 | 4 | 3 |
| | 1.0 (1.12) | 3 | 3 | 3 | 2 | 4 | 5 | 4 | 1 | 3 | 2 |
| | 0.5 (0.56) | 2 | 3 | | 2 | 3 | 3 | 3 | 1 | 3 | 2 |
| | 0.25 (0.28) | 2 | 2 | 3 | 2 | 3 | 2 | 2 | 1 | 2 | 1 |
| 18 | 8.0 (8.96) | 2 | 3 | 4 | 3 | 2 | 2 | 2 | 2 | 3 | 1 |
| 50 | 8.0 (8.96) | 5 | 2 | 4 | 3 | 4 | 4 | 4 | 2 | 4 | 2 |
| | 4.0 (4.48) | 4 | 2 | 4 | 2 | 3 | 3 | 5 | 1 | 4 | 2 |
| | 2.0 (2.24) | 4 | 3 | 4 | 3 | 3 | 4 | 4 | 1 | 4 | 2 |
| | 1.0 (1.12) | 3 | 3 | 3 | 2 | 4 | 4 | 3 | 1 | 4 | 1 |
| | 1.0 (1.12) | 4 | 3 | 4 | 4 | 5 | 4 | 5 | 2 | | 3 |
| | 0.5 (0.56) | 4 | 3 | 4 | 4 | 5 | 3 | 5 | 2 | | 2 |
| | 0.25 (0.28) | 2 | 2 | 4 | 3 | 4 | 3 | 5 | 2 | 3 | 2 |
| 79 | 8.0 (8.96) | 5 | 2 | 5 | 3 | 3 | 4 | 4 | 4 | 4 | 2 |
| | 4.0 (4.48) | 4 | 3 | 3 | 3 | 2 | 3 | 3 | 3 | 4 | 1 |
| | 2.0 (2.24) | 2 | 3 | 4 | 3 | 2 | 2 | 4 | 2 | 4 | 1 |
| | 1.0 (1.12) | 2 | 2 | 3 | 2 | 3 | 3 | 3 | 1 | 3 | 2 |
| 45 | 8.0 (8.96) | 4 | 4 | 5 | 3 | 3 | 3 | 5 | 3 | 4 | 2 |
| | 4.0 (4.48) | 4 | 3 | 4 | 3 | 4 | 3 | 5 | 2 | 4 | 2 |
| | 2.0 (2.24) | 4 | 3 | 4 | 2 | 2 | 2 | 4 | 2 | 4 | 1 |
| | 1.0 (1.12) | 2 | 3 | 4 | 3 | 2 | 2 | 4 | 1 | 3 | 2 |
| | 1.0 (1.12) | 3 | 2 | 4 | 3 | 4 | 2 | 3 | 2 | 4 | 1 |
| | 0.5 (0.56) | 2 | 3 | 3 | 2 | 3 | 2 | 4 | 1 | 4 | 1 |
| | 0.25 (0.28) | 2 | 2 | 3 | 2 | 2 | 2 | 3 | 2 | 3 | 1 |
| 47 | 8.0 (8.96) | 1 | 1 | 4 | 1 | 2 | 2 | 3 | 1 | 3 | 1 |
| 48 | 8.0 (8.96) | 1 | 2 | 3 | 1 | 2 | 2 | 4 | 1 | 4 | 1 |
| | 4.0 (4.48) | 3 | 1 | 3 | 1 | 2 | 2 | 3 | 1 | 3 | 1 |
| | 2.0 (2.24) | 2 | 1 | 2 | 1 | 2 | 2 | 3 | 1 | 2 | 1 |
| | 1.0 (1.12) | 1 | 1 | 1 | 1 | 1 | 1 | 2 | 1 | 2 | 1 |
| 17 | 8.0 (8.96) | 5 | 4 | 5 | 4 | 4 | 3 | 5 | 4 | 5 | 1 |
| | 4.0 (4.48) | 5 | 4 | 4 | 4 | 5 | 4 | 4 | 2 | 4 | 2 |
| | 2.0 (2.24) | 5 | 4 | 4 | 4 | 4 | 4 | 4 | 3 | 5 | 2 |
| | 1.0 (1.12) | 4 | 3 | 3 | 3 | 3 | 2 | 4 | 1 | 4 | 1 |
| | 1.0 (1.12) | 4 | 3 | 4 | 3 | 3 | 3 | 5 | 2 | 5 | 2 |
| | 0.5 (0.56) | 4 | 3 | 4 | 3 | 3 | 3 | 4 | 2 | 4 | 1 |
| | 0.25 (0.28) | 4 | 2 | 4 | 3 | 4 | 2 | 5 | 1 | 4 | 1 |
| | 0.25 (0.28) | 4 | 3 | 4 | 4 | 3 | 3 | 5 | 2 | 4 | 1 |
| | 0.125 (0.14) | 4 | 3 | 3 | 4 | 3 | 2 | 4 | 1 | 3 | 1 |
| | 0.0625 (0.07) | 3 | 3 | | 2 | 3 | 2 | 3 | 1 | 3 | 1 |
| 40 | 8.0 (8.96) | 4 | 2 | 4 | 2 | 2 | 3 | 5 | 1 | 4 | 1 |
| | 4.0 (4.48) | 3 | 1 | 3 | 2 | 2 | 3 | 3 | 1 | 4 | 1 |
| | 2.0 (2.24) | 3 | 1 | 3 | 1 | 2 | 2 | 3 | 1 | 3 | 1 |
| | 1.0 (1.12) | 3 | 1 | 2 | 1 | 2 | 2 | 2 | 1 | 3 | 1 |
| 2 | 8.0 (8.96) | 1 | 1 | 2 | 1 | 1 | 1 | 1 | 1 | 2 | 1 |
| 10 | 4.0 (4.48) | 3 | 2 | 5 | 2 | 2 | 2 | 5 | 1 | 5 | 1 |
| | 2.0 (2.24) | 3 | 3 | 5 | 2 | 2 | 3 | 4 | 1 | 4 | 1 |
| | 1.0 (1.12) | 1 | 5 | 2 | 2 | 2 | 1 | 1 | 4 | 2 | 4 |
| | 1.0 (1.12) | 3 | 2 | 3 | 2 | 2 | 2 | 3 | 1 | 4 | 1 |
| | 0.5 (0.56) | 2 | 1 | 3 | 2 | 2 | 2 | 3 | 1 | 4 | 1 |
| | 0.25 (0.28) | 2 | 1 | 3 | 2 | 1 | 2 | 2 | 1 | 4 | 1 |
| 64 | 8.0 (8.96) | 4 | 4 | 5 | 3 | 3 | 2 | 5 | 2 | 4 | 2 |
| | 4.0 (4.48) | 4 | 4 | 4 | 2 | 5 | 3 | 5 | 3 | 5 | 2 |
| | 2.0 (2.24) | 2 | 2 | 4 | 2 | 3 | 2 | 5 | 1 | 5 | 2 |
| | 1.0 (1.12) | 2 | 3 | 3 | 2 | 2 | 2 | 5 | 1 | 4 | 2 |
| | 1.0 (1.12) | 2 | 3 | 5 | 2 | 2 | 2 | 4 | 2 | 4 | 2 |
| | 0.5 (0.56) | 2 | 2 | 4 | 2 | 2 | 2 | 3 | 2 | 4 | 2 |
| | 0.25 (0.28) | 2 | 2 | 4 | 2 | 2 | 2 | 3 | 2 | 3 | 1 |
| 71 | 8.0 (8.96) | 5 | 4 | 5 | 4 | 4 | 4 | 4 | 3 | 4 | 2 |
| | 4.0 (4.48) | 5 | 4 | 5 | 2 | 4 | 5 | 5 | 3 | 5 | 2 |
| | 2.0 (2.24) | 5 | 3 | 4 | 2 | 4 | 4 | 5 | 2 | 5 | 2 |
| | 1.0 (1.12) | 4 | 2 | 4 | 2 | 4 | 4 | 4 | 2 | 4 | 2 |
| | 1.0 (1.12) | 4 | 3 | 3 | 2 | 3 | 4 | 3 | 1 | 4 | 2 |
| | 0.5 (0.56) | 3 | 3 | 3 | 2 | 3 | 2 | 2 | 1 | 3 | 2 |
| | 0.25 (0.28) | 2 | 2 | 2 | 2 | 2 | 2 | 2 | 1 | 2 | 1 |
| 77 | 8.0 (8.96) | 1 | 2 | 4 | 2 | 1 | 2 | 3 | 1 | 3 | 1 |
| 22 | 8.0 (8.96) | 2 | 2 | 3 | 3 | 3 | 3 | 2 | 1 | 3 | 1 |
| 35 | 8.0 (8.96) | 1 | 3 | 4 | 3 | 3 | 2 | 1 | 1 | 3 | 1 |
| 49 | 8.0 (8.96) | 4 | 2 | 5 | 4 | 3 | 3 | 5 | 3 | 4 | 1 |

TABLE III-continued

Postemergence

| Example No. of Compound Tested | Rate of Appln. lbs/acre (kg/ha) | Tomato | Large Crab-grass | Pig-weed | Fox-tail | Velvet-leaf | Morning-glory | Zinnia | Barn-yard Grass | Mus-tard | Wild Oats |
|---|---|---|---|---|---|---|---|---|---|---|---|
| | 4.0 (4.48) | 4 | 3 | 5 | 4 | 4 | 2 | 5 | 2 | 4 | 2 |
| | 2.0 (2.24) | 4 | 2 | 5 | 4 | 3 | 2 | 5 | 3 | 4 | 2 |
| | 1.0 (1.12) | 3 | 1 | 5 | 3 | 3 | 2 | 4 | 2 | 3 | 1 |
| | 1.0 (1.12) | 3 | 1 | 5 | 3 | 1 | 1 | 3 | 2 | 5 | 1 |
| | 0.5 (0.56) | 3 | 1 | 4 | 1 | 2 | 1 | 2 | 2 | 2 | 1 |
| | 0.25 (0.28) | 1 | 1 | 3 | 2 | 1 | 1 | 2 | 2 | 3 | 1 |
| 15 | 8.0 (8.96) | 4 | 4 | 3 | 4 | 3 | 3 | 4 | 4 | 4 | 2 |
| | 4.0 (4.48) | 2 | 3 | 4 | 4 | 5 | 4 | 5 | 3 | 4 | 3 |
| | 2.0 (2.24) | 3 | 3 | 4 | 4 | 3 | 2 | 5 | 2 | 4 | 2 |
| | 1.0 (1.12) | 2 | 3 | 4 | 2 | 2 | 2 | 2 | 3 | 3 | 1 |
| 66 | 8.0 (8.96) | 4 | 4 | 5 | 4 | 5 | 4 | 4 | 3 | 5 | 1 |
| | 4.0 (4.48) | 5 | 4 | 5 | 4 | 5 | 4 | 4 | 4 | 4 | 2 |
| | 2.0 (2.24) | 3 | 4 | 5 | 4 | 4 | 4 | 4 | 2 | 4 | 2 |
| | 1.0 (1.12) | 4 | 4 | 5 | 4 | 4 | 4 | 5 | 2 | 4 | 2 |
| | 1.0 (1.12) | 3 | 4 | 5 | 3 | 4 | 3 | 4 | 2 | 4 | 2 |
| | 1.0 (1.12) | 4 | 4 | 3 | 2 | 3 | 3 | 5 | 1 | 4 | 2 |
| | 0.5 (0.56) | 3 | 4 | 4 | 3 | 4 | 3 | 3 | 2 | 4 | 1 |
| | 0.5 (0.56) | 3 | 2 | 4 | 2 | 3 | 5 | 4 | 1 | 3 | 1 |
| | 0.25 (0.28) | 2 | 3 | 4 | 3 | 4 | 2 | 4 | 1 | 4 | 2 |
| | 0.25 (0.28) | 2 | 2 | 4 | 1 | 2 | 2 | 3 | 1 | 3 | 2 |
| 26 | 8.0 (8.96) | 1 | 3 | 4 | 3 | 3 | 3 | 4 | 1 | 3 | 1 |
| | 4.0 (4.48) | 2 | 3 | 4 | 3 | 3 | 2 | 3 | 1 | 3 | 1 |
| | 2.0 (2.24) | 2 | 2 | 4 | 3 | 3 | 2 | 3 | 1 | 3 | 1 |
| | 1.0 (1.12) | 1 | 2 | 3 | 2 | 1 | 1 | 2 | 1 | 3 | 1 |
| 81 | 8.0 (8.96) | 5 | 5 | 5 | 3 | 5 | 5 | 5 | 4 | 5 | 4 |
| | 4.0 (4.48) | 5 | 5 | 5 | 5 | 5 | 5 | 5 | 4 | 5 | 3 |
| | 2.0 (2.24) | 5 | 5 | 5 | 4 | 5 | 4 | 5 | 3 | 4 | 4 |
| | 1.0 (1.12) | 4 | 4 | 5 | 4 | 4 | 4 | 5 | 3 | 3 | 2 |
| | 1.0 (1.12) | 4 | 3 | 5 | 3 | 4 | 5 | 5 | 3 | 4 | 2 |
| | 0.5 (0.56) | 3 | 4 | 5 | 3 | 4 | 3 | 3 | 2 | 3 | 2 |
| | 0.25 (0.28) | 2 | 3 | 3 | 2 | 4 | 3 | 3 | 1 | 3 | 2 |
| 55 | 8.0 (8.96) | 2 | 3 | 5 | 2 | 3 | 3 | 3 | 1 | 4 | 1 |
| | 4.0 (4.48) | 3 | 3 | 5 | 3 | 3 | 4 | 4 | 2 | 4 | 2 |
| | 2.0 (2.24) | 3 | 2 | 5 | 3 | 2 | 3 | 2 | 2 | 4 | 1 |
| | 1.0 (1.12) | 2 | 2 | 4 | 2 | 1 | 2 | 3 | 1 | 3 | 1 |
| 13 | 8.0 (8.96) | 3 | 4 | 4 | 2 | 4 | 3 | 4 | 2 | 3 | 2 |
| | 4.0 (4.48) | 4 | 4 | 5 | 4 | 5 | 4 | 5 | 3 | 4 | 3 |
| | 2.0 (2.24) | 3 | 4 | 5 | 4 | 4 | 4 | 4 | 2 | 4 | 2 |
| | 1.0 (1.12) | 3 | 3 | 4 | 4 | 4 | 3 | 4 | 1 | 5 | 1 |
| | 1.0 (1.12) | 3 | 3 | 4 | 3 | 3 | 3 | 4 | 1 | 5 | 1 |
| | 0.5 (0.56) | 2 | 3 | 4 | 3 | 3 | 2 | 3 | 1 | 4 | 1 |
| | 0.25 (0.28) | 1 | 1 | 2 | 3 | 2 | 2 | 2 | 1 | 2 | 1 |
| 1 | 8.0 (8.96) | 3 | 5 | 4 | 3 | 4 | 4 | 5 | 3 | 4 | 3 |
| | 4.0 (4.48) | 4 | 4 | 5 | 4 | 4 | 4 | 5 | 4 | 4 | 3 |
| | 2.0 (2.24) | 5 | 4 | 5 | 4 | 4 | 4 | 5 | 3 | 4 | 3 |
| | 1.0 (1.12) | 4 | 3 | 4 | 3 | 4 | 4 | 4 | 2 | 4 | 1 |
| | 1.0 (1.12) | 4 | 4 | 5 | 3 | 4 | 4 | 4 | 2 | 4 | 3 |
| | 0.5 (0.56) | 4 | 4 | 5 | 3 | 4 | 4 | 4 | 1 | 4 | 2 |
| | 0.25 (0.28) | 3 | 3 | 4 | 3 | 4 | 3 | 4 | 2 | 4 | 1 |
| | 0.25 (0.28) | 2 | 3 | 5 | 3 | 4 | 2 | 3 | 2 | 4 | 1 |
| | 0.125 (0.14) | 2 | 4 | 5 | 2 | 3 | 3 | 5 | 1 | 4 | 2 |
| | 0.0625 (0.07) | 2 | 4 | 3 | 2 | 3 | 2 | 2 | 1 | 3 | 1 |
| 7 | 8.0 (8.96) | 1 | 3 | 4 | 1 | 1 | 2 | 1 | 1 | 3 | 1 |
| 87 | 8.0 (8.96) | 3 | 4 | 5 | 4 | 4 | 5 | 5 | 5 | 4 | 2 |
| | 4.0 (4.48) | 5 | 5 | 5 | 4 | 5 | 4 | 5 | 4 | 5 | 2 |
| | 2.0 (2.24) | 5 | 4 | 5 | 4 | 5 | 4 | 5 | 4 | 4 | 1 |
| | 1.0 (1.12) | 3 | 4 | 5 | 4 | 5 | 4 | 5 | 3 | 4 | 1 |
| | 1.0 (1.12) | 2 | 2 | 5 | 4 | 4 | 4 | 4 | 3 | 3 | 1 |
| | 0.5 (0.56) | 2 | 3 | 5 | 3 | 4 | 4 | 5 | 2 | 4 | 2 |
| | 0.25 (0.28) | 2 | 1 | 4 | 3 | 4 | 3 | 4 | 2 | 3 | 1 |
| | 0.25 (0.28) | 2 | 4 | 3 | 2 | 4 | 2 | 5 | 2 | 4 | 1 |
| | 0.125 (0.14) | 1 | 2 | 2 | 2 | 3 | 1 | 2 | 2 | 1 | 3 |
| | 0.0625 (0.07) | 1 | 2 | 2 | 2 | 2 | 1 | 2 | 1 | 2 | 1 |
| 34 | 8.0 (8.96) | 4 | 4 | 5 | 2 | 4 | 4 | 4 | 2 | 5 | 2 |
| | 4.0 (4.48) | 2 | 3 | 3 | 2 | 3 | 2 | 2 | 2 | 3 | 1 |
| | 2.0 (2.24) | 2 | 3 | 4 | 3 | 2 | 3 | 2 | 1 | 4 | 1 |
| | 1.0 (1.12) | 2 | 2 | 3 | 2 | 3 | 3 | 2 | 1 | 2 | 1 |
| 21 | 8.0 (8.96) | 1 | 1 | 4 | 2 | 3 | 2 | 2 | 1 | 3 | 1 |
| 76 | 8.0 (8.96) | 4 | 5 | 5 | 4 | 5 | 5 | 5 | 4 | 5 | 5 |
| | 4.0 (4.48) | 5 | 5 | 5 | 5 | 5 | 5 | 5 | 4 | 5 | 4 |
| | 2.0 (2.24) | 5 | | 5 | 3 | 4 | 4 | 5 | 4 | 5 | 2 |
| | 1.0 (1.12) | 3 | 3 | 5 | 3 | 4 | 3 | 5 | 2 | 4 | 3 |
| | 1.0 (1.12) | 4 | 4 | 5 | 4 | 4 | 4 | 5 | 4 | 4 | 3 |
| | 0.5 (0.56) | 4 | 4 | 5 | 3 | 4 | 3 | 4 | 2 | 4 | 2 |
| | 0.25 (0.28) | 2 | 3 | 5 | 4 | 3 | 3 | 3 | 2 | 4 | 2 |
| 76 | 0.25 (0.28) | 2 | 4 | 4 | 4 | 4 | 3 | 4 | 2 | 4 | 2 |
| | 0.125 (0.14) | 2 | 3 | 3 | 3 | 3 | 2 | 3 | 1 | 4 | 2 |

TABLE III-continued

Postemergence

| Example No. of Compound Tested | Rate of Appln. lbs/acre (kg/ha) | Tomato | Large Crab-grass | Pig-weed | Fox-tail | Velvet-leaf | Morning-glory | Zinnia | Barn-yard Grass | Mus-tard | Wild Oats |
|---|---|---|---|---|---|---|---|---|---|---|---|
| | 0.0625 (0.07) | 1 | 2 | 3 | 2 | 2 | 2 | 2 | 1 | 3 | 1 |
| 12 | 8.0 (8.96) | 5 | 4 | 5 | 4 | 5 | 5 | 5 | 4 | 5 | 4 |
| | 4.0 (4.48) | 5 | 5 | 5 | 5 | 5 | 5 | 5 | 4 | 5 | 4 |
| | 2.0 (2.24) | 5 | 4 | 5 | 5 | 5 | 4 | 5 | 4 | 5 | 4 |
| | 1.0 (1.12) | 4 | 5 | 5 | 4 | 5 | 4 | 5 | 4 | 5 | 3 |
| | 1.0 (1.12) | 5 | 4 | 5 | 4 | 4 | 4 | 5 | 4 | 4 | 2 |
| | 0.5 (0.56) | 4 | 4 | 4 | 4 | 4 | 4 | 5 | 3 | 4 | 2 |
| | 0.25 (0.28) | 4 | 4 | 5 | 3 | 4 | 4 | 5 | 3 | 4 | 3 |
| | 0.25 (0.28) | 4 | 4 | 4 | 3 | 5 | 4 | 4 | 2 | 4 | 2 |
| | 0.125 (0.14) | 4 | 3 | 4 | 3 | 4 | 3 | 4 | 2 | 4 | 2 |
| | 0.0625 (0.07) | 3 | 3 | 3 | 3 | 3 | 2 | 3 | 2 | 3 | 1 |
| 91 | 8.0 (8.96) | 1 | 4 | 5 | 3 | 3 | 1 | 4 | 4 | 4 | 1 |
| | 4.0 (4.48) | 2 | 4 | — | 4 | 5 | 1 | 5 | 4 | 3 | 1 |
| | 2.0 (2.24) | 1 | 4 | — | 4 | 5 | 1 | 5 | 4 | 3 | 2 |
| | 1.0 (1.12) | 1 | 3 | — | 3 | 4 | 1 | 5 | 2 | 2 | 2 |
| | 1.0 (1.12) | 1 | 3 | 5 | 3 | 4 | 1 | 4 | 2 | 3 | 1 |
| | 0.5 (0.56) | 1 | 3 | 5 | 3 | 4 | 1 | 4 | 2 | 2 | 1 |
| | 0.25 (0.28) | 1 | 3 | 5 | 3 | 4 | 1 | 4 | 1 | 2 | 1 |
| | 0.25 (0.28) | 2 | 3 | 4 | 2 | 3 | 2 | 3 | 2 | 3 | 2 |
| | 0.125 (0.14) | 1 | 3 | 3 | 2 | 2 | 2 | 3 | 1 | 2 | 2 |
| | 0.0625 (0.07) | 1 | 2 | 3 | 2 | 2 | 2 | 3 | 1 | 2 | 1 |
| 37 | 8.0 (8.96) | 1 | 2 | 3 | 2 | 2 | 1 | 2 | 2 | 2 | 1 |
| 88 | 8.0 (8.96) | 5 | 4 | 5 | 4 | 5 | 5 | | 4 | 5 | 4 |
| | 4.0 (4.48) | 5 | 5 | 5 | 4 | 5 | 5 | 5 | 4 | 5 | 4 |
| | 2.0 (2.24) | 3 | 4 | 5 | 4 | 5 | 4 | 4 | 3 | 4 | 4 |
| | 1.0 (1.12) | 2 | 3 | 5 | 2 | 4 | 3 | 3 | 2 | 3 | 3 |
| | 1.0 (1.12) | 4 | 4 | 5 | 3 | 4 | 3 | 4 | 2 | 4 | 3 |
| | 0.5 (0.56) | 2 | 3 | 5 | 4 | 3 | 3 | 3 | 2 | 4 | 2 |
| | 0.25 (0.28) | 2 | 3 | 4 | 2 | 3 | 2 | 2 | 1 | 3 | 2 |
| 25 | 8.0 (8.96) | 4 | 4 | 5 | 2 | 3 | 4 | 4 | 3 | 5 | 3 |
| | 4.0 (4.48) | 5 | 4 | 5 | 3 | 5 | 3 | 4 | 4 | 4 | 3 |
| | 2.0 (2.24) | 4 | 4 | 5 | 4 | 5 | 3 | 4 | 3 | 4 | 4 |
| | 1.0 (1.12) | 3 | 4 | 5 | 2 | 4 | 2 | 3 | 2 | 4 | 2 |
| | 1.0 (1.12) | 3 | 3 | 5 | 3 | 3 | 3 | 3 | 2 | 4 | 3 |
| | 0.5 (0.56) | 3 | 3 | 5 | 3 | 3 | 3 | 3 | 2 | 4 | 2 |
| | 0.25 (0.28) | 2 | 2 | 4 | 3 | 3 | 3 | 3 | 2 | 3 | 2 |
| 6 | 8.0 (8.96) | 4 | 3 | 5 | 3 | 3 | 5 | 5 | 3 | 4 | 2 |
| | 4.0 (4.48) | 5 | 4 | 5 | 4 | 4 | 5 | 5 | 4 | 4 | 2 |
| | 2.0 (2.24) | 5 | 4 | 5 | 4 | 5 | 4 | 5 | 4 | 3 | 3 |
| | 1.0 (1.12) | 3 | 3 | 5 | 3 | 4 | 5 | 5 | 2 | 3 | 2 |
| | 1.0 (1.12) | 4 | 3 | 5 | 3 | 3 | 3 | 4 | 1 | 4 | 1 |
| | 0.5 (0.56) | 4 | 3 | 4 | 3 | 4 | 3 | 5 | 1 | 4 | 1 |
| | 0.25 (0.28) | 3 | 1 | 4 | 3 | 3 | 3 | 3 | 2 | 3 | 1 |
| 3 | 8.0 (8.96) | 5 | 4 | 5 | 4 | 5 | 5 | 5 | 3 | 4 | 3 |
| | 4.0 (4.48) | 5 | 4 | 5 | 4 | 5 | 5 | 5 | 5 | 4 | 5 |
| | 2.0 (2.24) | 4 | 4 | 5 | 3 | 4 | 4 | 5 | 3 | 5 | 4 |
| | 1.0 (1.12) | 4 | 3 | 5 | 4 | 5 | 4 | 5 | 4 | 4 | 3 |
| | 1.0 (1.12) | 5 | 3 | 5 | 4 | 4 | 4 | 5 | 2 | 4 | 3 |
| | 0.5 (0.56) | 5 | 4 | 5 | 4 | 5 | 5 | 5 | 3 | 4 | 3 |
| | 0.25 (0.28) | 5 | 3 | 4 | 4 | 5 | 4 | 5 | 3 | 4 | 2 |
| | 0.25 (0.28) | 4 | 3 | 3 | 4 | 4 | 4 | 5 | 3 | 4 | 2 |
| | 0.125 (0.14) | 4 | 3 | 3 | 3 | 5 | 4 | 5 | 2 | 4 | 2 |
| | 0.0625 (0.07) | 4 | 1 | 2 | 3 | 3 | 3 | 5 | 2 | 3 | 2 |
| | 0.0625 (0.07) | 1 | 2 | 1 | 1 | 2 | 1 | 2 | 1 | 2 | 1 |
| | 0.0625 (0.07) | 1 | 2 | 3 | 2 | 2 | 2 | 4 | 1 | 2 | 1 |
| | 0.0625 (0.07) | 2 | 2 | 4 | 2 | 1 | 3 | 4 | 1 | 4 | 2 |
| 30 | 8.0 (8.96) | 1 | 1 | 3 | 1 | 1 | 2 | 2 | 1 | 4 | 1 |
| 31 | 8.0 (8.96) | 2 | 4 | 4 | 2 | 3 | 2 | 2 | 4 | 4 | 1 |
| | 4.0 (4.48) | 3 | 3 | 5 | 3 | 3 | 3 | 3 | 3 | 3 | 1 |
| | 2.0 (2.24) | 1 | 4 | 5 | 3 | 2 | 3 | 3 | 2 | 3 | 2 |
| | 1.0 (1.12) | 1 | 3 | 5 | 2 | 2 | 3 | 3 | 2 | 3 | 1 |
| | 1.0 (1.12) | 2 | 2 | 4 | 2 | 2 | 3 | 3 | 1 | 3 | 1 |
| | 0.5 (0.56) | 2 | 3 | 4 | 2 | 2 | 2 | 2 | 1 | 3 | 1 |
| | 0.25 (0.28) | 1 | 3 | 4 | 2 | 2 | 2 | 2 | 1 | 2 | 1 |
| 35 | 8.0 (8.96) | 2 | 4 | 4 | 3 | 5 | 2 | 4 | 4 | 4 | 3 |
| | 4.0 (4.48) | 3 | 3 | 5 | 4 | 3 | 2 | 3 | 4 | 4 | 2 |
| | 2.0 (2.24) | 2 | 4 | 4 | 3 | 3 | 2 | 4 | 3 | 4 | 1 |
| | 1.0 (1.12) | 1 | 2 | 4 | 3 | 2 | 1 | 3 | 3 | 4 | 1 |
| | 1.0 (1.12) | 3 | 4 | 5 | 5 | 4 | 3 | 5 | 4 | 4 | 3 |
| | 0.5 (0.56) | 3 | 4 | 5 | 4 | 4 | 3 | 5 | 2 | 4 | 2 |
| | 0.25 (0.28) | 2 | 2 | 4 | 3 | 3 | 2 | 3 | 2 | 2 | 1 |
| 5 | 8.0 (8.96) | 4 | 4 | 4 | 2 | 4 | 2 | 3 | 4 | 4 | 1 |
| | 4.0 (4.48) | 4 | 4 | 5 | 4 | 5 | 3 | 5 | 4 | 4 | 3 |
| | 2.0 (2.24) | 2 | 4 | 5 | 3 | 3 | 2 | 3 | 3 | 4 | 2 |
| | 1.0 (1.12) | 2 | 3 | 4 | 2 | 2 | 2 | 2 | 3 | 3 | 2 |
| 24 | 8.0 (8.96) | 5 | 5 | 5 | 5 | 5 | 5 | 5 | 4 | 5 | 4 |
| | 4.0 (4.48) | 4 | 4 | 5 | 5 | 5 | 4 | 5 | 4 | 4 | 2 |

TABLE III-continued

| | | Postemergence | | | | | | | | |
|---|---|---|---|---|---|---|---|---|---|---|
| Example No. of Compound Tested | Rate of Appln. lbs/acre (kg/ha) | Tomato | Large Crab-grass | Pig-weed | Fox-tail | Velvet-leaf | Morning-glory | Zinnia | Barn-yard Grass | Mus-tard | Wild Oats |
| | 2.0 (2.24) | 4 | 4 | 5 | 4 | 4 | 3 | 5 | 3 | 4 | 2 |
| | 1.0 (1.12) | 4 | 2 | 4 | 3 | 4 | 3 | 5 | 2 | 4 | 1 |
| | 1.0 (1.12) | 5 | 5 | 5 | 5 | 5 | 4 | 5 | 4 | 4 | 4 |
| | 0.5 (0.56) | 5 | 4 | 5 | 4 | 5 | 4 | 5 | 3 | 4 | 2 |
| | 0.25 (0.28) | 5 | 4 | 5 | 4 | 4 | 4 | 5 | 3 | 4 | 3 |
| | 0.25 (0.28) | 5 | 4 | 5 | 5 | 4 | 5 | 5 | 2 | 4 | 3 |
| | 0.125 (0.14) | 4 | 3 | 5 | 5 | 4 | 3 | 5 | 2 | 4 | 1 |
| | 0.0625 (0.07) | 2 | 3 | 4 | 4 | 3 | 3 | 3 | 1 | 3 | 1 |
| 8 | 4.0 (4.48) | 5 | 3 | 5 | 3 | 2 | 4 | 4 | 4 | 5 | 3 |
| | 2.0 (2.24) | 4 | 4 | 5 | 3 | 2 | 4 | 4 | 3 | 5 | 2 |
| | 1.0 (1.12) | 3 | 3 | 5 | 3 | 2 | 3 | 4 | 2 | 4 | 2 |
| | 1.0 (1.12) | 2 | 3 | 4 | 2 | 2 | 2 | 3 | 2 | 3 | 1 |
| | 0.5 (0.56) | 1 | 2 | 3 | 2 | 1 | 1 | 2 | 1 | 2 | 1 |
| | 0.25 (0.28) | 1 | 2 | 2 | 1 | 1 | 1 | 1 | 1 | 2 | 1 |
| 39 | 8.0 (8.96) | 4 | 5 | 5 | 3 | 4 | 4 | 4 | 5 | 5 | 3 |
| | 4.0 (4.48) | 4 | 3 | 5 | 2 | 4 | 4 | 5 | 3 | 4 | 2 |
| | 2.0 (2.24) | 4 | 4 | 4 | 4 | 4 | 4 | 5 | 2 | 4 | 2 |
| | 1.0 (1.12) | 4 | 2 | 4 | 2 | 4 | 3 | 5 | 2 | 4 | 1 |
| | 1.0 (1.12) | 5 | 3 | 5 | 3 | 5 | 4 | 4 | 3 | 4 | 1 |
| | 0.5 (0.56) | 4 | 3 | 5 | 4 | 4 | 3 | 5 | 2 | 4 | 2 |
| | 0.25 (0.28) | 3 | 3 | 4 | 3 | 4 | 3 | 4 | 3 | 4 | 1 |
| | 0.25 (0.28) | 3 | 2 | 5 | 3 | 4 | 3 | 5 | 2 | 3 | 2 |
| | 0.125 (0.14) | 3 | 3 | 5 | 3 | 4 | 3 | 4 | 2 | 3 | 1 |
| | 0.0625 (0.07) | 2 | 1 | 4 | 2 | 2 | 2 | 3 | 1 | 3 | 1 |
| 84 | 8.0 (8.96) | 1 | 1 | 1 | 1 | 1 | 1 | 1 | 1 | 1 | 1 |
| 33 | 8.0 (8.96) | 5 | 5 | 5 | 5 | 5 | 5 | 5 | 5 | 5 | 5 |
| | 4.0 (4.48) | 4 | 4 | 5 | 4 | 5 | 4 | 5 | 4 | 4 | 2 |
| | 2.0 (2.24) | 5 | 4 | 5 | 3 | 3 | 4 | 5 | 3 | 4 | 2 |
| | 1.0 (1.12) | 4 | 4 | 4 | 3 | 4 | 4 | 5 | 2 | 4 | 2 |
| | 1.0 (1.12) | 5 | 4 | 5 | 4 | 4 | 4 | 5 | 4 | 4 | 3 |
| 33 | 0.5 (0.56) | 5 | 4 | 5 | 3 | 5 | 4 | 4 | 4 | 5 | 2 |
| | 0.25 (0.28) | 5 | 4 | 4 | 4 | 5 | 3 | 5 | 3 | 4 | 1 |
| | 0.25 (0.28) | 4 | 4 | 5 | 3 | 4 | 3 | 5 | 3 | 4 | 1 |
| | 0.125 (0.14) | 2 | 3 | 5 | 4 | 3 | 4 | 5 | 3 | 4 | 2 |
| | 0.0625 (0.07) | 2 | 3 | 4 | 2 | 2 | 2 | 3 | 2 | 3 | 1 |
| 83 | 8.0 (8.96) | 5 | 4 | 5 | 3 | 5 | 4 | 4 | 4 | 5 | 2 |
| | 4.0 (4.48) | 5 | 5 | 5 | 4 | 5 | 4 | 5 | 4 | 5 | 3 |
| | 2.0 (2.24) | 4 | 5 | 5 | 3 | 4 | 4 | 5 | 2 | 5 | 4 |
| | 1.0 (1.12) | 3 | 4 | 5 | 3 | 3 | 4 | 5 | 3 | 4 | 2 |
| | 1.0 (1.12) | 5 | 3 | 5 | 4 | 5 | 4 | 4 | 3 | 4 | 2 |
| | 0.5 (0.56) | 2 | 2 | 4 | 2 | 3 | 3 | 4 | 1 | 3 | 1 |
| | 0.25 (0.28) | 2 | 2 | 4 | 2 | 2 | 3 | 3 | 1 | 2 | 1 |
| 85 | 8.0 (8.96) | 1 | 1 | 3 | 1 | 2 | 2 | 2 | 1 | 2 | 1 |
| 86 | 8.0 (8.96) | 1 | 2 | 3 | 2 | 3 | 1 | 3 | 1 | 3 | 1 |
| 92 | 8.0 (8.96) | 5 | | 5 | 4 | 4 | 4 | 4 | 4 | 5 | 2 |
| | 4.0 (4.48) | 4 | 5 | 5 | 4 | 5 | 4 | 5 | 4 | 5 | 4 |
| | 2.0 (2.24) | 4 | 4 | 5 | 4 | 5 | 5 | 4 | 4 | 5 | 2 |
| | 1.0 (1.12) | 5 | 4 | 5 | 4 | 5 | 4 | 4 | 2 | 5 | 2 |
| | 1.0 (1.12) | 4 | 4 | 4 | 3 | 4 | 5 | 5 | 3 | 4 | 2 |
| | 0.5 (0.56) | 3 | 4 | 4 | 3 | 5 | 4 | 5 | 2 | 4 | 2 |
| | 0.25 (0.28) | 3 | 4 | 4 | 3 | 4 | 4 | 4 | 2 | 4 | 1 |
| | 0.25 (0.28) | 3 | 4 | 2 | 2 | 4 | 4 | 5 | 2 | 4 | 2 |
| | 0.125 (0.14) | 2 | 2 | 4 | 2 | 3 | 3 | 2 | 2 | 3 | 2 |
| | 0.0625 (0.07) | 2 | 2 | 4 | 2 | 3 | 3 | 2 | 2 | 3 | 2 |
| 32 | 8.0 (8.96) | 2 | 4 | 5 | 2 | 1 | 3 | 2 | 2 | 2 | 2 |
| | 4.0 (4.48) | 1 | 3 | 4 | 3 | 1 | 2 | 2 | 1 | 3 | 1 |
| | 2.0 (2.24) | 1 | 3 | 3 | 2 | 1 | 2 | 2 | 1 | 3 | 1 |
| | 1.0 (1.12) | 1 | 1 | 2 | 2 | 1 | 2 | 2 | 1 | 2 | 1 |
| 4 | 8.0 (8.96) | 2 | 5 | 4 | 2 | 3 | 2 | 4 | 4 | 4 | 1 |
| | 4.0 (4.48) | 3 | 3 | 5 | 2 | 3 | 3 | 5 | 3 | 5 | 2 |
| | 2.0 (2.24) | 4 | 2 | 4 | 2 | 3 | 2 | 3 | 1 | 4 | 1 |
| | 1.0 (1.12) | 1 | 3 | 4 | 2 | 2 | 1 | 3 | 1 | 4 | 1 |
| | 1.0 (1.12) | 4 | 3 | 4 | 3 | 2 | 3 | 5 | 1 | 3 | 2 |
| | 0.5 (0.56) | 3 | 3 | 4 | 2 | 3 | 2 | 5 | 1 | 3 | 2 |
| | 0.25 (0.28) | 2 | 3 | 4 | 2 | 2 | 3 | 4 | 1 | 3 | 1 |
| | 0.25 (0.28) | 2 | 3 | 4 | 1 | 1 | 2 | 4 | 1 | 3 | 1 |
| | 0.125 (0.14) | 2 | 2 | 3 | 1 | 1 | 2 | 2 | 1 | 2 | 1 |
| | 0.0625 (0.07) | 1 | 2 | 3 | 1 | 1 | 1 | 1 | 1 | 2 | 1 |
| 70 | 8.0 (8.96) | 3 | | 5 | 4 | 5 | 2 | 4 | 4 | 4 | 4 |
| | 4.0 (4.48) | 2 | 4 | 5 | 4 | 4 | 3 | 4 | 4 | 4 | 3 |
| | 2.0 (2.24) | 1 | 3 | 4 | 2 | 2 | 2 | 2 | 2 | 4 | 2 |
| | 1.0 (1.12) | 1 | 2 | 3 | 2 | 3 | 2 | 4 | 2 | 3 | 2 |
| | 1.0 (1.12) | 2 | 3 | 3 | 3 | 2 | 1 | 4 | 1 | 3 | 2 |
| | 0.5 (0.56) | 2 | 3 | 2 | 2 | 1 | 2 | 3 | 1 | 4 | 1 |
| | 0.25 (0.28) | 1 | 2 | 2 | 2 | 2 | 2 | 3 | | | |
| 92 | 8.0 (8.96) | 5 | 5 | 5 | 2 | 5 | 5 | 5 | 1 | 5 | 4 |
| | 4.0 (4.48) | 5 | 5 | 5 | 2 | 5 | 4 | 4 | 2 | 5 | 3 |

TABLE III-continued

| Example No. of Compound Tested | Rate of Appln. lbs/acre (kg/ha) | Tomato | Large Crab-grass | Pig-weed | Fox-tail | Velvet-leaf | Morning-glory | Zinnia | Barn-yard Grass | Mus-tard | Wild Oats |
|---|---|---|---|---|---|---|---|---|---|---|---|
| | 2.0 (2.24) | 5 | 4 | 5 | 4 | 4 | 3 | 5 | 2 | 5 | 2 |
| | 1.0 (1.12) | 5 | 4 | 4 | 2 | 5 | 3 | 4 | 1 | 5 | 2 |
| | 0.25 (0.28) | 5 | 2 | 2 | 4 | 3 | 3 | 4 | 2 | 4 | 2 |
| | 0.125 (0.14) | 4 | 2 | 2 | 3 | 4 | 3 | 4 | 2 | 4 | 2 |
| | 0.0625 (0.07) | 4 | 2 | 2 | 2 | 2 | 2 | 3 | 2 | 3 | 1 |
| 93 | 8.0 (8.96) | 5 | 4 | 5 | 5 | 5 | 5 | 5 | 4 | 5 | 5 |
| | 4.0 (4.48) | 5 | 4 | 5 | 4 | 3 | 4 | 4 | 2 | 4 | 3 |
| | 2.0 (2.24) | 4 | 3 | 5 | 3 | 4 | 3 | 4 | 2 | 4 | 2 |
| | 1.0 (1.12) | 3 | 2 | 2 | 2 | 3 | 3 | 3 | 2 | 4 | 1 |
| 94 | 8.0 (8.96) | 5 | 4 | 5 | 5 | 5 | 5 | 5 | 4 | 5 | 4 |
| | 4.0 (4.48) | 5 | 5 | 5 | 5 | 5 | 4 | 5 | 2 | 4 | 4 |
| | 2.0 (2.24) | 5 | 4 | 4 | 4 | 5 | 4 | 5 | 3 | 3 | 2 |
| | 1.0 (1.12) | 3 | 3 | 4 | 3 | 4 | 3 | 5 | 2 | 4 | 2 |
| 98 | 8.0 (8.96) | 5 | 4 | 5 | 5 | 5 | 5 | 4 | 5 | 5 | 5 |
| | 4.0 (4.48) | 5 | 4 | 5 | 5 | 5 | 5 | 5 | 5 | 5 | 5 |
| | 2.0 (2.24) | 5 | 3 | 4 | 5 | 5 | 4 | 5 | 5 | 4 | 5 |
| | 1.0 (1.12) | 4 | 2 | 4 | 5 | 5 | 3 | 4 | 5 | 3 | 3 |
| | 1.0 (1.12) | 5 | 2 | 4 | 5 | 5 | 3 | 4 | 5 | 3 | 5 |
| | 0.5 (0.56) | 5 | 2 | 4 | 5 | 5 | 3 | 2 | 5 | 3 | 4 |
| | 0.25 (0.28) | 3 | 1 | 3 | 3 | 5 | 2 | 1 | 4 | 2 | 2 |
| | 0.25 (0.28) | 4 | 1 | 3 | 5 | 5 | 3 | 3 | 4 | 3 | 4 |
| | 0.125 (0.14) | 2 | 1 | 2 | 2 | 5 | 1 | 1 | 3 | 2 | 2 |
| | 0.0625 (0.07) | 1 | 1 | 1 | 2 | 3 | 1 | 1 | 3 | 2 | 2 |
| 99 | 8.0 (8.96) | 5 | 5 | 5 | 5 | 5 | 5 | 5 | 5 | 5 | 5 |
| | 4.0 (4.48) | 5 | 4 | 5 | 5 | 5 | 5 | 5 | 5 | 5 | 5 |
| | 2.0 (2.24) | 5 | 3 | 5 | 5 | 5 | 4 | 4 | 5 | 4 | 5 |
| | 1.0 (1.12) | 5 | 3 | 4 | 4 | 5 | 4 | 3 | 5 | 4 | 5 |
| | 1.0 (1.12) | 4 | 2 | 4 | 5 | 5 | 3 | 3 | 5 | 4 | 5 |
| | 0.5 (0.56) | 5 | 1 | 4 | 5 | 5 | 3 | 3 | 4 | 4 | 4 |
| | 0.25 (0.28) | 4 | 1 | 2 | 3 | 4 | 2 | 2 | 4 | 3 | 2 |
| | 0.25 (0.28) | 4 | 1 | 3 | 3 | 4 | 2 | 1 | 3 | 3 | 4 |
| | 0.125 (0.14) | 4 | 1 | 3 | 2 | 4 | 2 | 1 | 3 | 3 | 2 |
| | 0.0625 (0.07) | 2 | 1 | 2 | 2 | 3 | 2 | 1 | 3 | 2 | 1 |
| 100 | 8.0 (8.96) | 5 | 2 | 5 | 5 | 5 | 2 | 3 | 5 | 5 | 5 |
| | 4.0 (4.48) | 5 | 2 | 1 | 5 | 5 | 4 | 2 | 4 | 4 | 4 |
| | 2.0 (2.24) | 5 | 1 | 1 | 5 | 4 | 3 | 1 | 4 | 3 | 3 |
| | 1.0 (1.12) | 4 | 1 | 1 | 4 | 4 | 2 | 1 | 3 | 3 | 2 |
| | 1.0 (1.12) | 4 | 1 | 1 | 5 | 4 | 1 | 1 | 3 | 3 | 3 |
| | 0.5 (0.56) | 3 | 1 | 1 | 4 | 4 | 1 | 1 | 3 | 3 | 3 |
| | 0.25 (0.28) | 1 | 1 | 1 | 3 | 3 | 1 | 1 | 2 | 3 | 2 |
| 101 | 8.0 (8.96) | 5 | 4 | 4 | 5 | 5 | 4 | 4 | 5 | 4 | 5 |
| | 4.0 (4.48) | 5 | 1 | 2 | 5 | 5 | 3 | 2 | 4 | 3 | 4 |
| | 2.0 (2.24) | 4 | 1 | 1 | 5 | 5 | 2 | 1 | 4 | 3 | 3 |
| | 1.0 (1.12) | 3 | 1 | 1 | 4 | 5 | 1 | 1 | 3 | 3 | 2 |
| | 1.0 (1.12) | 3 | 1 | 1 | 4 | 5 | 1 | 1 | 2 | 3 | 3 |
| | 0.5 (0.56) | 2 | 1 | 1 | 3 | 5 | 1 | 1 | 3 | 3 | 3 |
| | 0.25 (0.28) | 3 | 1 | 1 | 3 | 4 | 2 | 1 | 3 | 3 | 4 |

EXPERIMENT 3

A greenhouse study was also conducted in an effort to evaluate the herbicidal activity of compounds of example number 3 and 95. The compounds were formulated by combining approximately 4% active, 4% alkylnaphthalene sulphonate and 92% water. The formulated compounds were applied both preemergent and postemergent. Data was recorded 32 days after treatment for preemergent and 35 days after treatment for postemergent as percent crop vigor and percent weed control as compared to control plots. This data appears below in Tables IV (preemergence) and V (postemergence).

TABLE IV

| | | Preemergence | | | | | | | | | |
|---|---|---|---|---|---|---|---|---|---|---|---|
| Example No. of Compound Tested | Application Rate kg/ha | Percent Crop Vigor | | Percent Weed Control | | | | | | | |
| | | Wheat | Barley | A. fatua | A. myosuroides | P. annua | S. media | V hederifolia | G. aparine | P. persicaria |
| 3 | 2.0 | 92 | 100 | 59 | 97 | 100 | 99 | 76 | 58 | 100 |
| | 1.5 | 100 | 98 | 32 | 90 | 98 | 100 | 67 | 39 | 98 |
| | 1.0 | 97 | 96 | 23 | 87 | 95 | 99 | 50 | 39 | 99 |
| | 0.5 | 99 | 99 | 0 | 82 | 88 | 95 | 28 | 0 | 97 |
| 95 | 2.0 | 97 | 75 | 95 | 100 | 100 | 100 | 72 | 97 | 100 |
| | 1.5 | 98 | 64 | 43 | 100 | 100 | 100 | 53 | 45 | 100 |
| | 1.0 | 98 | 68 | 43 | 99 | 100 | 99 | 58 | 16 | 100 |
| | 0.5 | 99 | 97 | 0 | 97 | 98 | 92 | 14 | 1 | 100 |

TABLE V

| Example No. of Compound Tested | Application Rate kg/ha | Percent Crop Vigor Wheat | Percent Crop Vigor Barley | Postemergence Percent Weed Control A. fatua | A. myosuroides | P. annua | S. media | V hederifolia | G. aparine | P. persicaria |
|---|---|---|---|---|---|---|---|---|---|---|
| 3 | 1.0 | 100 | 100 | 5 | 3 | 100 | 97 | 36 | 17 | 100 |
|  | 0.5 | 99 | 100 | 1 | 4 | 100 | 95 | 7 | 15 | 100 |
|  | 0.25 | 100 | 100 | 0 | 5 | 100 | 5 | 19 | 7 | 100 |
|  | 0.125 | 98 | 99 | 0 | 0 | 93 | 43 | 5 | 12 | 100 |
| 95 | 1.0 | 97 | 78 | 65 | 95 | 100 | 94 | 94 | 97 | 100 |
|  | 0.5 | 97 | 100 | 7 | 90 | 99 | 50 | 65 | 46 | 100 |
|  | 0.25 | 97 | 100 | 2 | 10 | 82 | 54 | 14 | 5 | 100 |
|  | 0.125 | 98 | 99 | 1 | 11 | 81 | 43 | 11 | 5 | 100 |

The present compounds have also been found to display useful activity as aquatic algicides. It is therefore provided as another embodiment of the invention a method for controlling the growth of aquatic algae which comprises applying to the water containing said algae a growth inhibiting amount of a 4-pyrazolecarboxamide of the invention. These active agents are generally applied at rates effective to inhibit the growth of algae without causing significant toxicity to other aquatic life. The compounds are applied at rates in the range of from about 20.0 ppm to about 0.1 ppm, more preferably at 10 ppm to 0.5 ppm.

EXPERIMENT 4

The initial screening procedure used to detect aquatic algicidal activity was conducted at a test compound concentration of 10 ppm against the algae *Chlorella vulgaris* (A), *Scenedesmus quadricanda* (B), *Anacystis nidulans* (C) and *Anabaena flos-aquae* (D). Certain test compounds were also evaluated against additional species of algae at lower concentration rates. These species are as follows:

E. *Stichococcus bascillaris*
F. Anabaena spp.
G. *Anabaena spiroides*

These species of algae were grown on agar slants containing artificial Hughes' media. Each species of algae was suspended in 5 ml of an aqueous, sterile Hughes' media by washing the agar slants. This solution was then pipetted into a volume of 400 ml of the sterile media. Two ml of the inoculated media was transferred via syringe to a sterilized 12 ml vial, to which 10 μl of the formulated compound was added to obtain a concentration of 10 ppm of the compound. The compounds were formulated by adding 10 mg compound to 0.5 ml acetone and 4.5 ml sterile 0.1 percent Tween 80. Lower concentrations were obtained by further serial dilution. After addition the vial was stoppered.

Observations were made 7 days after treatment and the activity of the test compounds against algae growth is recorded in Table VI according to the following scale:

1 = no effect
2 = slight effect
3 = moderate effect
4 = heavy control
5 = 100% control

TABLE VI

| Example No. of Compound Tested | Concentration ppm | A | B | C | D | E | F | G |
|---|---|---|---|---|---|---|---|---|
| 3 | 10.0 | 5 | 4 | 5 | 5 | | | |

TABLE VI-continued

| Example No. of Compound Tested | Concentration ppm | A | B | C | D | E | F | G |
|---|---|---|---|---|---|---|---|---|
| 4 | 10.0 | 4 | 5 | 5 | 5 | | | |
|  | 1.0 | 2 | 4 | 5 | 4 | 3 | 4 | 4 |
|  | 0.5 | 2 | 4 | 4 | 4 | 2 | 4 | 4 |
| 6 | 10.0 | 4 | 4 | 5 | 5 | | | |
| 7 | 10.0 | 5 | 5 | 4 | 5 | | | |
| 21 | 10.0 | 4 | 5 | 5 | 4 | | | |
| 24 | 10.0 | 4 | 4 | 5 | 5 | | | |
|  | 1.0 | 4 | 5 | 5 | 4 | 5 | 5 | 5 |
|  | 0.5 | 2 | 4 | 4 | 4 | 4 | 5 | 4 |
| 25 | 10.0 | 4 | 5 | 4 | 4 | | | |
| 30 | 10.0 | 4 | 5 | 4 | 4 | | | |
| 31 | 10.0 | 5 | 4 | 5 | 5 | | | |
| 32 | 10.0 | 4 | 5 | 5 | 4 | | | |
|  | 1.0 | 1 | 3 | 1 | 1 | 1 | 2 | 3 |
|  | 0.5 | 1 | 3 | 2 | 1 | 1 | 1 | 3 |
| 33 | 10.0 | 4 | 5 | 5 | 5 | | | |
|  | 1.0 | 4 | 5 | 5 | 4 | 5 | 5 | 5 |
|  | 0.5 | 3 | 5 | 5 | 3 | 4 | 5 | 4 |
| 36 | 10.0 | 4 | 4 | 5 | 5 | | | |
| 37 | 10.0 | 4 | 5 | 4 | 4 | | | |
| 39 | 10.0 | 4 | 5 | 5 | 5 | | | |
|  | 1.0 | 4 | 5 | 4 | 4 | 1 | 5 | 4 |
|  | 0.5 | 2 | 5 | 4 | 2 | 1 | 5 | 5 |
| 76 | 10.0 | 4 | 4 | 4 | 5 | | | |
| 81 | 10.0 | 5 | 4 | 5 | 5 | | | |
| 83 | 10.0 | 4 | 4 | 5 | 5 | | | |
|  | 1.0 | 1 | 3 | 2 | 1 | 1 | 3 | 2 |
|  | 0.5 | 1 | 3 | 1 | 1 | 1 | 1 | 1 |
| 84 | 10.0 | 4 | 4 | 4 | 4 | | | |
|  | 1.0 | 1 | 1 | 1 | 1 | 1 | 1 | 1 |
|  | 0.5 | 1 | 1 | 1 | 1 | 1 | 1 | 1 |
| 85 | 10.0 | 1 | 1 | 1 | 1 | | | |
| 86 | 10.0 | 1 | 4 | 1 | 2 | | | |
| 87 | 10.0 | 4 | 4 | 4 | 5 | | | |
| 88 | 10.0 | 4 | 5 | 4 | 4 | | | |
| 91 | 10.0 | 4 | 4 | 4 | 5 | | | |
| 95 | 10.0 | 4 | 5 | 5 | 5 | | | |
|  | 1.0 | 1 | 4 | 5 | 3 | 3 | 4 | 3 |
|  | 0.5 | 2 | 3 | 4 | 4 | 1 | 4 | 4 |

The compounds of the present invention have also been found to display excellent activity as aquatic herbicides. Therefore yet another embodiment of the invention is a method for controlling the growth of aquatic plants which comprises contacting the plants or the water in which the plants are growing with an aquatic herbicidally-effective amount of a compound of the invention. This method is practiced by adding the compound of the invention to the water containing the submerged, emergent or floating aquatic plants, or otherwise contacting the plants with the compounds, for example, by applying the compounds to the sub-aqueous soil in which the aquatic plants are rooted. The optimum concentration of active ingredient to control the growth of aquatic plants varies with the temperature, the species to be controlled, and the type and shape of the body of water to be treated. Generally the compounds are applied at rates in the range of from about 15.0 ppm to about 0.1 ppm, more preferably at 10 ppm to 0.5 ppm.

EXPERIMENT 5

The following procedure was used to evaluate the aquatic herbicidal activity of the compounds of the invention. The compounds were formulated for evaluation as described above in Experiment 4, and the aquatic herbicidal activity was determined by visual observations based upon non-treated controls. Activity ratings were made on a scale of from 1 to 5 as described above. The result of this test appears below in Table VII.

TABLE VII

| Example No. of Compound Tested | Concen- ppm | Aquatic Herbicide | | |
|---|---|---|---|---|
| | | Hydrilla | Coontail | Duckweed |
| 4 | 4.0 | 5 | 5 | 4 |
| | 2.0 | 5 | 5 | 4 |
| 24 | 4.0 | 5 | 4 | 5 |
| | 2.0 | 5 | 3 | 5 |
| 33 | 4.0 | 5 | 3 | 5 |
| | 2.0 | 5 | 2 | 4 |
| 39 | 4.0 | 4 | 2 | 4 |
| | 2.0 | 4 | 2 | 3 |
| 83 | 4.0 | 1 | 2 | 1 |
| | 2.0 | 1 | 2 | 1 |
| 84 | 4.0 | 2 | 2 | 1 |
| | 2.0 | 2 | 1 | 1 |
| 95 | 4.0 | 5 | 4 | 4 |
| | 2.0 | 5 | 3 | 4 |

The compounds of the present invention have also exhibited useful activity against various plant fungal diseases such as leaf rust, powdery mildew, Septoria leaf blotch, Helminthosporium leaf spot and the like. When employed in the treatment of such plant fungal diseases, the compounds are applied to the plants in a disease inhibiting and non-herbicidal amount. The term "disease inhibiting and non-herbicidal amount," as used herein, refers to an amount of a compound of the invention which kills or stunts the plant disease for which control is desired, but is not significantly toxic to the plant. This amount will generally be from about 1 to 1000 ppm, with 10 to 500 ppm being preferred. The exact concentration of the compound required varies with the fungal disease to be controlled, the type of formulation employed, the method of application, the particular plant species, climate conditions and the like. The compounds are preferably formulated prior to application for fungal disease control, and may be formulated as described above.

I claim:

1. A compound of the formula

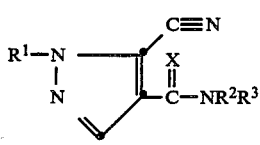

wherein

R$^1$ is C$_1$-C$_6$ alkyl, C$_5$-C$_6$ cycloalkyl,

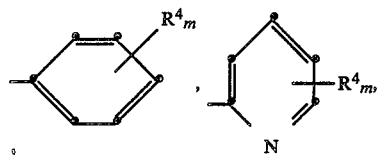

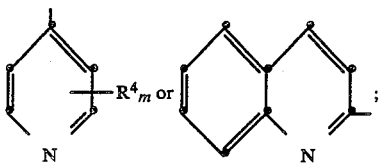

each of R$^2$ and R$^3$ is taken separately and is independently hydrogen, C$_1$-C$_4$ alkyl, C$_3$-C$_4$ alkenyl, C$_3$-C$_4$ alkynyl, C$_3$-C$_4$ cycloalkyl or C$_1$-C$_3$ alkoxy, or R$^2$ and R$^3$ are taken together with the nitrogen atom to which they are attached and form piperidine, morpholine or pyrrolidine;

each R$^4$ independently is halogen, C$_1$-C$_4$ alkyl, C$_1$-C$_4$ alkoxy, C$_1$-C$_4$ haloalkyl, C$_1$-C$_4$ haloalkoxy or cyano;

X is O or S; and m is 0–3;

with the provisos that when R$^4$ is C$_1$-C$_4$ alkyl, that substituent exists at other than the 2 or 6 position of the phenyl ring; and when R$^2$ is C$_1$-C$_3$ alkoxy R$^3$ is other than C$_1$-C$_3$ alkoxy.

2. A compound of claim 1 wherein R$^1$ is

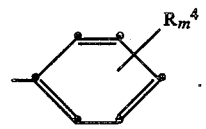

3. The compound of claim 2 which is 5-cyano-1-phenyl-N-methyl-1H-pyrazole-4-carboxamide.

4. The compound of claim 2 which is 5-cyano-1-phenyl-N-cyclopropyl-1H-pyrazole-4-carboxamide.

5. The compound of claim 2 which is 5-cyano-1-(4-chlorophenyl)-N-methyl-1H-pyrazole-4-carboxamide.

6. The compound of claim 2 which is 5-cyano-1-(4-chlorophenyl)-N-methyl-N-ethyl-1H-pyrazole-4-carboxamide.

7. The compound of claim 2 which is 5-cyano-1-(4-bromophenyl)-N-methyl-1H-pyrazole-4-carboxamide.

8. The compound of claim 2 which is 5-cyano-1-(2,4-dichlorophenyl)-N-methyl-1H-pyrazole-4-carboxamide.

9. A compound of claim 1 wherein R$^1$ is

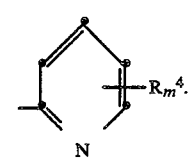

10. The compound of claim 9 which is 5-cyano-1-(2-pyridinyl)-N-methyl-1H-pyrazole-4-carboxamide.

11. The compound of claim 9 which is 5-cyano-1-(2-pyridinyl)-N-methyl-N-methoxy-1H-pyrazole-4-carboxamide.

12. The compound of claim 9 which is 5-cyano-1-(2-pyridinyl)-N-cyclopropyl-1H-pyrazole-4-carboxamide.

13. A compound of claim 1 wherein $R^1$ is $C_1$-$C_6$ alkyl.

14. A compound of claim 13 wherein $R^1$ is tert-butyl.

15. The compound of claim 14 which is 5-cyano-1-tert-butyl-N-methyl-1H-pyrazole-4-carboxamide.

16. The compound of claim 14 which is 5-cyano-1-tert-butyl-N-cyclopropyl-1H-pyrazole-4-carboxamide.

17. The compound of claim 14 which is 5-cyano-1-tert-butyl-N-ethyl-1H-pyrazole-4-carboxamide.

18. The compound of claim 14 which is 5-cyano-1-tert-butyl-N,N-dimethyl-1H-pyrazole-4-carboxamide.

19. A composition which comprises from about 0.1 to about 95.0 percent by weight of a compound of claim 1 and an agriculturally-acceptable carrier.

20. The composition of claim 19 wherein the compound is 5-cyano-1-phenyl-N-methyl-1H-pyrazole-4-carboxamide.

21. The composition of claim 19 wherein the compound is 5-cyano-1-phenyl-N-cyclopropyl-1H-pyrazole-4-carboxamide.

22. The composition of claim 19 wherein the compound is 5-cyano-1-(4-chlorophenyl)-N-methyl-1H-pyrazole-4-carboxamide.

23. The composition of claim 19 wherein the compound is 5-cyano-1-(4-chlorophenyl)-N-methyl-N-ethyl-1H-pyrazole-4-carboxamide.

24. The composition of claim 19 wherein the compound is 5-cyano-1-(4-bromophenyl)-N-methyl-1H-pyrazole-4-carboxamide.

25. The composition of claim 19 wherein the compound is 5-cyano-1-(2,4-dichlorophenyl)-N-methyl-1H-pyrazole-4-carboxamide.

26. The composition of claim 19 wherein the compound is 5-cyano-1-(2-pyridinyl)-N-methyl-1H-pyrazole-4-carboxamide.

27. The composition of claim 19 wherein the compound is 5-cyano-1-(2-pyridinyl)-N-methyl-N-methoxy-1H-pyrazole-4-carboxamide.

28. The composition of claim 19 wherein the compound is 5-cyano-1-(2-pyridinyl)-N-cyclopropyl-1H-pyrazole-4-carboxamide.

29. The composition of claim 19 wherein the compound is 5-cyano-1-tert-butyl-N-methyl-1H-pyrazole-4-carboxamide.

30. A method of controlling weeds in a wheat or corn crop which comprises applying preemergently an effective amount of an active agent which is a compound of claim 1.

31. The method of claim 30 wherein the active agent is 5-cyano-1-phenyl-N-methyl-1H-pyrazole-4-carboxamide.

32. The method of claim 30 wherein the active agent is 5-cyano-1-tert-butyl-N-methyl-1H-pyrazole-4-carboxamide.

33. A method for controlling undesired plants which comprises applying to the plants a growth inhibiting amount of a compound of claim 1.

34. The method of claim 33 wherein the compound is 5-cyano-1-phenyl-N-methyl-1H-pyrazole-4-carboxamide.

35. The method of claim 33 wherein the compound is 5-cyano-1-phenyl-N-cyclopropyl-1H-pyrazole-4-carboxamide.

36. The method of claim 33 wherein the compound is 5-cyano-1-(4-chlorophenyl)-N-methyl-1H-pyrazole-4-carboxamide.

37. The method of claim 33 wherein the compound is 5-cyano-1-(4-chlorophenyl)-N-methyl-N-ethyl-1H-pyrazole-4-carboxamide.

38. The method of claim 33 wherein the compound is 5-cyano-1-(4-bromophenyl)-N-methyl-1H-pyrazole-4-carboxamide.

39. The method of claim 33 wherein the compound is 5-cyano-1-(2,4-dichlorophenyl)-N-methyl-1H-pyrazole-4-carboxamide.

40. The method of claim 33 wherein the compound is 5-cyano-1-(2-pyridinyl)-N-methyl-1H-pyrazole-4-carboxamide.

41. The method of claim 33 wherein the compound is 5-cyano-1-(2-pyridinyl)-N-methyl-N-methoxy-1H-pyrazole-4-carboxamide.

42. The method of claim 33 wherein the compound is 5-cyano-1-(2-pyridinyl)-N-cyclopropyl-1H-pyrazole-4-carboxamide.

43. The method of claim 33 wherein the compound is 5-cyano-1-tert-butyl-N-methyl-1H-pyrazole-4-carboxamide.

44. A method for controlling the growth of aquatic algae which comprises applying to the water containing said algae a growth inhibiting amount of a compound of claim 1.

45. A method for controlling the growth of aquatic plants which comprises contacting the plants or the water in which the plants are growing with an aquatic herbicidally-effective amount of a compound of claim 1.

* * * * *